(12) United States Patent
Escribano et al.

(10) Patent No.: US 10,053,429 B2
(45) Date of Patent: Aug. 21, 2018

(54) DGAT2 INHIBITORS

(71) Applicant: Eli Lilly and Company, Indianapolis, IN (US)

(72) Inventors: Ana Maria Escribano, Madrid (ES); Maria Rosario Gonzalez, Madrid (ES); Celia Lafuente Blanco, Madrid (ES); Maria Dolores Martin-Ortega Finger, Madrid (ES); Michael R Wiley, Zionsville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 15/571,052

(22) PCT Filed: May 19, 2016

(86) PCT No.: PCT/US2016/033196
§ 371 (c)(1),
(2) Date: Nov. 1, 2017

(87) PCT Pub. No.: WO2016/187384
PCT Pub. Date: Nov. 24, 2016

(65) Prior Publication Data
US 2018/0162825 A1 Jun. 14, 2018

Related U.S. Application Data

(60) Provisional application No. 62/165,323, filed on May 22, 2015.

(30) Foreign Application Priority Data

May 20, 2015 (EP) .................................... 15382264

(51) Int. Cl.
*C07D 239/42* (2006.01)
*C07D 401/12* (2006.01)

(52) U.S. Cl.
CPC ......... *C07D 239/42* (2013.01); *C07D 401/12* (2013.01)

(58) Field of Classification Search
CPC ............................ C07D 239/42; C07D 401/12
USPC ....................................................... 514/235.8
See application file for complete search history.

(56) References Cited

FOREIGN PATENT DOCUMENTS

| WO | 2008121570 | 10/2008 |
|----|------------|---------|
| WO | 2009083553 | 7/2009 |
| WO | 2011078102 | 6/2011 |
| WO | 2013150416 | 10/2013 |
| WO | 2015077299 | 5/2015 |

OTHER PUBLICATIONS

Matsuda, et al., "DGAT Inhibitors for Obesity," Current Opinion in Investigational Drugs, Pharmapress, US, vol. 8, No. 10, pp. 836-884, Oct. 1, 2007.

*Primary Examiner* — Kristin Ann Vajda
(74) *Attorney, Agent, or Firm* — Macharri Vorndran-Jones

(57) ABSTRACT

The present invention provides compounds of the Formula below: [Formula should be inserted here] Where A, X, R. and R2-R3 are as described herein; methods of treating patients for hypertriglyceridemia and cardiovascular disease including dyslipidemia and atherosclerosis, and processes for preparing the compounds.

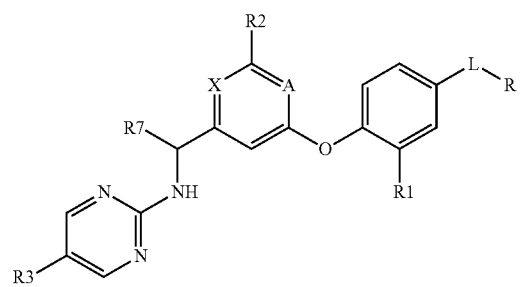

25 Claims, No Drawings

DGAT2 INHIBITORS

The present invention is directed to novel compounds useful for inhibiting Diacylglycerol O-acyltransferase 2 (DGAT2), which may provide useful therapies for treating elevated triglyceride levels and cardiovascular diseases including dyslipidemia and atherosclerosis. The present invention is also directed to a process for preparing the novel compounds.

The average triglyceride level in people, particular in populations in the western hemisphere, has risen at an alarming rate in the last 30 years. The increase in triglyceride levels, or hypertriglyceridemia, has been associated with a number of disease risks including an increased risk of cardiovascular diseases such as dyslipidemia and atherosclerosis. The increase in triglyceride levels has also coincided with a dramatic increase in obesity, insulin resistance type-2-diabetes, hepatic steatosis, non-alcoholic fatty liver disease (NAFLD) and non-alcoholic steatohepatitis (NASH). Elevated triglyceride levels or hypertriglyceridemia is implicated in a variety of diseases and conditions; consequently, controlling triglyceride levels may provide a viable treatment for metabolic disease.

Diacylglycerol O-acyltransferase 2 (DGAT2) is expressed in many tissues; however, it is expressed mainly in the liver and white adipose tissue. It is implicated, along with DGAT1, in the last step for triglyceride synthesis. The inhibition of DGAT2 activity leading to a reduction in triglyceride levels will suppress low density lipoprotein cholesterol (LDL-c) by controlling either production via ApoB secretion or deposition of those particles. Both mechanisms have been pharmacologically validated in humans. Limiting secretion of apolipoprotein B (ApoB) particles reduces LDL-c production. Therefore attenuation of DGAT2 activity has favorable impact on triglyceride levels, LDL-c, ApoB, and triglyceride-rich lipoprotein concentration in circulation and lipogenesis in the liver.

WO2013/150416 discloses certain derivatives of purine, pyrimidine, and pyrazine compounds as DGAT2 inhibitors and their use in treating diseases associated with DGAT2 activity.

There is a need for additional drugs and therapies for the treatment of hypercholesterolemia and cardiovascular diseases such as dyslipidemia and atherosclerosis. Current treatment methods, which include diet, lifestyle changes, and/or statin therapy, may not lower LDL-c levels sufficiently for all patients at risk for cardiovascular diseases. Further there is a subset of patients that are intolerant or become intolerant to statin therapy. The present invention addresses one or more of these needs by providing alternative compounds and treatment methods, which may be suitable for the treatment cardiovascular diseases.

The present invention provides a compound according to Formula 1, or a pharmaceutically acceptable salt thereof,

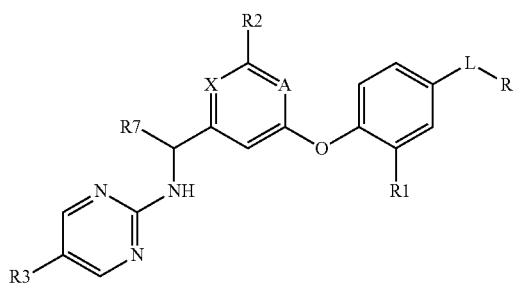

where X is CH or N; A is CH or N, provided that at least one of X and A is N; L is a —$C_{1-3}$alkyl; R is selected from: —$S(O)_2NHR4$, —$NHS(O)_2R5$, and —$NHC(O)R6$; R1 is H or halo; R2 is selected from: H, —$C_{1-2}$ alkyl, —CN, —$CF_3$, —$NH_2$, —$N(H)CH_3$, —$N(CH_3)_2$, —$OCH_3$, —$CH_2$—O—$CH_3$, -cyclopropyl, piperazinyl, 4-methyl piperazinyl, and morpholinyl; R3 is selected from —$C_{1-2}$ alkyl, halo, —$CHF_2$, —$CF_3$, and —$OCH_3$; R4 is H or —$CH_3$; R5 is selected from: —$CH_3$, —$NH_2$, and —$NHCH_3$; R6 is selected from: —$CH_3$, —$CH_2OH$, —$CH_2OCH_3$, —$CH(OH)CH_3$, —$NH_2$, and —$NHCH_3$; R7 is H or —$CH_3$; provided however, that when R1 is H; then R2 is Me, R3 is Cl, R7 is H, X and A are both N, and L-R is not —$(CH_2)S(O)_2$—$NH_2$, or —$(CH_2)S(O)_2$—$NHCH_3$.

In one form, the present invention provides a compound according to Formula 1, or a pharmaceutically acceptable salt thereof where X is CH or N; A is CH or N, provided that at least one of X and A is N; L is a —$C_{1-3}$alkyl; R is selected from: —$S(O)_2NHR4$, —$NHS(O)_2R5$, and —$NHC(O)R6$; R1 is H; R2 is selected from: H, —$C_{1-2}$ alkyl, —CN, —$CF_3$, —$NH_2$, —$N(H)CH_3$, —$N(CH_3)_2$, —$OCH_3$, —$CH_2$—O—$CH_3$, -cyclopropyl, 4-methyl piperazinyl, and morpholinyl; R3 is selected from $C_{1-2}$ alkyl, halo, —$CHF_2$, —$CF_3$, and —$OCH_3$; R4 is H or —$CH_3$; R5 is selected from: —$CH_3$, —$NH_2$, and —$NHCH_3$; R6 is selected from: —$CH_3$, —$CH_2OH$, —$CH_2OCH_3$, —$CH(OH)CH_3$, —$NH_2$, and —$NHCH_3$; and R7 is H; provided that when R2 is Me, R3 is Cl, and X and A are both N, L-R is not —$(CH_2)S(O)_2$—$NH_2$, or —$(CH_2)S(O)_2$—$NHCH_3$.

In one form, the present invention provides a compound according to Formula 1, or a pharmaceutically acceptable salt thereof, where A is N. In certain embodiments, X is CH or N; L is a —$C_{1-3}$alkyl; R is selected from: —$S(O)_2NHR4$, —$NHS(O)_2R5$, and —$NHC(O)$—R6; R1 is H or halo; R2 is selected from: H, —$C_{1-2}$ alkyl, —CN, —$CF_3$, —$NH_2$, —$N(H)CH_3$, —$N(CH_3)_2$, —$OCH_3$, —$CH_2$—O—$CH_3$, -cyclopropyl, 4-methyl piperazinyl, and morpholinyl; R3 is selected from $C_{1-2}$ alkyl, halo, —$CHF_2$, —$CF_3$, and —$OCH_3$; R4 is H or —$CH_3$; R5 is selected from: —$CH_3$, —$NH_2$, and —$NHCH_3$; R6 is selected from: —$CH_3$, —$CH_2OH$, —$CH_2OCH_3$, —$CH(OH)CH_3$, —$NH_2$, and —$NHCH_3$; R7 is H or —$CH_3$.

In another form, the present invention provides a compound according to Formula 1, or a pharmaceutically acceptable salt thereof, where A is N, X is CH or N, L is —$CH_2$— or —$CH_2CH_2$—; R is selected from —$S(O)_2NHR4$ and —$NH(SO)_2R5$; R1 is H; R2 is selected from H, —$C_{1-2}$ alkyl, —CN, —$CF_3$, —$NH_2$, —$N(H)CH_3$, —$N(CH_3)_2$, 4-methyl piperazinyl, and morpholinyl; R3 is $C_{1-2}$ alkyl or Cl; R4 is H; and R5 is —$CH_3$ or —$NH_2$; and R7 is H.

In another form, the present invention provides a compound according to Formula 1, or a pharmaceutically acceptable salt thereof, where A is N, X is CH or N; L is —$CH_2$— or —$CH_2CH_2$—; R is selected from —$S(O)_2NHR4$ and —$NH(SO)_2R5$; R1 is H; R2 is selected from H, —$C_{1-2}$alkyl, —CN, —$CF_3$, —$NH_2$, —$N(H)CH_3$, —$N(CH_3)_2$, 4-methyl piperazinyl, and morpholinyl; R3 is $C_{1-2}$ alkyl or Cl; R4 is —$CH_3$; and R5 is —$CH_3$ or —$NH_2$; and R7 is H.

In another form, the present invention provides a compound according to Formula 1, or a pharmaceutically acceptable salt thereof, where X is N. In one embodiment, A is CH. In another embodiment A is N. For either embodiment, L is a —$C_{1-3}$alkyl; R is selected from: —$S(O)_2NHR4$, —$NHS(O)_2R5$, and —$NHC(O)$—R6; R1 is H; R2 is selected from: H, —$C_{1-2}$ alkyl, —CN, —$CF_3$, —$NH_2$, —$N(H)CH_3$, —$N(CH_3)_2$, —$OCH_3$, —$CH_2$—O—$CH_3$, -cyclopropyl, 4-methyl piperazinyl, and morpholinyl; R3 is selected from $C_{1-2}$ alkyl, Cl, —CHF$_2$, —CF$_3$, and —OCH$_3$; R4 is H or —CH$_3$; R5 is selected from: —CH$_3$, —NH$_2$, and —NHCH$_3$; R6 is selected from: —CH$_3$, —CH$_2$OH, —CH$_2$OCH$_3$, —CH(OH)CH$_3$, —NH$_2$, and —NHCH$_3$; R7 is H.

In one form, the present invention provides a compound according to Formula 1, or a pharmaceutically acceptable salt thereof, where X is CH. In one embodiment A is N. In this embodiment, L is a —$C_{1-3}$alkyl; R is selected from: —S(O)$_2$NHR4, —NHS(O)$_2$R5, and —NHC(O)—R6; R1 is H or halo, R2 is selected from: H, —$C_{1-2}$ alkyl, —CN, —CF$_3$, —NH$_2$, —N(H)CH$_3$, —N(CH$_3$)$_2$, —OCH$_3$, —CH$_2$—O—CH$_3$, -cyclopropyl, 4-methyl piperazinyl, and morpholinyl; R3 is selected from $C_{1-2}$ alkyl, halo, —CHF$_2$—CF$_3$, and —OCH$_3$; R4 is H or —CH$_3$; R5 is selected from: —CH$_3$, —NH$_2$, and —NHCH$_3$; R6 is selected from: —CH$_3$, —CH$_2$OH, —CH$_2$OCH$_3$, —CH(OH)CH$_3$, —NH$_2$, and —NHCH$_3$; R7 is H or —CH$_3$.

In another form, the present invention provides a compound according to Formula 1 where L is —CH$_2$— or —CH$_2$CH$_2$—, or a pharmaceutically acceptable salt thereof. In one embodiment of this form, A is N; X is CH or N, and R is selected from: —S(O)$_2$NHR4, —NHS(O)$_2$R5, and —NHC(O)—R6. Preferably R is —S(O)$_2$NHR4 or —NHS(O)$_2$R5. R1 is H. R2 is selected from H, —$C_{1-2}$ alkyl, —CN, —CF$_3$, —NH$_2$, —N(H)CH$_3$, —N(CH$_3$)$_2$, 4-methyl piperazinyl, and morpholinyl; preferably R2 is H, —CH$_3$, —NH$_2$, and 4-methyl piperazinyl; R3 is a $C_{1-2}$ alkyl or Cl; R4 is CH$_3$ or H; R5 is —CH$_3$, or —NH$_2$; R6 is selected from: —CH$_3$, —CH$_2$OH, —CH$_2$OCH$_3$, and —CH(OH)Me; and R7 is H.

In another form, the present invention provides a compound according to Formula 1, or a pharmaceutically acceptable salt thereof, where R is selected from —S(O)$_2$NHR4 and —NH(SO)$_2$R5. In one embodiment, R1 is H; R2 is selected from: H, —$C_{1-2}$ alkyl, —CN, —CF$_3$, —NH$_2$, —N(H)CH$_3$, —N(CH$_3$)$_2$, —OCH$_3$, —CH$_2$—O—CH$_3$, -cyclopropyl, 4-methyl piperazinyl, and morpholinyl; R3 is selected from $C_{1-2}$ alkyl, halo, —CHF$_2$, —CF$_3$, and —OCH$_3$; R4 is H or —CH$_3$ and R5 is selected from: —CH$_3$, —NH$_2$, and —NHCH$_3$. In another embodiment, R is —S(O)$_2$NHR4. Preferably, R1 is H; R2 is selected from: H, —$C_{1-2}$ alkyl, —CN, —CF$_3$, —NH$_2$, —N(H)CH$_3$, —N(CH$_3$)$_2$, —OCH$_3$, —CH$_2$—O—CH$_3$, -cyclopropyl, 4-methyl piperazinyl, and morpholinyl; R3 is selected from $C_{1-2}$ alkyl, Cl, —CHF$_2$, —CF$_3$, and —OCH$_3$; R4 is H or —CH$_3$ and R5 is selected from: —CH$_3$, —NH$_2$, and —NHCH$_3$.

In another form, the present invention provides a compound according to Formula 1, or a pharmaceutically acceptable salt thereof where R1 is H. Preferably X is CH or N; A is N; L is a —$C_{1-3}$alkyl; R is selected from: —S(O)$_2$NHR4, —NHS(O)$_2$R5, and —NHC(O)—R6; R1 is H or Cl; R2 is selected from: H, —$C_{1-2}$ alkyl, —CN, —CF$_3$, —NH$_2$, —N(H)CH$_3$, —N(CH$_3$)$_2$, —OCH$_3$, —CH$_2$—O—CH$_3$, -cyclopropyl, 4-methyl piperazinyl, and morpholinyl; R3 is selected from $C_{1-2}$ alkyl, Cl, —CHF$_2$, —CF$_3$, and —OCH$_3$; R4 is H or —CH$_3$; R5 is selected from: —CH$_3$, —NH$_2$, and —NHCH$_3$; R6 is selected from: —CH$_3$, —CH$_2$OH, —CH$_2$OCH$_3$, —CH(OH)CH$_3$, —NH$_2$, and —NHCH$_3$; R7 is H or —CH$_3$.

The present invention provides a compound according to Formula 1, or a pharmaceutically acceptable salt thereof where R2 is selected from H, —$C_{1-2}$ alkyl, —CN, —CF$_3$, —NH$_2$, —N(H)CH$_3$, —N(CH$_3$)$_2$, 4-methyl piperazinyl, and morpholinyl; and where A, X, L, R, R1, R3-7 are as provided above. Preferable R2 is selected from H, —CH$_3$, —NH$_2$, —N(H)CH$_3$, —N(CH$_3$)$_2$, 4-methyl piperazinyl, and morpholinyl. R is —S(O)$_2$NHR4, or —NHS(O)$_2$R5; R1 is H; R3 is selected from $C_{1-2}$ alkyl, or Cl; R4 is H or —CH$_3$; and R5 is selected from: —CH$_3$, —NH$_2$, and —NHCH$_3$. More preferably R2 is selected from: H, —CH$_3$, —NH$_2$, and 4-methyl piperazinyl.

The present invention provides a compound according to Formula 1, or a pharmaceutically acceptable salt thereof, where R3 is selected from: $C_{1-2}$ alkyl, and Cl; and where A, X, L, R, R1, R2, and R4-7 are as provided above. In one embodiment R3 is a $C_{1-2}$ alkyl, L is —CH$_2$CH$_2$—; R is —NH(SO)$_2$R5; R1 is H; R5 is —CH$_3$, or —NH$_2$. In another embodiment, R3 is Cl; L is —CH$_2$—; R is S(O)$_2$NHR4; R1 is H, and R4 is H or CH$_3$.

The present invention provides a compound according to Formula 1, or a pharmaceutically acceptable salt thereof, where R4 is —CH$_3$ and A, X, L, R, R1-3, and are as provided above. Preferably A and X are both N. R is —S(O)$_2$NHR4. R1 is H. R2 is selected from H, —$C_{1-2}$ alkyl, —CN, —CF$_3$, —NH$_2$, —N(H)CH$_3$, —N(CH$_3$)$_2$, 4-methyl piperazinyl, and morpholinyl; preferably, R2 is selected from H, —CH$_3$, —NH$_2$, —N(H)CH$_3$, —N(CH$_3$)$_2$, 4-methyl piperazinyl, and morpholinyl; still more preferably, R2 is selected from: H, —CH$_3$, —NH$_2$, and 4-methyl piperazinyl. R3 is selected from: $C_{1-2}$ alkyl, and Cl.

The present invention provides a compound according to Formula 1, or a pharmaceutically acceptable salt thereof, where R4 is H; and A, X, L, R, and R1-3 are as provided above. Preferably A and X are both N; R is —S(O)$_2$NHR4 and R1 is H.

The present invention also provides a compound according to Formula 1, or a pharmaceutically acceptable salt thereof, where R is —NHS(O)$_2$R5 and R5 is —CH$_3$, or —NH$_2$. Preferably R5 is —CH$_3$.

The present invention also provides a compound according to Formula 1, or a pharmaceutically acceptable salt thereof where R is —NHC(O)—R6 and R6 is selected from: —CH$_3$, —CH$_2$OH, —CH$_2$OCH$_3$, —CH(OH)Me. Preferable R6 is selected from: —CH$_3$.

The present invention also provides a pharmaceutical composition comprising a compound of Formula 1 as described above, and at least one of a pharmaceutically acceptable carrier, diluent, or excipient.

The present invention also provides a compound of Formula 2 which is:

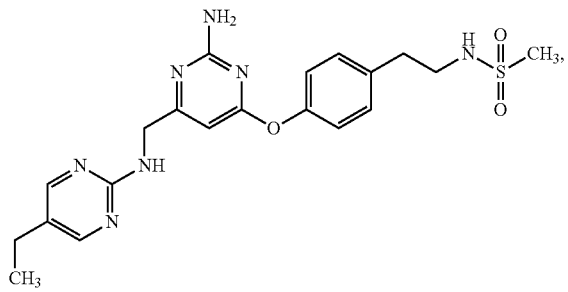

or a pharmaceutically acceptable salt thereof. In one embodiment, the compound of Formula 2 is provided as a neutral compound.

The present invention also provides a pharmaceutical composition comprising a compound of Formula 2 as described above, and at least one of a pharmaceutically acceptable carrier, diluent, or excipient.

The present invention also provides a compound of Formula 3 which is:

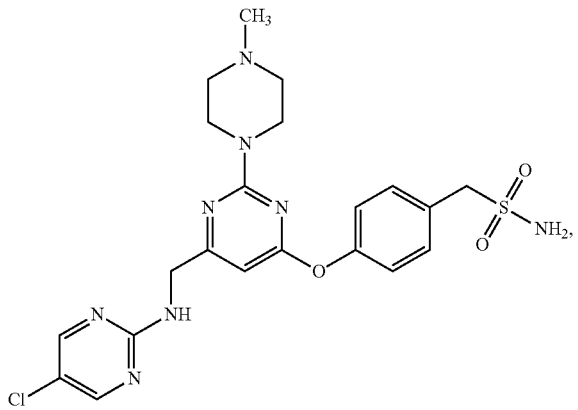

or a pharmaceutically acceptable salt thereof. In one embodiment, the compound of Formula 3 is provided as a neutral compound.

The present invention also provides a pharmaceutical composition comprising a compound of Formula 3 as described above, and at least one of a pharmaceutically acceptable carrier, diluent, or excipient.

The present invention also provides a method of treating a patient in need of treatment for cardiovascular disease, dyslipidemia, atherosclerosis, or hypertriglyceridemia, the method comprises administering to the patient an effective amount of a compound according to Formula 1, or a pharmaceutically acceptable salt thereof, as described above.

The present invention also provides a method of treating a patient in need of treatment for cardiovascular disease, dyslipidemia, atherosclerosis, or hypertriglyceridemia, the method comprises administering to the patient an effective amount of a compound according to Formula 2, or a pharmaceutically acceptable salt thereof, as described above.

The present invention also provides a method of treating a patient in need of treatment for cardiovascular disease, dyslipidemia, atherosclerosis, or hypertriglyceridemia, the method comprises administering to the patient an effective amount of a compound according to Formula 3, or a pharmaceutically acceptable salt thereof, as described above.

The present invention also provides method of treating a patient in need of treatment for cardiovascular disease, dyslipidemia, atherosclerosis, or hypertriglyceridemia, the method comprises administering to the patient an effective amount of a pharmaceutical composition comprising a compound according to any one of Formulae 1-3 as described above.

The present invention also provides a compound according to any one of Formulae 1-3 for use in therapy.

The present invention also provides a compound, according to any one of Formulae 1-3 for use in the treatment of cardiovascular disease, dyslipidemia, atherosclerosis, or hypertriglyceridemia. In one embodiment, the compound of one of Formulae 1-3 as described above is for use in the treatment of cardiovascular disease. In another embodiment, the compound of one of Formulae 1-3 as described above is for use in the treatment of dyslipidemia. In still another embodiment, the compound of one of Formulae 1-3 as described above is for use in the treatment of hypertriglyceridemia.

The present invention also provides the use of a compound according to any one of Formulae 1-3, or a pharmaceutically acceptable salt thereof, as described above in the manufacture of a medicament. In one embodiment the present invention provides for the use of a compound according to any one of Formulae 1-3, or a pharmaceutically acceptable salt thereof, as described above, in the manufacture of a medicament to treat cardiovascular disease, dyslipidemia, atherosclerosis, or hypertriglyceridemia.

In the preparations described herein the amine can be protected to facilitate the synthesis of the intermediates (Preparations) and Examples. Various amine protecting functionalities are known and include: carbamates such as $C_{1-5}$ alkyl carbamate, $C_{3-6}$ cycloalkyl carbamate, preferably a t-butyl carbamate, (BOC) or benzyl carbamate (CBZ); amides such as $C_{1-3}$ alkylamide, $C_{1-3}$ haloalkylamide, formamide or acetamide chloroacetamide, trifluoridoacetamide; and benzyl amines. Additional examples of amine protecting functionalities, methods of preparing the protected amines, and methods for deprotecting the protected amine can be found in "Protecting Groups in Organic Synthesis", 3rd Ed. Greene, T. W., Wuts, P. G. M., Eds., John Wiley and Sons, New York, 1999. In other functional groups that can be readily converted to the amino group can also be used. Such functional groups, preparations, and transformations of these groups can be found in "Comprehensive Organic Transformations: A Guide to Functional Group Preparations" by Larock. R. C, Wiley VCH, 1999 and in "March's Advanced Organic Chemistry, Reactions, Mechanisms and Structure" Smith, M. B., and March, J., Wiley-Interscience, 6th Ed. 2007.

The term "pharmaceutically-acceptable salt", as used herein refers, a salt of a compound of the invention considered to be acceptable for clinical and/or veterinary use. Pharmaceutically acceptable salts and common methodologies for preparing them are can be found in "Handbook of Pharmaceutical Salts: Properties, Selection and Use", by P. Stahl, VCHA/Wiley-VCH, 2002); and in S. M. Berge, et al., "Pharmaceutical Salts," *Journal of Pharmaceutical Sciences*, Vol. 66, No. 1, January 1977.

The pharmaceutical composition for the present invention may be prepared by known procedures using readily available ingredients. The term "pharmaceutically acceptable" as used herein refers to one or more carriers, diluents, and excipients that are compatible with the other ingredients in the formulation and not deleterious to the patient. Examples of pharmaceutical compositions and processes for their preparation can be found in Remington, "The Science and Practice of Pharmacy" (A. Gennaro, et al. eds. 19$^{th}$ ed. Mack Publishing Co.) Non-limiting examples of pharmaceutically acceptable carriers and diluents include the following: starch, sugars, mannitol, and silica derivatives; binding agents such as carboxymethyl cellulose and other cellulose derivatives, alginates, gelatin, and polyvinyl-pyrrolidone; kaolin and bentonite; polyethyl glycols.

Preferred pharmaceutical compositions can be formulated as a tablet, capsule or solution for oral administration or an injectable solution. The tablet, capsule or solution can include a compound of the present invention in an amount effective for treating a patient in need of treatment, preferably, for the treatment of cardiovascular diseases, dyslipidemia, atherosclerosis, or hypertriglyceridemia.

As used herein, the term "effective amount" refers to an amount that is a dosage, which is effective in treating a disorder, such as cardiovascular disease, dyslipidemia, atherosclerosis, or hypertriglyceridemia. The attending physician, veterinarian, or diagnostician can determine an effective amount of a compound of the invention to treat a patient. In determining an effective amount or dose of the compound, a number of factors are considered, including, but not limited to which of the compounds, or its salt, will be administered; the co-administration of other agents, if used; the species of mammal; its size, age, and general health; the degree of involvement or the severity of the disorder, the response of the individual patient; the mode of administration; the bioavailability characteristics of the preparation administered; the dose regimen selected; the use of other concomitant medication; and other relevant circumstances.

As used herein, the terms "treating", "to treat", or "treatment", include restraining, slowing, stopping, reducing, or reversing the progression or severity of an existing symptom, disorder, condition, or disease, which can include treating cardiovascular diseases, dyslipidemia, atherosclerosis, and hypertriglyceridemia. Treatment, as used herein, can also include reducing the risks of major cardiovascular events such as heart attacks and strokes.

As used herein, the term "patient" refers to a mammal, preferably a human or companion mammal, such as, a dog or cat or a domesticated animal, such as a cow, pig, horse, sheep and goat.

A compound of the present invention can be used alone or combined with one or more additional therapeutic agents. For example a compound of the invention can be combined with additional therapeutic agents used to treat cardiovascular diseases such as: niacin, aspirin, statins, CETP inhibitors, and fibrates. Examples of statins include atorvastatin, cerivastatin, fluvastatin, lovastatin, mevastatin, pitavastatin, pravastatin, rosuvastatin, and simvastatin. Examples of fibrates include bezafibrate, ciprofibrate, clofibrate, gemfibrozil, and fenofibrate.

The exemplified compounds and the additional therapeutic agent(s) can be administered either together by the same delivery route and device such as a single pill, capsule, tablet, or solution; or separately administered either at the same time in separate delivery devices or sequentially.

GENERAL CHEMISTRY

As used herein, the following terms have the meanings indicated: "DMF" refers to dimethylformamide; "DMSO" refers to dimethylsulfoxide; "EtOH" refers to ethanol; "HPLC" refers to high performance liquid chromatography; "hr" or "hrs" refers to hour or hours; "LCMS" refers to liquid chromatography mass spectrometry; "min" refers to minutes; "MeOH" refers to methanol; "MS" refers to mass spectroscopy; "RT" refers to room temperature; and "SD" refers to standard deviation.

The compounds of the present invention, or salts thereof, may be prepared by a variety of procedures known in the art, some of which are illustrated in the Schemes, Preparations, and Examples below. The specific synthetic steps for each of the routes may be combined in different ways, or in conjunction with steps from different schemes, to prepare compounds or salts of the present invention. The products of each step in the Schemes below can be recovered by conventional methods well known in the art, including extraction, evaporation, precipitation, chromatography, filtration, trituration, and crystallization. In the Schemes below, all substituents unless otherwise indicated, are as previously defined. The reagents and starting materials are readily available to one of ordinary skill in the art.

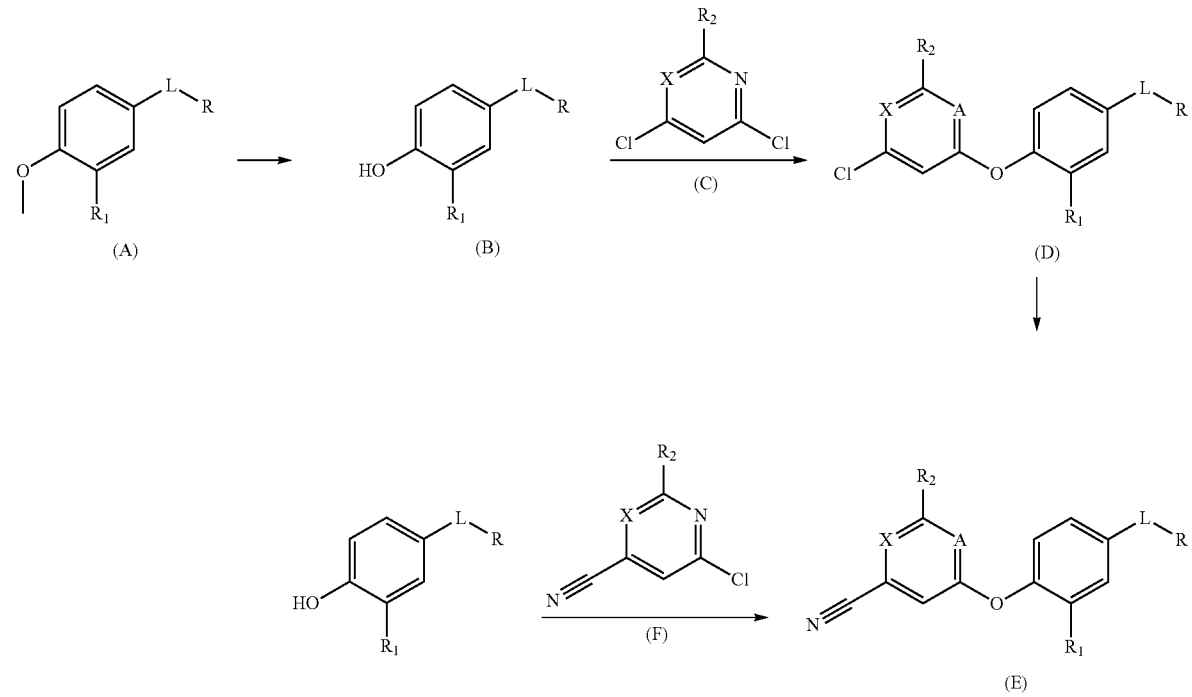

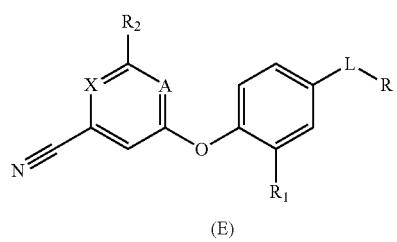

(E)

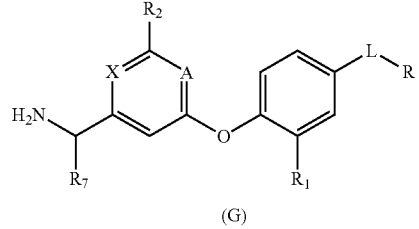

(G)

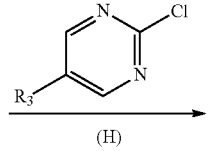

(H)

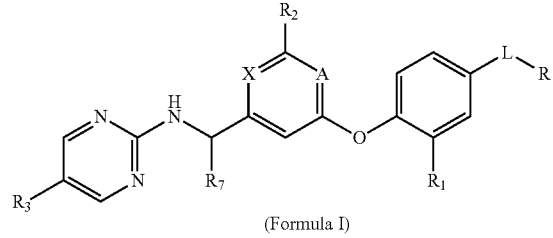

(Formula I)

Scheme 2

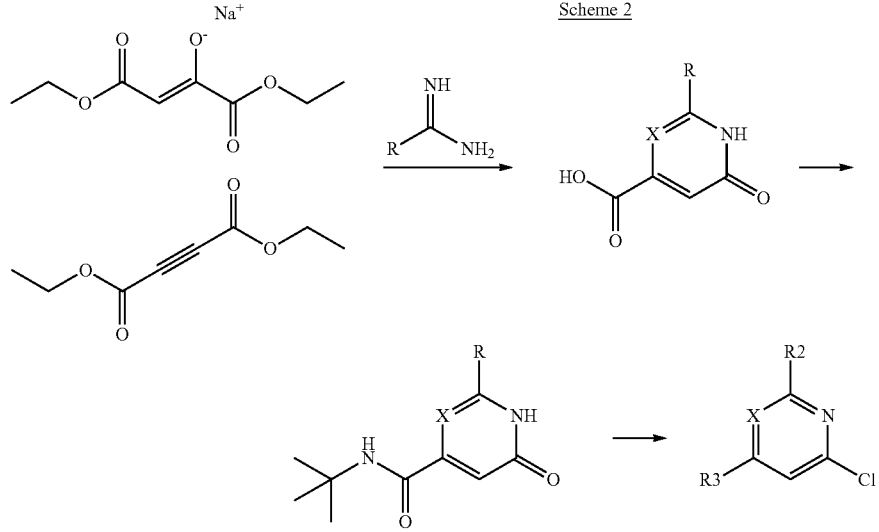

In Scheme 1, Phenol (B) may be prepared by cleavage of aromatic ether (A). Phenol (B) can be coupled with an appropriately substituted pyridine or pyrimidine, (C), which may be purchased or prepared, for instance by the method depicted in Scheme (2), to provide compound (D). Compound (E) may be obtained by cyanation of (D). Alternatively, compound (E) may be obtained directly by coupling phenol (B) with compound (F), which already contains the nitrile substituent. In a further reaction, compound (G) may be prepared through reduction of the nitrile group in compound (E). A nucleophilic aromatic substitution reaction between compound (G) and pyrimidine (H) may provide a compound of Formula I.

Alternative preparations are illustrated in Schemes 3 and 4.

Scheme 3

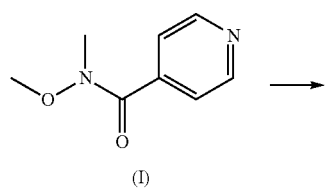

(I)

-continued

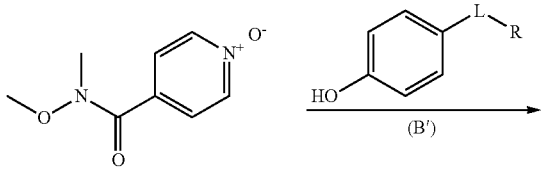

(J) (B')

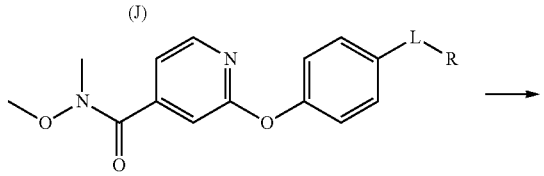

(K)

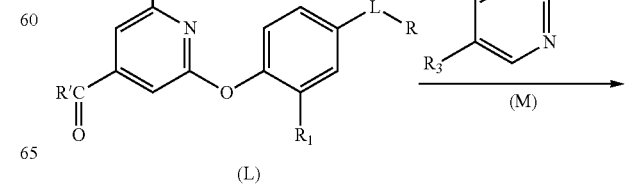

(L) (M)

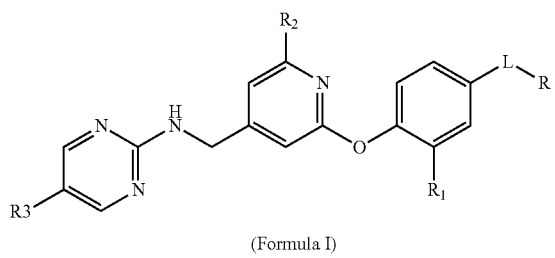

(Formula I)

In Scheme 3, the Weinreb amide, (1) may be oxidized to the N-oxide (J). N oxide (J) may be coupled with phenol (B') utilizing suitable coupling reagent and a suitable amine base such as diisopropyl ethylamine (DIPEA) or trimethylamine. The resulting compound (K) may be converted to (L) either a ketone (R'=alkyl) or an aldehyde (R'=H), which in turn may undergo reductive amination by compound (M) to result in a compound of Formula I.

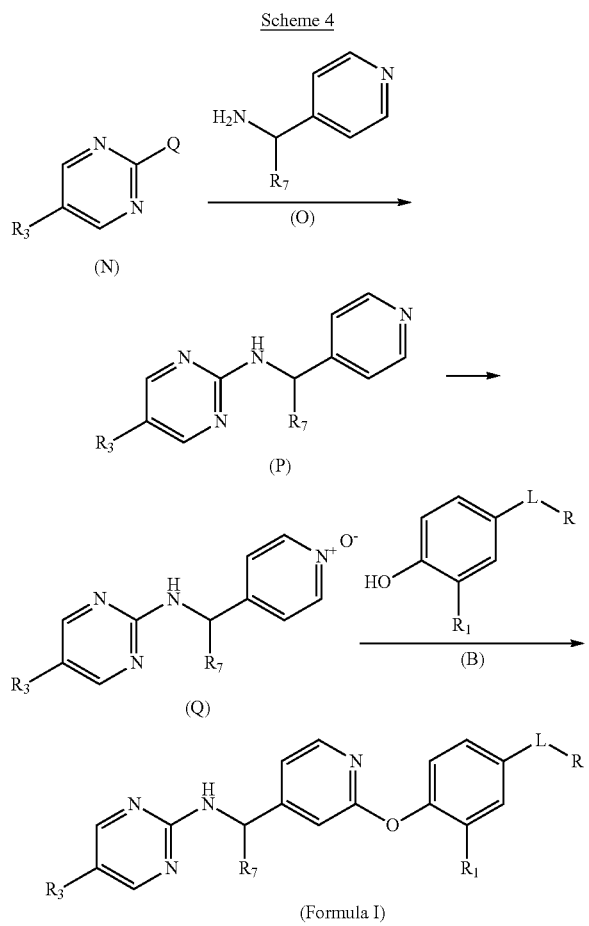

In Scheme 4, compound (P) is prepared by reacting an appropriately substituted compound (N, where substituent Q is a halogen), with amine (O). Compound (P) may then be oxidized to the N-Oxide compound (Q). Coupling N-oxide (Q) with compound (B) under coupling conditions similar to those described in Scheme 3 results in a compound of Formula I.

Preparation 1

2-(4-Methoxyphenyl)-N-methyl-ethanesulfonamide

Combine sodium 2-(4-methoxyphenyl)-ethanesulfonate (3.5 g, 14.7 mmol), dimethylformamide (2 mL) and thionyl chloride (32.1 mL, 440 mmol). Heat the mixture to 100° C. for 2 hours. Remove excess thionyl chloride under reduced pressure, add tetrahydrofuran (30 mL) followed by monomethylamine (29 mL, 59 mmol), and stir the resulting mixture at ambient temperature for 30 minutes. Add water, then extract with ethyl acetate. Wash the ethyl acetate extracts with water and brine. Dry over $Na_2SO_4$, filter, collect the filtrate then remove volatile solvents under reduced pressure. Subject the residue to silica gel chromatography eluting with a gradient of 0-100% ethyl acetate in hexanes. Combine the appropriate fractions and remove the solvents under reduced pressure to provide the title compound (1.1 g, 28%). MS (m/z): 230 (M+1).

Preparation 2

2-(4-Hydroxyphenyl)-N-methyl-ethanesulfonamide

Dissolve 2-(4-methoxyphenyl)-N-methyl-ethanesulfonamide (1.1 g, 4.08 mmol) in dichloromethane (16.3 mL). Cool the mixture to −78° C. and stir for 5 minutes. Add boron tribromide (5.1 g, 20 mmol) drop-wise while stirring. Remove the cooling bath, allow the mixture to warm to ambient temperature, and stir for 2 hours. Quench the mixture with 5:1 dichloromethane/ethanol and stir for 5 minutes. Remove the solvents under reduced pressure to provide a residue. Dissolve the residue in ethyl acetate. Wash the ethyl acetate mixture with water then brine. Dry the resulting solution over $Na_2SO_4$, filter, collect the filtrate and remove the solvents under reduced pressure to provide the title compound as a purple solid. (1.04 g, 94.8%). MS (m/z): 216 (M+1).

Preparation 3 tert-Butyl N-[2-(4-hydroxyphenyl)-1-methyl-ethyl] carbamate

Combine 4-(2-aminopropyl)phenol (2.17 g, 9.35 mmol) and triethylamine (6.52 mL, 46.7 mmol) in dichloromethane (38 mL). Add di-tert-butyldicarbonate (2.04 g, 9.35 mmol) and stir the mixture at ambient temperature for 2 hours. Remove solvents under reduced pressure, add water, and extract with ethyl acetate. Combine the ethyl acetate extracts, dry over $MgSO_4$, filter, and collect the filtrate. Remove the solvents under reduced pressure to give the title compound (2.2 g, 90%) as colorless oil. MS (m/z): 196 (M−55).

Preparation 4

1-(3-Fluoro-4-hydroxy-phenyl)-N-methyl-methanesulfonamide

Combine 1-(4-hydroxyphenyl)-N-methyl-methanesulfonamide (670 mg, 3.13 mmol), methanol (12.7 mL) and 1-chloromethyl-4-fluoro-1,4-diazoniabicyclo [2.2.2]octane bis(tetrafluoroborate) (1.16 g, 3.29 mmol). Warm the mixture to 80° C. for 17 hours. Add fresh 1-chloromethyl-4-fluoro-1,4-diazoniabicyclo[2.2.2]octane bis(tetrafluoroborate) (277 mg, 0.782 mmol) and warm to 80° C. for an additional 6 hours. Add fresh 1-chloromethyl-4-fluoro-1,4-diazoniabicyclo[2.2.2]octane bis(tetrafluoroborate) (277 mg, 0.782 mmol) and warm the mixture to 80° C. for an additional 17 hours. Filter the result mixture to remove a white solid; rinse the solid with methanol. Collect and concentrate the filtrate under reduced pressure to provide a brown residue. Isolate the product via reverse phase chromatography eluting with a gradient of 10-100% acetonitrile with 0.1% trifluoroacetic acid and 0.1% trifluoroacetic acid/H$_2$O. Combine the appropriate fractions and remove the solvents under reduced pressure to provide the title compound (0.28 g, 37%). MS (m/z): 242 (M+23).

Preparation 5

2-Methylsulfanyl-6-oxo-1H-pyrimidine-4-carboxylic acid

Add sodium diethyl oxalacetate (34.55 g, 156.2 mmol) to H$_2$O (170 mL). Add sodium hydroxide (2N, 117.1 mL, 234.3 mmol) followed by 2-methylthiopseudourea sulfate (15 g, 156.2 mmol) and stir the mixture for 2 hours at ambient temperature. Cool to 0° C. and add HCl aq. (12N, 19.57 mL, 234.3 mmol) drop-wise. Isolate the white precipitate via filtration, wash the filter cake with water and methyl tert-butyl ether, then air dry to provide the title product as a white solid (11.1 g, 75%). MS (m/z): 187 (M+1).

Preparation 6

6-Oxo-1H-pyrimidine-4-carboxamide

Dissolve diethyl but-2-ynedioate (26.0 g, 148 mmol) in acetonitrile (400 mL). Add formamidine hydrochloride (11.9 g, 148 mmol) and triethylamine (20.6 mL, 148 mmol) to the mixture. Reflux the mixture while stirring for 3 days. Remove the solvent under reduced pressure. Re-suspend the residue in ammonia (7M in methanol) (300 mL, 2.10 moles) and stir overnight at ambient temperature. Cool the mixture in an ice bath and filter. Wash the filter cake with methanol, water, and methyl tert-butyl ether, then air dry the solid to provide the title compound (6.76 g, 33%). MS (m/z): 140 (M+1).

Preparation 7

N-tert-Butyl-2-chloro-6-methyl-pyridine-4-carboxamide

Add 2-chloro-6-methylpyridine-4-carboxylic acid (1.0 g, 5.8 mmol) to dichloromethane (20 mL) and cool the mixture to 0° C. Add triethylamine (1.2 ml, 8.7 mmol) and stir the mixture for 15 min. Add tert-butyl chloroformate (1M, 7.1 mL, 7.1 mmol) drop-wise over 10 minutes. Cool the mixture to −10° C. and stir for 45 minutes. Add isopropyl amine (511 mg, 6.99 mol), and then warm the mixture to ambient temperature. Monitor the reaction via LCMS. After the reactions is complete, concentrate the mixture under reduced pressure and then dissolve the residue in ethyl acetate. Wash with saturated aqueous citric acid, saturated aqueous sodium bicarbonate, brine, and dry over MgSO$_4$. Filter and concentrate the filtrate under reduced pressure to provide the title compound as a brown oil (1.21 g, 91.6%). MS (m/z): 227 (M+1).

Preparation 8

N-tert-Butyl-2-methylsulfanyl-6-oxo-1H-pyrimidine-4-carboxamide

Prepare the compound of Preparation 8 essentially by the method of Preparation 7 using the appropriately substituted pyrimidin-4-one compound and an appropriate amide coupling reagent. MS (m/z): 242 (M+1).

Preparation 9

2-Chloro-6-methyl-pyridine-4-carbonitrile

Add N-tert-butyl-2-chloro-6-methyl-pyridine-4-carboxamide (92.4 g, 375 mmol) to toluene (680 mL). Add phosphoryl chloride (76.7 mL, 325 mmol) and heat the mixture with stirring to 100° C. Stir the reaction at 100° C. for 20 hours, then add additional phosphoryl chloride (17.4 mL, 188 mmol). Maintain the reaction temperature at 100° C. while stirring for an additional 8 hours. Cool the mixture to ambient temperature and pour it into a 20% aqueous potassium phosphate (dibasic) solution, which has been previously cooled in an ice bath. Stir the mixture for 2 hours, separate the layers, extract the aqueous layer with toluene, combine the organic extracts, dry over MgSO$_4$, filter, collect the filtrate, and concentrate the filtrate under reduced pressure to provide the title compound (47.7 g, 84%). $^1$H NMR (400.13 MHz, DMSO-d6): 7.94 (s, 1H), 7.80 (s, 1H), 2.52 (s, 3H).

Preparation 10

6-Chloro-2-methylsulfanyl-pyrimidine-4-carbonitrile

Prepare the compound of preparation 10 essentially by the method of Preparation 9 using an appropriately substituted pyrimidine. MS (m/z): 186 (M+1).

Preparation 11

[4-[(4-Cyano-2-pyridyl)oxy]phenyl]methanesulfonamide

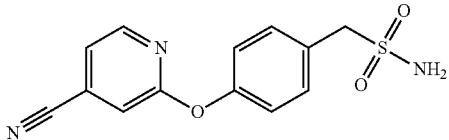 [SMILES: N#Cc1ccnc(Oc2ccc(CS(N)(=O)=O)cc2)c1]

Dissolve 2-fluoropyridine-4-carbonitrile (5.2 g, 43 mmol) in dimethylformamide (78 mL). Add (4-hydroxyphenyl)methanesulfonamide (7.3 g, 39. mmol), diisopropylethylamine (10.2 mL, 58.5 mmol) and potassium carbonate (10.8 g, 78 mmol) to the solution. Heat the mixture to 75° C. and stir for 17 hours. Dilute the reaction with water and extract with ethyl acetate. Combine the ethyl acetate extracts and wash with brine, dry over MgSO$_4$, filter, collect the filtrate, and concentrate the filtrate under reduced pressure to give a solid. Subject the solid to silica gel chromatography eluting with a gradient of 50-100% ethyl acetate in hexanes. Combine the appropriate fractions and remove the solvents under reduced pressure to provide the title compound as a white solid (5.8 g, 51%). MS (m/z): 290 (M+1).

TABLE 1

Prepare the following compounds essentially according to Preparation 11 using the appropriately substituted pyridine or pyrimidine.

| Prep. No. | Chemical name | Structure and Physical Data MS (m/z) |
|---|---|---|
| 12 | [4-[(6-Chloro-4-cyano-2-pyridyl)oxy]phenyl]methanesulfonamide | 341 (M + H₂O) |
| 13 | 1-[4-[(6-Chloro-4-cyano-2-pyridyl)oxy]phenyl]-N-methyl-methanesulfonamide | 336 (M − 1) |
| 14 | 1-[4-[(4-Cyano-2-pyridyl)oxy]-3-fluoro-phenyl]-N-methyl-methanesulfonamide | 322 (M + 1). |
| 15 | 1-[4-[(4-Cyano-2-pyridyl)oxy]phenyl]-N-methyl-methanesulfonamide | 304 (M + 1) |
| 16 | tert-Butyl N-[2-[4-[(4-cyano-2-pyridyl)oxy]phenyl]ethyl]carbamate | 304 (M + 1). |
| 17 | tert-Butyl N-[2-[4-[(6-chloro-4-cyano-2-pyridyl)oxy]phenyl]ethyl]carbamate | 74 (M + 1) |
| 18 | [4-[(2-Cyano-4-pyridyl)oxyiphenyl]methanesulfonamide | 290 (M + 1) |
| 19 | 1-[4-[(2-Cyano-4-pyridyl)oxy]phenyl]-N-methyl-methanesulfonamide | 304 (M + 1) |

TABLE 1-continued

Prepare the following compounds essentially according to Preparation 11 using the appropriately substituted pyridine or pyrimidine.

| Prep. No. | Chemical name | Structure and Physical Data MS (m/z) |
|---|---|---|
| 20 | [4-[(4-Cyano-2-pyridyl)oxy]-3-fluorophenyl]methanesulfonamide | 308 (M + 1) |
| 21 | tert-Butyl N-[[4-[(4-cyano-6-methyl-2-pyridyl)oxy]phenyl]methyl]carbamate | 284 (M − 55) |
| 22 | tert-Butyl N-[2-[4-[(6-chloro-4-cyano-2-pyridypoxylphenyl]-1-methyl-ethyl]carbainate | 332 (M − 55) |
| 23 | 1-[4-(6-Chloro-2-ethyl-pyrimidin-4-yl)oxyphenyl]-N-methyl-methanesulfonamide | 342 (M + 1) |
| 24 | 1-[4-[6-Chloro-2-(trifluoromethyl)pyrimidin-4-yl[oxyphenyl]-N-methyl-methanesulfonamide | 382 (M + 1) |
| 25 | 1-[4-[6-Chloro-2-(methoxymethyl)pyrimidin-4-yl]oxyphenyl]-N-methyl-methanesulfonamide | 358 (M + 1) |
| 26 | tert-Butyl N-[2-[4-(6-cyanopyrimidin-4-yl)oxyphenyl]ethyl]carbamate | 285 (M − 55) |

TABLE 1-continued

Prepare the following compounds essentially according to Preparation 11 using the appropriately substituted pyridine or pyrimidine.

| Prep. No. | Chemical name | Structure and Physical Data MS (m/z) |
|---|---|---|
| 27 | 1-[4-(6-Cyano-2-methylsulfanyl-pyrimidin-4-yl)oxyphenyl]-N-methyl-methanesulfonamide | 351 (M + 1) |
| 28 | [4-(6-Cyano-2-methylsulfanyl-pyrimidin-4-yl)oxyphenyl]methanesulfonamide | 337 (M + 1) |
| 29 | [4-(6-Chloro-2-methyl-pyrimidin-4-yl)oxyphenyl]methanesulfonamide | 314 (M + 1) |
| 30 | tert-Butyl N-[2-[4-(2-amino-6-chloro-pyrimidin-4-yl)oxyphenyl]ethyl]carbannate | 365 (M + 1) |
| 31 | 1-[4-(6-Chloro-2-methoxy-pyrimidin-4-yl)oxyphenyl]-N-methyl-methanesulfonamide | 344 (M + 1) |
| 32 | 1-[4-(6-Chloro-2-cyclopropyl-pyrimidin-4-yl)oxyphenyl]-N-rnethyl-methanesulfonamide | 354 (M + 1) |
| 33 | N-[2-[4-(2-Chloro-6-cyano-pyrimidin-4-yl)oxyphenyl]ethyl]acetarnide | 317 (M + 1) |

TABLE 1-continued

Prepare the following compounds essentially according to Preparation 11 using the appropriately substituted pyridine or pyrimidine.

| Prep. No. | Chemical name | Structure and Physical Data MS (m/z) |
|---|---|---|
| 34 | [4-(2-Chloro-6-cyano-pyrimidin-4-yl)oxyphenyl]methanesulfonamide | 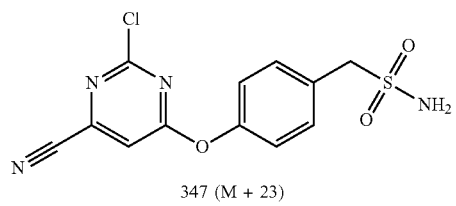 347 (M + 23) |
| 35 | N-[2-[4-(2-Chloro-6-cyano-pyrimidin-4-yl)oxyphenyl]ethyl]methanesulfonamide | 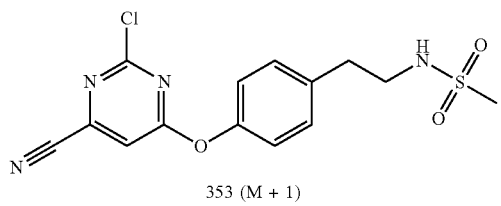 353 (M + 1) |
| 36 | tert-Butyl N-[2-[4-(6-cyano-2-methyl-pyrimidin-4-yl)oxyphenyl]ethyl]carbamate | 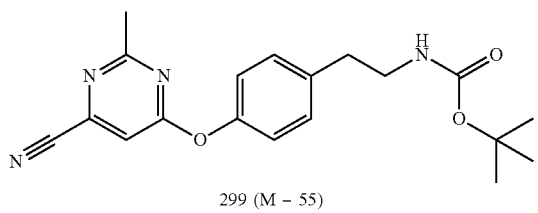 299 (M − 55) |
| 37 | 1-[4-(6-Chloro-2-methyl-pyrimidin-4-yl)oxyphenyl]-N-methyl-methanesulfonamide | 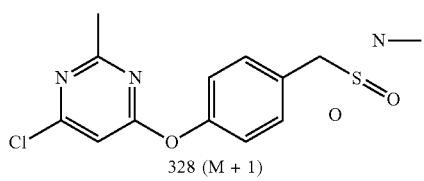 328 (M + 1) |
| 37A | tert-Butyl 4-[4-cyano-6-[4-(sulfamoylmethyl)phenoxy]pyrimidin-2-yl]piperazine-1-carboxylate | 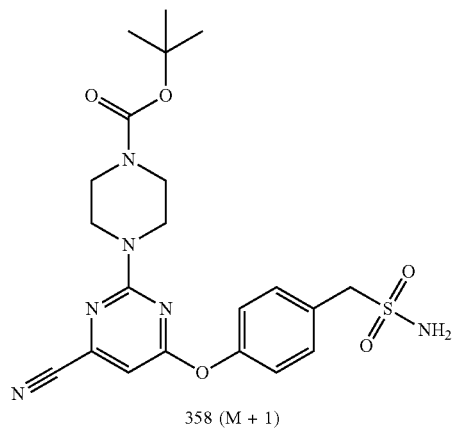 358 (M + 1) |

Preparation 37B

[4-(2,6-Dichloropyrimidin-4-yl)oxyphenyl]methanesulfonamide

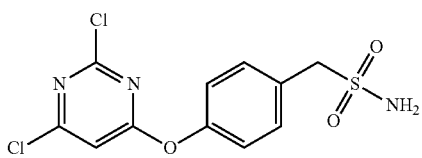 [SMILES: NS(=O)(=O)Cc1ccc(Oc2cc(Cl)nc(Cl)n2)cc1]

In duplicate procedures, dissolve 2,4,6-trichloropyrimidine (91.6 g, 0.49 mol), potassium carbonate (81 g, 0.59 mol) in DMF (700 mL). Cool to 0° C. and add drop-wise over 30 minutes a solution of (4-hydroxyphenyl)methanesulfonamide (85 g, 0.45 mol) in DMF (100 mL). Stir the suspension at ambient temperature for 1.5 hours. Combine the 2 reaction mixture for workup. Pour the combined reaction mixtures into 2 L of water and extract with ethyl acetate (2×800 mL). Combine the organic extracts. Wash extracts with brine (2×300 mL), dry over $Na_2SO_4$, filter, and concentrate the filtrate under reduced pressure to give a residue. Subject the residue to flash column chromatography eluting with a gradient of petroleum ether in ethyl acetate (10:1 to 3:1). Combine the appropriate fractions and evaporate the solvent under reduced pressure to give the title compound (235 g, 77%). $^1$H NMR (CDCl$_3$): 7.50-7.52 (m, 2H), 7.10-7.30 (m, 2H), 6.87 (s, 1H), 4.74 (s, 2H), 4.3 (s, 2H).

Preparation 37C

N-[2-[4-(2,6-Dichloropyrimidin-4-yl)oxyphenyl]ethyl]methanesulfonamide

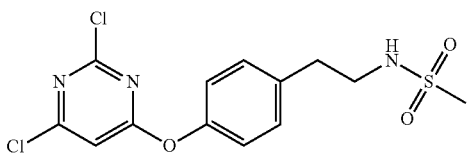 [SMILES: CS(=O)(=O)NCCc1ccc(Oc2cc(Cl)nc(Cl)n2)cc1]

Prepare the title compound essentially according to the method of Preparation 37A. $^1$H NMR (400.13 MHz, CDCl$_3$): 7.27-7.29 (m, 2H), 7.0-7.1 (m, 2H), 6.81 (s, 1H), 4.40-4.41 (m, 1H), 3.39-3.44 (m, 2H), 2.28-2.91 (m, 2H), 2.83 (s, 3H).

Preparation 38 tert-Butyl N-[[4-(6-chloro-2-methyl-pyrimidin-4-yl)oxyphenyl] methylsulfonyl]-N-methyl-carbamate

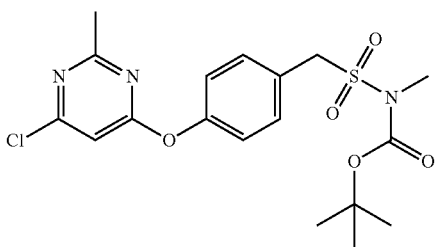 [SMILES: Cc1nc(Cl)cc(Oc2ccc(CS(=O)(=O)N(C)C(=O)OC(C)(C)C)cc2)n1]

Dissolve 1-[4-(6-chloro-2-methyl-pyrimidin-4-yl)oxyphenyl]-N-methyl-methanesulfonamide (2.41 g, 4.6 mmol) in dichloromethane (10 mL) and add N,N-dimethyl-4-pyridinamine (56.6 mg, 0.46 mmol). Cool the solution to 0° C., add tert-butoxycarbonyl tert-butyl carbonate (1.5 g, 6.8 mmol), and stir for one hour. Quench the reaction with an excess of 0.5 N HCl, extract with dichloromethane, and wash with brine. Dry the dichloromethane solution over MgSO$_4$, filter, collect the filtrate, and concentrate the filtrate under reduced pressure to provide the title compound as an orange oil (3.03 g, 99.4%). MS (m/z): 428 (M+1).

TABLE 2

Prepare the following compounds essentially by the method of Preparation 38 using an appropriately substituted pyrimidine.

| Prep. No. | Chemical name | Structure and Physical Data: MS (m/z) |
|---|---|---|
| 39 | tert-Butyl N-[[4-(6-chloro-2-ethyl-pyrimidin-4-yl)oxyphenyl] methylsulfonyl]-N-methyl-carbamate | 442 (M + 1) |

TABLE 2-continued

Prepare the following compounds essentially by the method of
Preparation 38 using an appropriately substituted pyrimidine.

| Prep. No. | Chemical name | Structure and Physical Data: MS (m/z) |
|---|---|---|
| 40 | tert-Butyl N-[[4-[6-chloro-2-(trifluoromethyl)pyrimidin-4-yl]oxyphenyl]methylsulfonyl]-N-methyl-carbamate | 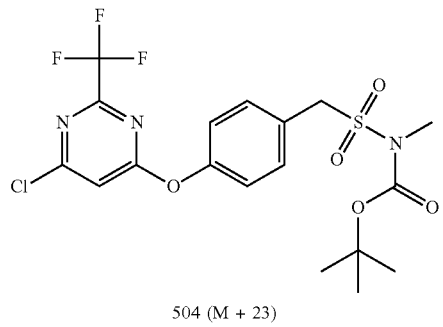<br>504 (M + 23) |
| 41 | tert-Butyl N-[[4-[6-chloro-2-(methoxymethyl)pyrimidin-4-yl]oxyphenyl]methylsulfonyl]-N-methyl-carbamate | 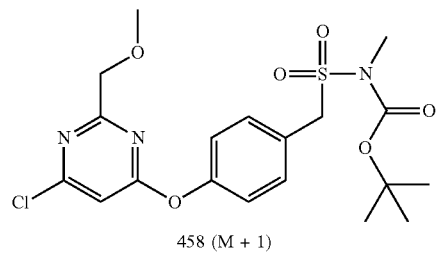<br>458 (M + 1) |
| 42 | tert-Butyl N-[[4-(6-chloro-2-methoxy-pyrimidin-4-yl)oxyphenyl]methylsulfonyl]-N-methyl-carbamate | 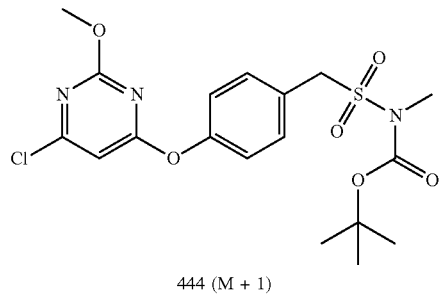<br>444 (M + 1) |
| 43 | tert-Butyl N-[[4-(6-chloro-2-cyclopropyl-pyrimidin-4-yl)oxyphenyl]methylsulfonyl]-N-methyl-carbamate | 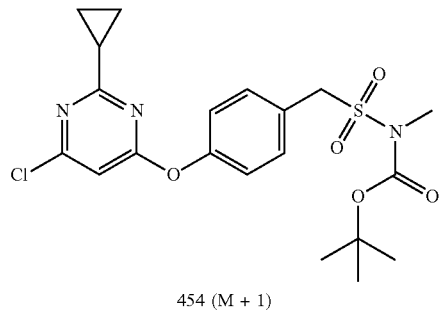<br>454 (M + 1) |

Preparation 44 tert-Butyl N-[[4-(6-cyano-2-methyl-pyrimidin-4-yl)oxyphenyl] methylsulfonyl]-N-methyl-carbamate

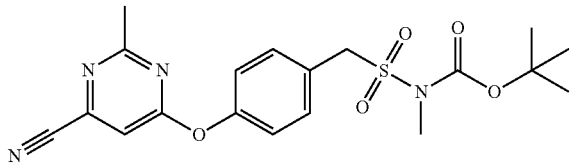 [SMILES: Cc1nc(C#N)cc(Oc2ccc(CS(=O)(=O)N(C)C(=O)OC(C)(C)C)cc2)n1]

Under an atmosphere of nitrogen, combine tert-butyl N-[[4-(6-chloro-2-methyl-pyrimidin-4-yl)oxyphenyl] methylsulfonyl]-N-methyl-carbamate (2.24 g, 3.4 mmol), dimethylformamide (2 mL), tetrakis(triphenylphosphine)palladium (1.9 g, 1.7 mmol) and zinc cyanide (2.0 g, 16.8 mmol). Heat the mixture to 90° C. and stir for 3 hours. Quench with water and sodium hydroxide then extract with ethyl acetate. Wash the ethyl acetate extracts with brine, dry over MgSO₄, filter, collect the filtrate, and concentrate the filtrate under reduced pressure to provide a residue. Subject the residue to flash column chromatography using 80 g of silica gel eluting with a 0-55% gradient of ethyl acetate in hexanes. Collect the desired fractions and remove the solvent to provide the title compound as a yellow oil (1.2 g, 80.9%). MS (m/z): 419 (M+1).

TABLE 3

Prepare the following compounds essentially according to the method of Preparation 44 using the appropriately substituted pyrimidine.

| Prep. No. | Chemical name | Structure and Physical Data: MS (m/z) |
|---|---|---|
| 45 | tert-Butyl N-[[4-(6-cyano-2-ethyl-pyrimidin-4-yl)oxyphenyl]methylsulfonyl]-N-methyl-carbamate | 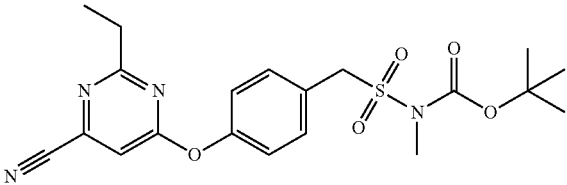 [SMILES: CCc1nc(C#N)cc(Oc2ccc(CS(=O)(=O)N(C)C(=O)OC(C)(C)C)cc2)n1] 433 (M + 1) |
| 46 | tert-Butyl N-[[4-[6-cyano-2-(trifluoromethyl)pyrimidin-4-yl]-oxyphenyl]methylsulfonyl]-N-methyl-carbamate | 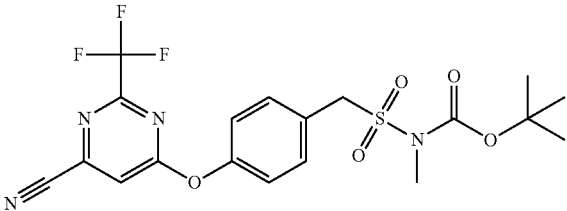 [SMILES: CN(C(=O)OC(C)(C)C)S(=O)(=O)Cc1ccc(Oc2cc(C#N)nc(C(F)(F)F)n2)cc1] 495 (M + 23) |
| 47 | tert-Butyl N-[[4-[6-cyano-2-(methoxymethyppyrimidin-4-yl]oxyphenyl]methylsulfonyl]-N-methyl-carbamate | 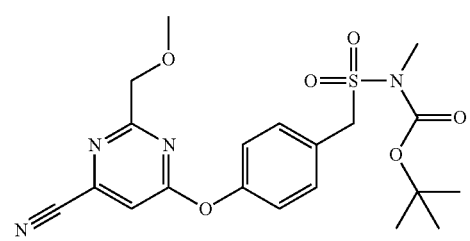 [SMILES: COCc1nc(C#N)cc(Oc2ccc(CS(=O)(=O)N(C)C(=O)OC(C)(C)C)cc2)n1] 449 (M + 1) |
| 48 | [4-(6-Cyano-2-methyl-pyrimidin-4-yl)oxyphenyl]methanestilfonamide | 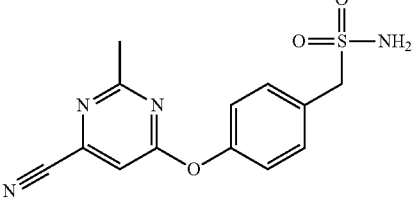 305 (M + 1) |

TABLE 3-continued

Prepare the following compounds essentially according to the method of Preparation 44 using the appropriately substituted pyrimidine.

| Prep. No. | Chemical name | Structure and Physical Data: MS (m/z) |
|---|---|---|
| 49 | tert-Butyl N-[2-[4-(2-amino-6-cyano-pyrimidin-4-yl)oxyphenyl]ethyl]carbamate | 300 (M − 55) |
| 50 | tert-Butyl N-[[4-(6-cyano-2-methoxy-pyrimidin-4-ypoxyphenyl]methylsulfonyl]-N-methyl-carbamate | 435 (M + 1) |
| 51 | tert-Butyl N-[[4-(6-cyano-2-cyclopropyl-pyrimidin-4-yl)oxyphenyl]methylsulfonyl]-N-methyl-carbamate | 445 (M + 1) |

Preparation 52

1-[4-[[4-(Aminomethyl)-6-methoxy-2-pyridyl]oxy]phenyl]-N-methyl-methanesulfonamide

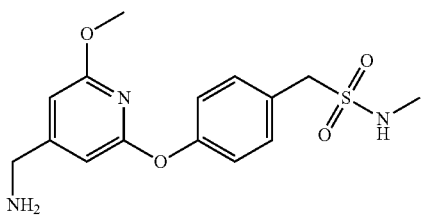 [SMILES: CNS(=O)(=O)Cc1ccc(Oc2cc(CN)cc(OC)n2)cc1]

Flush a flask with nitrogen, and charge it with 10% palladium on carbon catalyst (67 mg, 0.63 mmol). Add sufficient ethyl acetate to cover the catalyst. Add a solution of 1-[4-[[4-cyano-6-(methoxy)-2-pyridyl]oxy]phenyl]N-methyl-methanesulfonamide (0.335 g, 1.00 mmol) in ethyl acetate (50 mL), followed by methanol (25 mL), and then ammonia in methanol (25 mL 2M). Place the mixture under a balloon of $H_2$ and stir under an $H_2$ atmosphere overnight. Filter suspension through diatomaceous earth, collect the filtrate, and evaporate the solvents to provide the title compound (0.264 g, 77.9%). MS (m/z): 338 (M+1).

TABLE 4

Prepare the following compounds essentially according to the procedure for Preparation 52 using the appropriately substituted cyano compound.

| Prep. No. | Chemical name | Structure and Physical Data MS (m/z) or $H^1$ NMR |
|---|---|---|
| 53 | 1-[4-[[4-(Aminomethyl)-2-pyridyl]oxy]phenyl]-N-methyl-methanesulfonamide | 308 (M + 1) |

TABLE 4-continued

Prepare the following compounds essentially according to the procedure for Preparation 52 using the appropriately substituted cyano compound.

| Prep. No. | Chemical name | Structure and Physical Data MS (m/z) or H[1] NMR |
|---|---|---|
| 54 | 1-[4-[[4-(Aminomethyl)-6-[(4-methoxyphenyp)methylamino]-2-pyridyl]oxy]phenyl]-N-methyl-methanesulfonamide | 443 (M + 1) |
| 55 | 1-[4-[[4-(Aminomethyl)-2-pyridyl]oxy]-3-fluoro-phenyl-N-methyl-methanesulfonamide | 326 (M + 1) |
| 56 | [4-[[4-(Aminomethyl)-2-pyridyl]oxy]phenyl]methanesulfonamide | 294 (M + 1) |
| 57 | [4-[[4-(Aminomethyl)-6-[(4-methoxyphenyl)methylamino]-2-pyridyl]oxy]phenyl]methanesulfonamide | 429 (M + 1) |

TABLE 4-continued

Prepare the following compounds essentially according to the procedure for
Preparation 52 using the appropriately substituted cyano compound.

| Prep. No. | Chemical name | Structure and Physical Data MS (m/z) or H[1] NMR |
|---|---|---|
| 58 | tert-Butyl N-[2-[4-[[4-(aminomethyl)-6-[(4-methoxyphenyl)methylamino]-2-pyridyl]oxy]phenyl]ethyl]carbatnate | 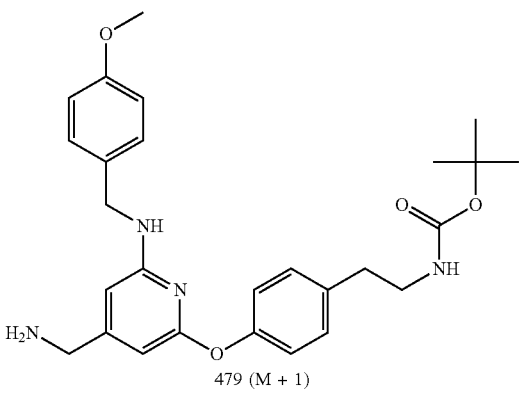 479 (M + 1) |
| 59 | [4-[[2-(Aminomethyl)-4-pyridyl]oxy]phenyl]methanesulfonamide | 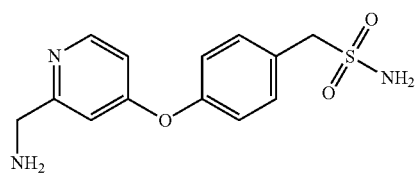 [SMILES: NCc1cc(Oc2ccc(CS(N)(=O)=O)cc2)ccn1] 294 (M + 1) |
| 60 | 1-[4-[[2-(Aminomethyl)-4-pyridyl]oxy]phenyl]-N-methyl-methanesulfonamide | 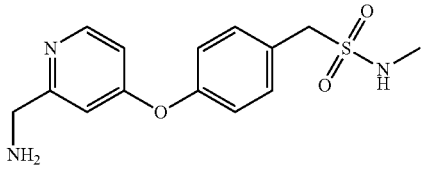 [SMILES: CNS(=O)(=O)Cc1ccc(Oc2ccnc(CN)c2)cc1] |
| 61 | tert-Butyl N-[[4-[[4-(aminomethyl)-6-methyl-2-pyridyl]oxy]phenyl]methyl]carbamate | 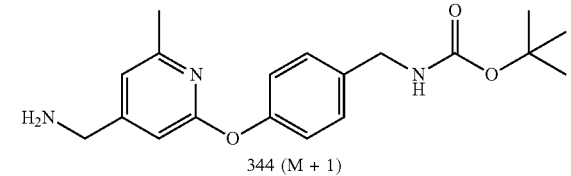 344 (M + 1) |
| 62 | tert-Butyl N-[2-[4-[[4-(aminomethyl)-6-[(4-methoxyphenyl)methylamino]-2-pyridyl]oxy]phenyl]-1-methyl-ethyl]carbamate | 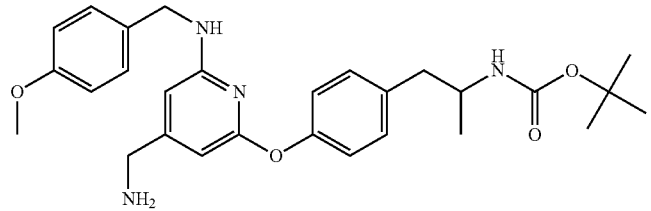 [SMILES: COc1ccc(CNc2cc(CN)cc(Oc3ccc(CC(C)NC(=O)OC(C)(C)C)cc3)n2)cc1] 493 (M + 1) |
| 63 | 1-[4-[[4-(Aminomethyl)-6-morpholino-2-pyridyl]oxy]phenyl]-N-methyl-methanesulfonamide | 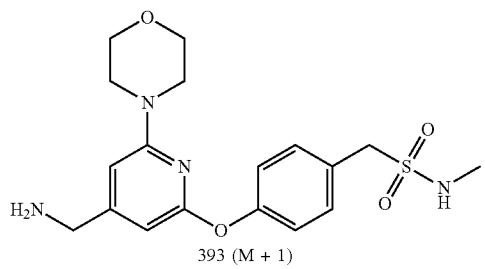 393 (M + 1) |

TABLE 4-continued

Prepare the following compounds essentially according to the procedure for
Preparation 52 using the appropriately substituted cyano compound.

| Prep. No. | Chemical name | Structure and Physical Data MS (m/z) or H¹ NMR |
|---|---|---|
| 64 | tert-Butyl N-[[4-[6-(aminomethyl)-2-ethyl-pyrimidin-4-yl]oxyphenyl]methylsulfonyl]-N-methyl-carbamate | 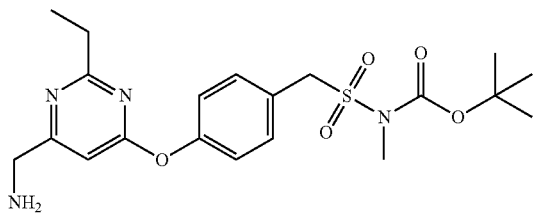 [SMILES: CCc1nc(CN)cc(Oc2ccc(CS(=O)(=O)N(C)C(=O)OC(C)(C)C)cc2)n1]<br>437 (M + 1) |
| 65 | tert-Butyl N-[[4-[6-(aminomethyl)-2-(trifluoromethyl)pyrimidin-4-yl]oxyphenyl]methylsulfonyl]-N-methyl-carbamate | 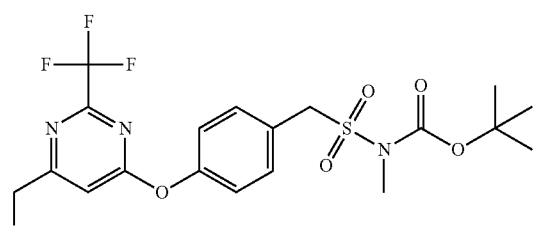<br>421 (M − 55) |
| 66 | tert-Butyl N-[[4-[6-(aminomethyl)-2-(methoxymethyl)pyrimidin-4-yl]oxyphenyl]methylsulfonyl]-N-methyl-carbamate | 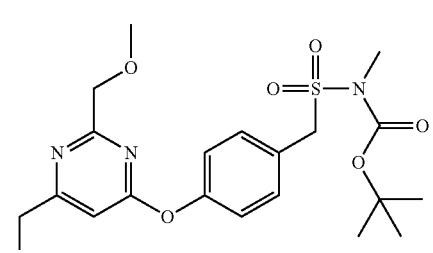<br>453 (M + 1) |
| 67 | tert-Butyl N-[2-[4-[6-(aminomethyl)pyrimidin-4-yl]oxyphenyl]ethyl]carbamate | 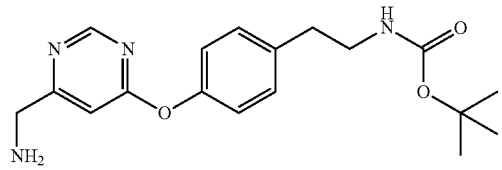 [SMILES: CC(C)(C)OC(=O)NCCc1ccc(Oc2cc(CN)ncn2)cc1]<br>345 (M + 1) |
| 68 | 1-[4-[6-(Aminomethyl)-2-methylsulfanyl-pyrimidin-4-yl]oxyphenyl]-N-methyl-methanesulfonamide | 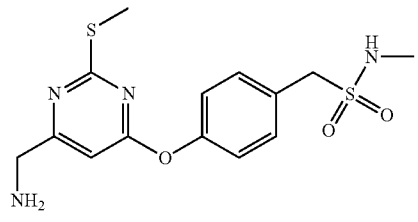 [SMILES: CNS(=O)(=O)Cc1ccc(Oc2cc(CN)nc(SC)n2)cc1]<br>355 (M + 1) |
| 69 | [4-[6-(Aminomethyl)-2-methyl-pyrimidin-4-yl]oxyphenyl]methanesulfonamide | 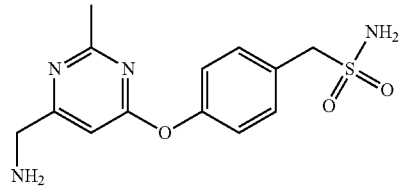 [SMILES: Cc1nc(CN)cc(Oc2ccc(CS(N)(=O)=O)cc2)n1]<br>309 (M + 1) |

TABLE 4-continued

Prepare the following compounds essentially according to the procedure for Preparation 52 using the appropriately substituted cyano compound.

| Prep. No. | Chemical name | Structure and Physical Data MS (m/z) or $H^1$ NMR |
|---|---|---|
| 70 | tert-Butyl N-[2-[4-[2-amino-6-(aminomethyl)pyrimidin-4-yl]oxyphenyl]ethyl]carbamate | 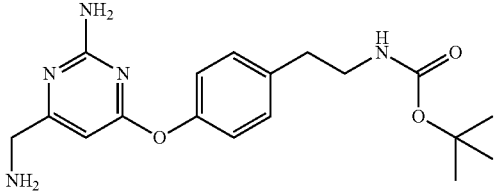 [SMILES: CC(C)(C)OC(=O)NCCc1ccc(Oc2cc(CN)nc(N)n2)cc1] 360 (M + 1) |
| 71 | tert-Butyl N-[[4-[6-(aminomethyl)-2-methoxy-pyrimidin-4-yl]oxyphenyl]methylsulfonyl]-N-methyl-carbamate | 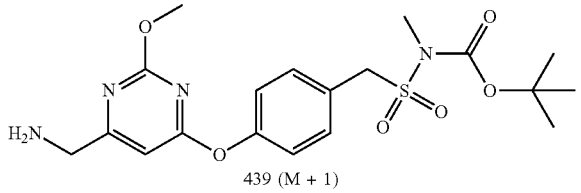 439 (M + 1) |
| 72 | tert-Butyl N-[[4-[6-(aminomethyl)-2-cyclopropyl-pyrimidin-4-yl]oxyphenyl]methylsulfonyl]-N-methyl-carbamate | 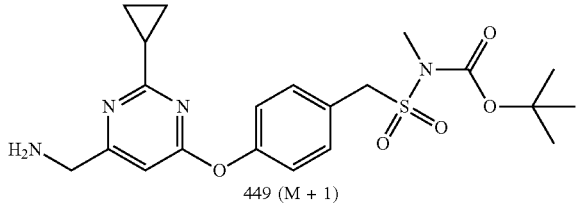 449 (M + 1) |
| 73 | N-[2-[4-[6-(Aminomethyl)-2-[(4-methoxyphenyl)-methylamino]pyrimidin-4-yl]oxyphenyl]ethyl]acetamide | 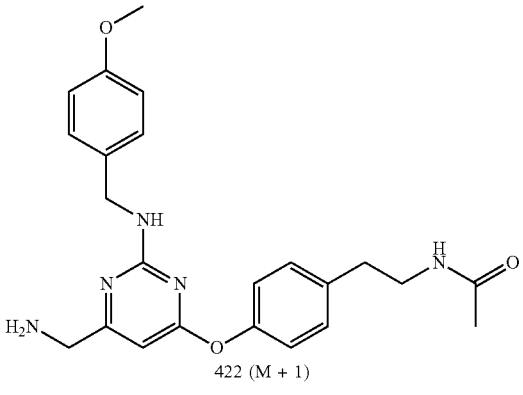 422 (M + 1) |
| 74 | [4-[6-(Aminomethyl)-2-morpholino-pyrimidin-4-yl]oxyphenyl]methanesulfonamide | 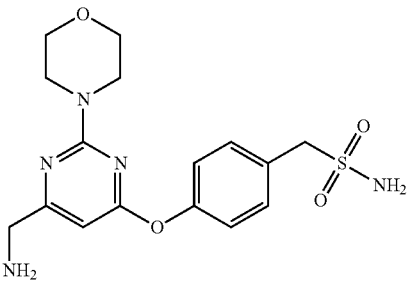 [SMILES: NCc1cc(Oc2ccc(CS(N)(=O)=O)cc2)nc(N2CCOCC2)n1] 380 (M + 1) |

TABLE 4-continued

Prepare the following compounds essentially according to the procedure for Preparation 52 using the appropriately substituted cyano compound.

| Prep. No. | Chemical name | Structure and Physical Data MS (m/z) or H[1] NMR |
|---|---|---|
| 75 | [4-[6-(Aminomethyl)-2-(4-methylpiperazin-1-yl)pyrimidin-4-yl]oxyphenyl]methanesulfonamide | H1 NMR (400.15 MHz, DMSO-d6): 7.42-7.38 (m, 2H), 7.19-7.11 (m, 2H), 6.93-6.92 (bs, 2H), 6.17 (d, J = 5.8 Hz, $^1$H), 4.28 (d, J = 4.9 Hz, 2H), 3.65-3.59 (m, 4H), 3.14 (s, 3H), 2.29-2.24 (m, 4H), 2.17-2.13 (m, 4H) |
| 76 | N-[2-[4-[6-(Aminomethyl)-2-[(4-methoxypheny-methylamino]pyrimidin-4-yl]oxyphenyl]ethyl]methanesulfonamide | 458 (M + 1) |
| 77 | tert-Butyl N-[2-[4-[[4-(aminomethyl)-2-pyridyl]oxy]phenyl]ethyl]carbamate | 344 (M + 1) |
| 78 | tert-Butyl N-[2-[4-[6-(aminomethyl)-2-methyl-pyrimidin-4-yl]oxyphenyl]ethyl]carbamate | 359 (M + 1) |
| 79 | tert-Butyl N-[[4-[6-(aminomethyl)-2-methyl-pyrimidin-4-yl]oxyphenyl]methylsulfonyl]-N-methyl-carbamate | 423 (M + 1) |

Preparation 80

[4-[[4-(Aminomethyl)-2-pyridyl]oxy]-3-fluoro-phenyl]methanesulfonamide

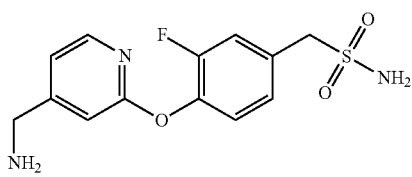 [SMILES: NCc1ccnc(Oc2ccc(CS(N)(=O)=O)cc2F)c1]

Stir a solution of [4-[(4-cyano-2-pyridyl)oxy]-3-fluorophenyl]methanesulfonamide (232 mg, 0.642 mmol) in tetrahydrofuran (3.2 mL) at ambient temperature. Add sodium tetrahydroborate (146 mg, 3.85 mmol) and trifluoroacetic acid (329 mg, 2.89 mmol), and then stir the mixture for one hr. Quench the reaction with 2M HCl to a pH=1 and stir for one hr. Remove the solvents under reduced pressure. Isolate the crude product via strong cation exchange chromatography eluting with 2N ammonia in methanol. Combine desired fractions and remove solvents under reduced pressure to provide the title compound (217 mg, 86.9%). MS (m/z): 312 (M+1).

Preparation 81 tert-Butyl N-[[2-methylsulfanyl-6-[4-(sulfamoylmethyl)phenoxy]pyrimidin-4-yl]methyl]carbamate

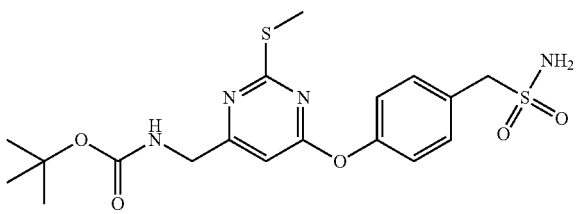 [SMILES: CSc1nc(CNC(=O)OC(C)(C)C)cc(Oc2ccc(CS(N)(=O)=O)cc2)n1]

Suspend 5% palladium on carbon (1.16 g, 0.448 mmol) in tetrahydrofuran (75 mL) under a nitrogen atmosphere in a pressure vessel. Add [4-(6-cyano-2-methylsulfanyl-pyrimidin-4-yl)oxyphenyl]methanesulfonamide (1.21 g, 2.99 mmol), triethylamine (1.66 mL, 11.9 mmol), and di-t-butyl-dicarbonate (716.7 mg, 3.28 mmol). Charge the pressure vessel with H$_2$ at 60 PSI. Shake the pressure vessel until completion of the reaction, as monitored by MS. Filter the resulting suspension through a pad of diatomaceous earth, collect the filtrate, and remove the solvent under reduced pressure to provide a residue. Subject the residue to silica gel chromatography eluting with a gradient of 0-100% ethyl acetate in iso-hexanes. Collect the appropriate fractions and remove the solvents under reduced pressure to provide the title compound (0.80 g, 57.7%). MS (m/z): 441 (M+1).

Preparation 82 tert-Butyl N-[[2-methylsulfonyl-6-[4-(sulfamoylmethyl)phenoxy]pyrimidin-4-yl]methyl]carbamate

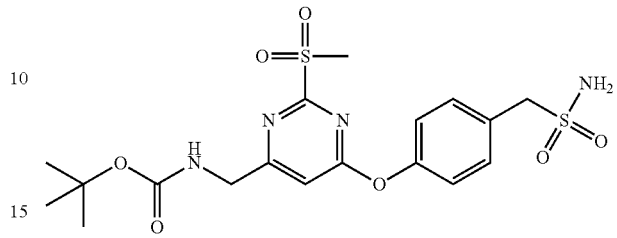

Dissolve tert-butyl N-[[2-methylsulfanyl-6-[4-(sulfamoylmethyl)phenoxy]pyrimidin-4-yl]methyl]carbamate (0.738 g, 1.59 mmol) in dichloromethane (20 mL) and add m-chloroperoxybenzoic acid (769 mg, 3.34 mmol). Stir the mixture at ambient temperature for 2 hours, then add additional m-chloroperoxybenzoic acid (146.5 mg, 0.636 mmol), and continue stirring for 2 additional hours. Quench the reaction with NaHCO$_3$ (saturated, aqueous), separate the layers and extract the aqueous layer again with dichloromethane. Combine the organic fractions, wash with Na$_2$CO$_3$ (saturated, aqueous), dry over MgSO$_4$, filter, and concentrate the filtrate under reduced pressure to provide the title product (644 mg, 86%). MS (m/z): 495 (M+23).

Preparation 83

1-[4-[6-[[(5-Chloropyrimidin-2-yl)amino]methyl]-2-methylsulfonyl-pyrimidin-4-yl]oxyphenyl]-N-methyl-methanesulfonamide

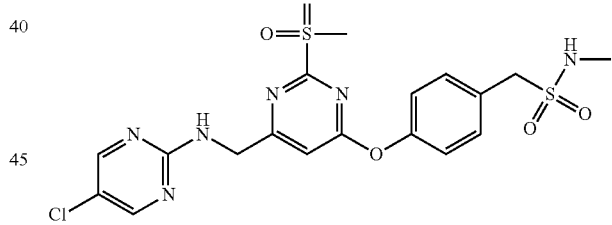

Prepare the title compound 83 essentially according to process for Preparation 82. MS (m/z): 499 (M+1).

Preparation 84

1-[4-[(4-Cyano-6-methoxy-2-pyridyl)oxy]phenyl]-N-methyl-methanesulfonamide

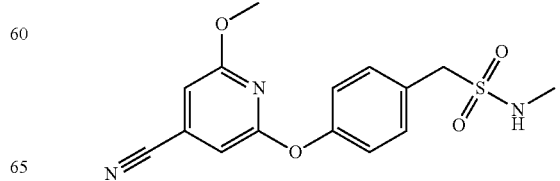

Combine 1-[4-[(6-chloro-4-cyano-2-pyridyl)oxy]phenyl]-N-methyl-methanesulfonamide (1.02 g, 3.02 mmol) and N-methylpyrrolidine (9.06 mL) in a microwave reaction vessel. Add triethylamine (1.26 mL, 9.06 mmol) and 30% sodium methoxide solution (in methanol, 815 mg, 4.53 mmol). Seal the vessel, heat via microwave to 110° C. and hold for 1 hour. Dilute the reaction mixture with ethyl acetate, wash with water, dry the organic fraction with $Na_2SO_4$, filter, collect the filtrate, and remove solvents under reduced pressure to provide a residue. Subject the residue to silica gel chromatography eluting with a gradient of 50-100% ethyl acetate in hexanes. Collect and combine the fractions with the desired material and remove the solvents under reduced pressure to provide the title compound (335 mg, 33.3%). MS (m/z): 334 (M+1).

TABLE 5

Prepare the following compounds essentially according to the process for Preparation 84 starting with the appropriate pyridine or pyrimidine compound.

| Prep. No. | Chemical name | Structure and Physical data (MS (m/z) or $H^1$ NMR) |
|---|---|---|
| 84A | 1-[4-[[4-Cyano-6-[(4-methoxphenyl)methylamino]-2-pyridyl]oxy]phenyl]-N-methyl-methanesulfonamide | 439 (M + 1) |
| 85 | [4-[[4-Cyano-6-[(4-methoxyphenyl)methylamino]-2-pyridyl]oxy]phenyl]methanesulfonamide | 425 (M + 1) |
| 85B | N-[2-[4-[6-Chloro-2-[(4-methoxyphenyl methlamino] pyrimidin-4-yl]oxyphenyl]ethyl]methanesulfonamide | NMR (400 MHz, CDCl3): 7.22-7.24 (m, 3H), 7.03-7.05 (m, 3H), 6.7-6.81 (m, 2H), 6.1-6.2 (m, 1H), 4.25-4.50 (m, 3H), 3.7-3.76 (s, 3H), 3.36-3.41 (m, 2H), 2.82-2.87 (m, 5H). |

TABLE 5-continued

Prepare the following compounds essentially according to the process for
Preparation 84 starting with the appropriate pyridine or pyrimidine compound.

| Prep. No. | Chemical name | Structure and Physical data (MS (m/z) or H¹ NMR) |
|---|---|---|
| 86 | tert-Butyl N-[2-[4-[[4-cyano-6-[(4-methoxypheny)methylamino]-2-pyridyl]oxy]phenyl]ethyl]carbamate | 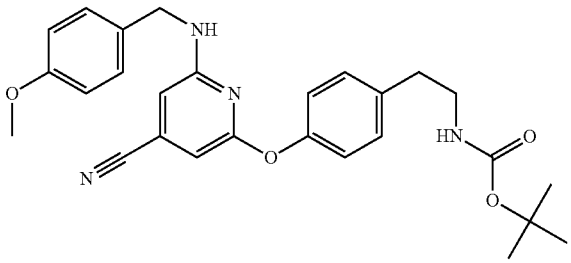 [SMILES: COc1ccc(CNc2cc(C#N)cc(Oc3ccc(CCNC(=O)OC(C)(C)C)cc3)n2)cc1]<br>475 (M + 1) |
| 87 | tert-Butyl N-[2-[4-[[4-cyano-6-[(4-methoxyphenyl)methylamino]-2-pyridyl]oxy]phenyl]-1-methyl-ethyl]carbamate | 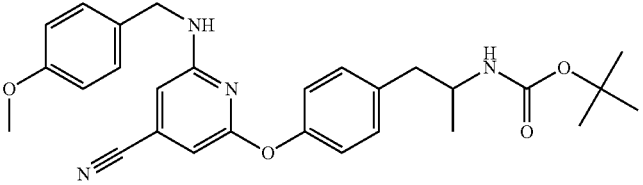 [SMILES: COc1ccc(CNc2cc(C#N)cc(Oc3ccc(CC(C)NC(=O)OC(C)(C)C)cc3)n2)cc1]<br>489 (M +1) |
| 88 | 1-[4-[(4-Cyano-6-morpholino-2-pyridyl)oxy]phenyl]-N-methyl-methanesulfonamide | 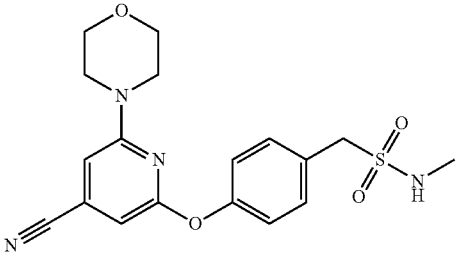 [SMILES: CNS(=O)(=O)Cc1ccc(Oc2cc(C#N)cc(N3CCOCC3)n2)cc1]<br>389 (M + 1) |
| 89 | tert-Butyl N-[[2-(methylamino)-6-[4-(sulfamoylmethyl)phenoxy]pyrimidin-4-yl]methyl]carbamate | 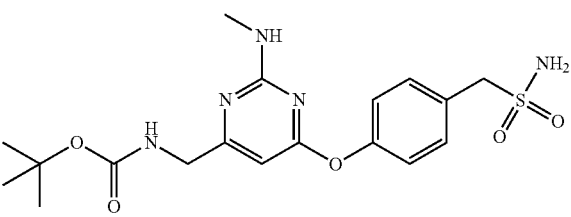 [SMILES: CNc1nc(CNC(=O)OC(C)(C)C)cc(Oc2ccc(CS(N)(=O)=O)cc2)n1]<br>424 (M + 1) |
| 90 | tert-Butyl N-[[2-amino-6-[4-(sulfamoylmethyl)phenoxy]pyrimidin-4-yl]methyl]carbamate | 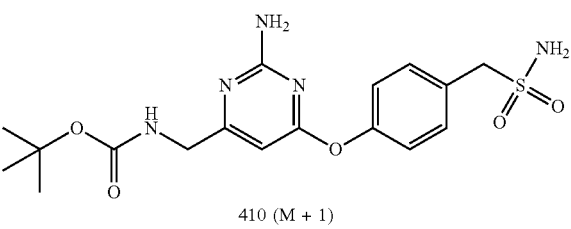<br>410 (M + 1) |

TABLE 5-continued

Prepare the following compounds essentially according to the process for
Preparation 84 starting with the appropriate pyridine or pyrimidine compound.

| Prep. No. | Chemical name | Structure and Physical data (MS (m/z) or $H^1$ NMR) |
|---|---|---|
| 91 | tert-Butyl-N-[[2-(dimethylamino)-6-[4-(sulfamoylmethyl)phenoxy]pyrimidin-4-yl]methyl]carbamate | 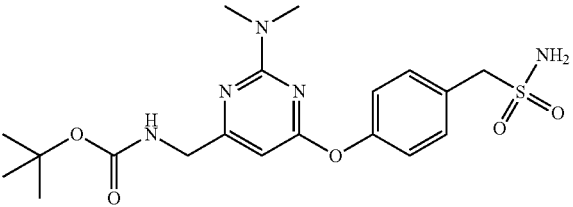 [SMILES: CN(C)c1nc(CNC(=O)OC(C)(C)C)cc(Oc2ccc(CS(N)(=O)=O)cc2)n1]<br>438 (M + 1) |
| 92 | N-[2-[4-[6-Cyano-2-[(4-methoxyphenyl)methylamino]pyrimidin-4-yl]oxyphenyl]ethyl]actamide | 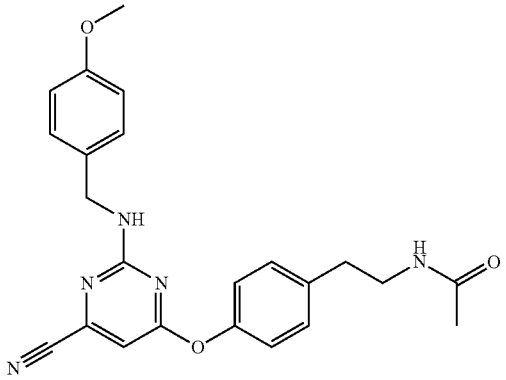 [SMILES: COc1ccc(CNc2nc(C#N)cc(Oc3ccc(CCNC(C)=O)cc3)n2)cc1]<br>418 (M + 1) |
| 93 | N-[2-[4-[6-Cyano-2-[(4-methoxypheny)methylamino]pyrimidin-4-yl]oxyphenyl]ethyl]methanesulfonamide | 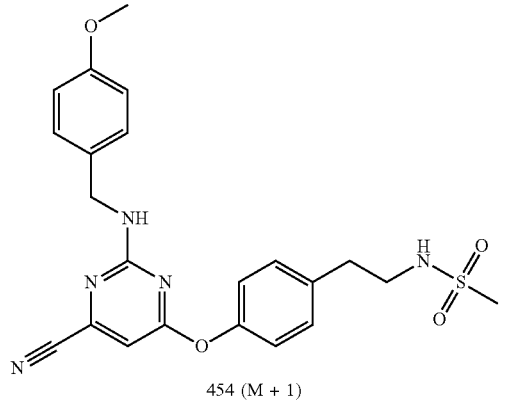<br>454 (M + 1) |

Preparation 94

[4-(6-Cyano-2-morpholino-pyrimidin-4-yl)oxyphenyl] methanesulfonamide

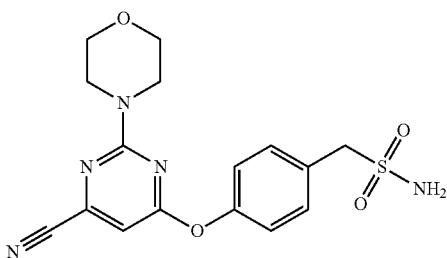 [SMILES: N#Cc1cc(Oc2ccc(CS(N)(=O)=O)cc2)nc(N2CCOCC2)n1]

Combine [4-(2-chloro-6-cyano-pyrimidin-4-yl)oxyphenyl]methanesulfonamide (1.2 g, 3.7 mmol), morpholine (450 mg, 5.2 mmol), cesium carbonate (3.0 g, 9.2 mmol), and 4,5-bis(diphenylphosphino)-9,9-dimethylxanthene (227 mg, 0.39 mmol). Add 15 mL 1,4-dioxane and degas via argon sparging. Add tris(dibenzylideneacetone)dipalladium (0) (0.18 g, 0.19 mmol) and stir for 3 days at ambient temperature. Filter the mixture through diatomaceous earth and concentrate the filtrate under reduced pressure to give the crude title product (1.3 g, 94%). MS (m/z): 376 (M+1).

Preparation 95

[4-[6-Cyano-2-(4-methylpiperazin-1-yl)pyrimidin-4-yl]oxyphenyl]methanesulfonamide

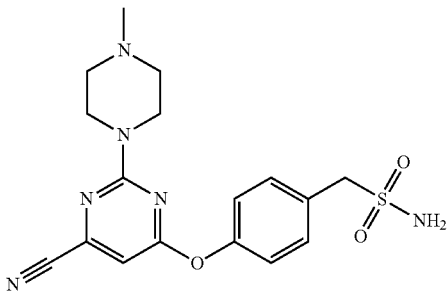 [SMILES: CN1CCN(c2nc(C#N)cc(Oc3ccc(CS(N)(=O)=O)cc3)n2)CC1]

Prepare the title compound essentially according to the method of Preparation 94. MS (m/z): 389 (M+1).

Alternative Preparation 95

In duplicate procedures, combine [4-(2,6-dichloropyrimidin-4-yl)oxyphenyl]methanesulfonamide (103 g, 308 mmol), 1-methylpiperazine (33.9 g, 339 mmol), cesium carbonate (200 g, 616 mmol), Xantphos® (17.8 g, 30 mmol) and 1,4-dioxanes (1 L). Degas the suspension and purge with nitrogen, then add tris(dibenzylideneacetone) dipalladium (0) (14.1 g, 15.4 mmol). Stir the suspension at ambient temperature for 2 hours under a nitrogen atmosphere. Combine the 2 reaction mixtures for workup. Pour the combined reaction mixtures into water (4 L) and extract with ethyl acetate (2×1 L). Combine the organic extracts and wash with brine (2×500 mL). Dry over $Na_2SO_4$, filter, and concentrate the filtrate under reduced pressure to give a residue. Pour the residue into water (2 L) and stir for 2 hours, which forms a precipitate. Collect the solid by filtration. Dry the solid under reduced pressure to give an intermediate solid (240 g).

Separate the intermediate solid into two lots. In duplicate procedures, add the intermediate solid (120 g, 301 mmol), zinc cyanide (70.8 g, 603 mmol) and 800 mL DMSO. Degas and purge the reaction with nitrogen, then add tetrakis (triphenylphosphine)palladium(0) (24.4 g, 21 mmol). Stir the suspension under nitrogen at 130° C. for 2 hours. Cool the solution to ambient temperature and combine the two reaction mixtures for workup. Pour the combined reaction mixtures into water (3.5 L) and extract with ethyl acetate (2×1 L). Combine the organic extracts and wash with brine (800 mL). Dry over $Na_2SO_4$, filter, and concentrate the filtrate under reduced pressure to give a residue. Subject the residue to flash column chromatography eluting with a gradient of dichloromethane:methanol (30:1 to 10:1) to give the title compound as a yellow solid (105 g, 41%). $^1$H NMR (400 MHz, DMSO-d6): 7.39-7.41 (m, 2H), 7.20-7.22 (m, 1H), 6.78-6.90 (m, 2H), 4.26 (s, 2H), 3.27-3.55 (m, 4H), 1.90-2.35 (m, 7H).

Preparation 95A

N-[2-[4-[6-Cyano-2-[(4-methoxyphenyl)methylamino]pyrimidin-4-yl]oxyphenyl]ethyl]methanesulfonamide

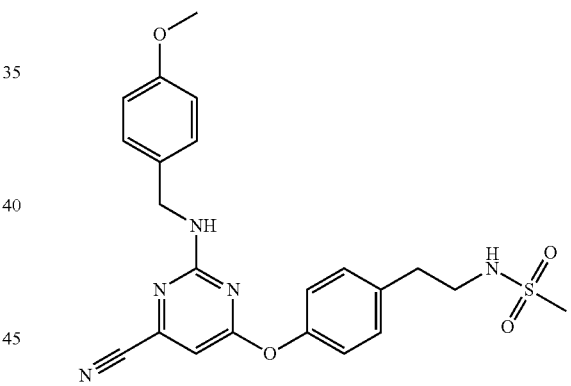

Prepare the title compound essentially according to the method of Alternative Preparation 95. $^1$H NMR (400.13 MHz, CDCl$_3$): 7.2-7.25 (m, 4H), 7.0-7.08 (m, 2H), 6.8-6.90 (m, 2H), 6.35-6.4 (m, 1H), 4.20-4.52 (m, 3H), 3.77 (s, 3H), 3.37-3.42 (m, 2H), 2.80-3.95 (m, 5H).

Preparation 96

[4-[6-(Aminomethyl)-2-(methylamino)pyrimidin-4-yl]oxyphenyl]methanesulfonamide

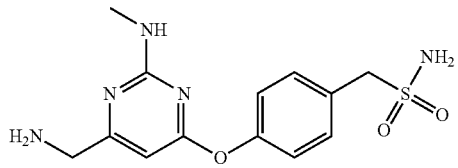 [SMILES: CNc1nc(CN)cc(Oc2ccc(CS(N)(=O)=O)cc2)n1]

Dissolve tert-butyl N-[[2-(methylamino)-6-[4-(sulfamoylmethyl) phenoxy]pyrimidin-4-yl]methyl]carbamate (728 mg, 1.20 mmol) in methanol (10 mL). Add HCl (10 mL, 4M in dioxanes) and stir at ambient temperature overnight. Remove the solvents under reduced pressure. Dissolve the residue in HCl (20 mL, 4M in dioxanes). Remove solvent under reduced pressure to provide a crude product. Subject the crude product to strong cation exchange chromatography eluting with 7N ammonia in methanol. Combine desired fractions and remove solvents under reduced pressure to provide the title compound as yellow oil (299 mg, 76.8%). MS (m/z): 324 (M+1).

remove the solvent under reduced pressure to provide the crude title product as a white solid. (715 mg, 45%). MS (m/z): 323 (M+1).

Preparation 100

2-Chloro-5-(difluoromethyl)pyrimidine

Dissolve 2-chloropyrimidine-5-carbaldehyde (0.5 g, 3.5 mmol) in chloroform (10 mL), add diethylaminosulfur tri-

TABLE 6

Prepare the following compounds essentially according to the method of Preparation 96 using the appropriate substituted BOC protected sulfonamide compound.

| Prep. No. | Chemical name | Structure and Physical Data MS (m/z) |
|---|---|---|
| 97 | [4-[2-Amino-6-(aminomethyl)pyrimidin-4-yl]oxyphenyl]methanesulfonamide | 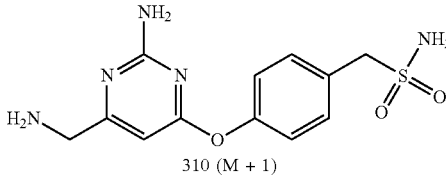 310 (M + 1) |
| 98 | [4-[6-(Aminomethyl)-2-(dimethylamino)pyrimidin-4-yl]oxyphenyl]methanesulfonamide | 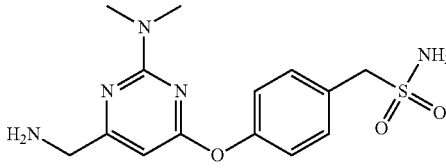 388 (M + 1) |

Preparation 99

[4-[6-[1-Aminoethyl]-2-methyl-pyrimidin-4-yl]oxyphenyl]methanesulfonamide

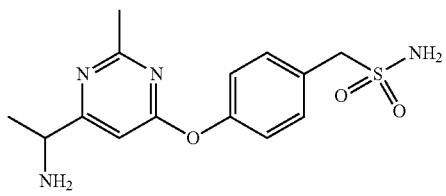 [SMILES: Cc1nc(Oc2ccc(CS(N)(=O)=O)cc2)cc(C(C)N)n1]

Dissolve [4-(6-cyano-2-methyl-pyrimidin-4-yl)oxyphenyl]methanesulfonamide (1.5 g, 4.9 mmol) in tetrahydrofuran (15 mL), cool the mixture to 0° C., and add methylmagnesium bromide (1M in tetrahydrofuran, 6.6 mL, 20 mmol). Allow the reaction to warm to ambient temperature and stir for 2 hours. Pour the mixture into a solution of sodium borohydride (0.93 g, 25 mmol) in methanol (50 mL) and stir at ambient temperature. Pour the mixture into water and extract with ethyl acetate. Combine the ethyl acetate extracts, dry over $Na_2SO_4$, filter, collect the filtrate, and oxide (567 mg, 3.5 mmol), then reflux for 1 hour. Cool the mixture to ambient temperature and quench with $H_2O$. Separate the layers, wash the organic fraction with $H_2O$ (2×), dry over $MgSO_4$, filter, collect the filtrate, and concentrate the filtrate under reduced pressure to provide the title product (327 mg, 51%). $^1H$ NMR (400.13 MHz, $CDCl_3$): 8.79 (s, 2H), 6.78 (t, J=55 Hz, 1H).

Preparation 101

5-(Difluoromethyl)-N-(4-pyridylmethyl)pyrimidin-2-amine

Dissolve 4-aminomethylpyridine (175 mg, 1.62 mmol) and 2-chloro-5-(difluoromethyl)pyrimidine (325 mg, 1.78 mmol) in 809 microliters of dimethylformamide and place under a nitrogen atmosphere. Add potassium carbonate (447 mg, 3.24 mmol), heat to 60° C., and stirring overnight. Quench the reaction with $H_2O$, filter, and extract the filtrate with ethyl acetate (3 times). Combine the ethyl acetate extracts, wash with $H_2O$ (3×), brine, dry over $MgSO_4$, filter, collect the filtrate and remove the solvents under reduced pressure. Subject the residue to silica gel chromatography eluting with a gradient of 0-10% methanol in dichloromethane. Combine the appropriate fractions and remove solvents under reduced pressure to provide the title product (231 mg, 57%). MS (m/z): 237 (M+1).

TABLE 7

Prepare the following compounds essentially by the method of Preparation 101

| Prep. No. | Chemical name | Structure and Physical Data MS (m/z) |
|---|---|---|
| 102 | [4-[[4-[[[(5-Chloropyrimidin-2-yl)amino]methyl]-6-[(4-methoxyphenyl)methylamino]-2-pyridyl]oxy]phenyl]methanesulmonide | 541 (M + 1) |
| 103 | [4-[[4-[[[(5-Ethylpyrimidin-2-yl)amino]methyl]-6-[(4-methoxyphenyl)methylamino]-2-pyridyl]oxy]phenyl]methanesulfonamide | 535 (M + 1) |
| 104 | tert-Butyl N-[2-[4-[[4-[[[(5-chloropyrimidin-2-yl)amino]methyl]-6-[(4-methoxyphenyl)methylamino]-2-pyridyl]oxy]phenyl]ethyl]carbamate | 591 (M + 1) |

TABLE 7-continued

Prepare the following compounds essentially by the method of Preparation 101

| Prep. No. | Chemical name | Structure and Physical Data MS (m/z) |
|---|---|---|
| 105 | tert-Butyl N-[[4-[[4-[[(5-chloropyrimidin-2-yl)amino]methyl]-6-methyl-2-pyridyl]oxy]phenyl]methyl]carbamate | 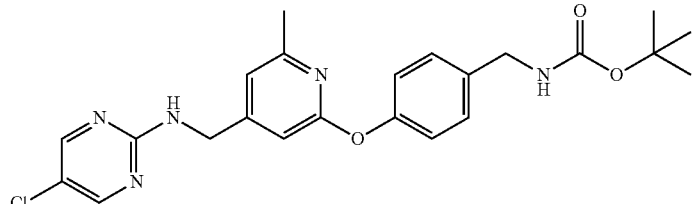<br>456 (M + 1) |
| 106 | 5-Chloro-N-[1-(4-pyridyl)etyl]pyrimidin-2-amine | 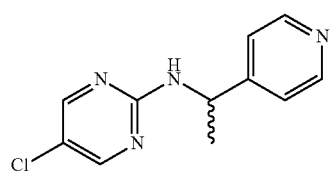 [SMILES: CC(Nc1ncc(Cl)cn1)c1ccncc1]<br>235 (M + 1) |
| 107 | tert-Butyl N-[2-[4-[[4-[[(5-ethylpyrimidin-2-yl)amino]methyl]-6-[(4-methoxyphenyl)methylamino]-2-pyridyl]oxy]phenyl]ethyl]carbamate | 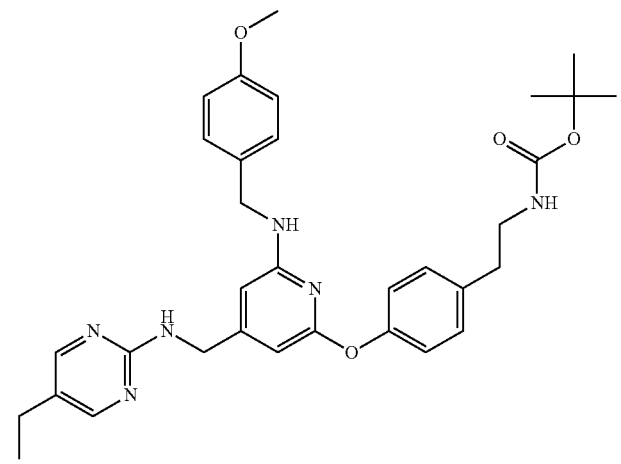 [SMILES: CCc1cnc(NCc2cc(NCc3ccc(OC)cc3)nc(Oc3ccc(CCNC(=O)OC(C)(C)C)cc3)c2)nc1]<br>585 (M + 1) |
| 108 | 5-Chloro-N-(4-pyridylmethy)pyrimidin-2-amine | 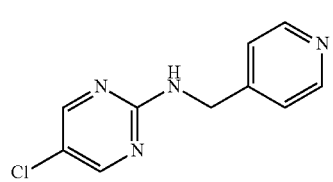 [SMILES: Clc1cnc(NCc2ccncc2)nc1]<br>221 (M + 1) |
| 109 | tert-Butyl N-[2-[4[6-[[(5-chloropyrimidin-2-yl)amino]methyl]pyrimidin-4-yl]oxyphenyl]ethyl]carbamate | 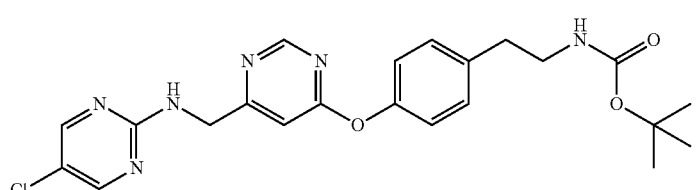<br>457 (M + 1) |

TABLE 7-continued

Prepare the following compounds essentially by the method of Preparation 101

| Prep. No. | Chemical name | Structure and Physical Data MS (m/z) |
|---|---|---|
| 110 | tert-Butyl N-[2-[4-[2-amino-6-[[(5-chloropyrimidin-2-yl)amino]methyl]pyrimidin-4-yl]oxyphenyl]ethyl]carbamate | 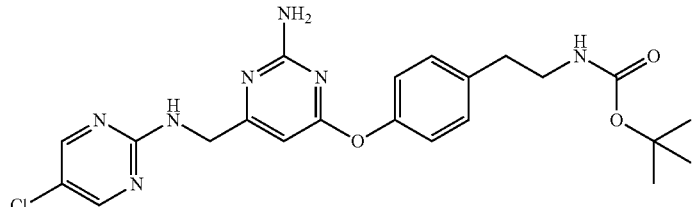<br>472 (M + 1) |
| 111 | tert-Butyl N-[2-[4-[6-[[(5-chloropyrimidin-2-yl)amino]methyl]-2-methy;-pyrimidin-4-yl]oxyphenyl]ethyl]carbamate | 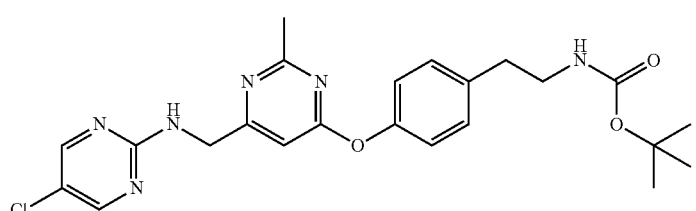<br>471 (M + 1) |
| 112 | tert-Butyl N-[2-[4-[6-[[(5-ethylpyrimidin-2-yl)amino]methyl]-2-methyl-pyrimidin-4-yl]oxyphenyl]ethyl]carbamate | 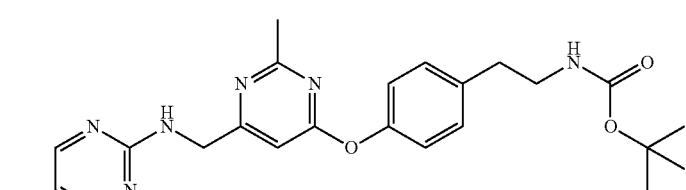<br>465 (M + 1) |
| 113 | N-[2-[4-[6-[[(5-Ethylprimidin-2-yl)amino]methyl]-2-[(4-methoxyphenyl)methylamino]pyrimidin-4-yl]oxyphenyl]ethyl]acetamide | 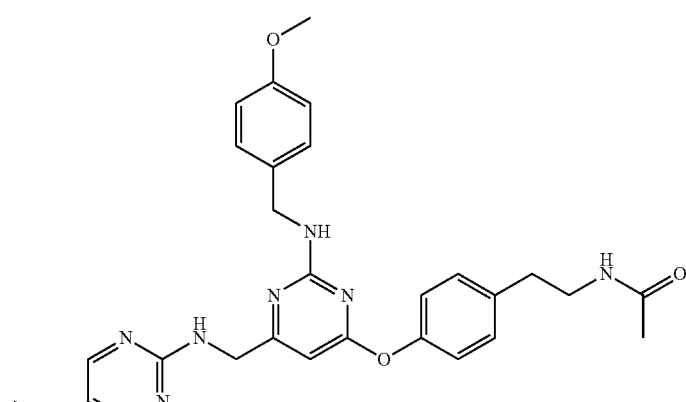<br>528 (M + 1) |
| 114 | tert-Butyl N-[2-[4-[2-amino-6-[[(5-ethylpyrimidin-2-yl)amino]methyl]pyrimidin-4-yl]oxy[phenyl]ethyl]carbamate | 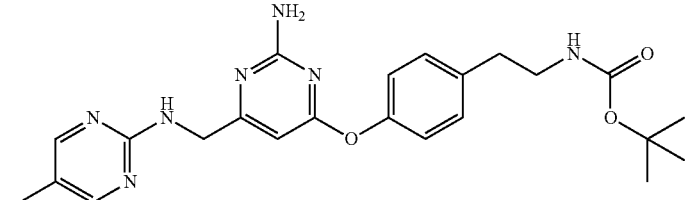<br>466 (M + 1) |

TABLE 7-continued

Prepare the following compounds essentially by the method of Preparation 101

| Prep. No. | Chemical name | Structure and Physical Data MS (m/z) |
|---|---|---|
| 115 | N-[2-[4-[6-[[(5-Ethylpyrimidin-2-yl)amino]methyl]-2-[(4-methoxyphenyl)methylamino]pyrimidin-4-yl]oxyphenyl]ethyl]methanesulfonamide | 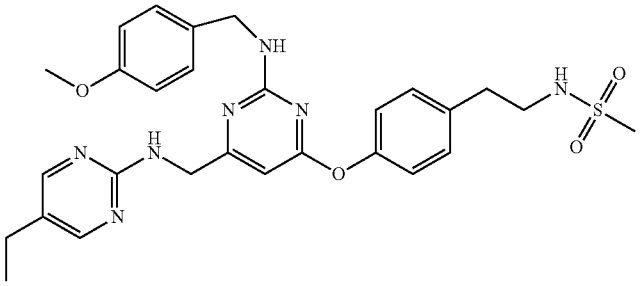 [SMILES: CCc1cnc(NCc2cc(Oc3ccc(CCNS(C)(=O)=O)cc3)nc(NCc3ccc(OC)cc3)n2)nc1] 564 (M + 1) |
| 116 | 1-[4-[[4-[[(5-Chloropyrimidin-2-yl)amino]methyl]-6-[(4-methoxyphenyl)methylamino]-2-pyridyl]oxy]phenyl]-N-methyl-methanesulfonamide | 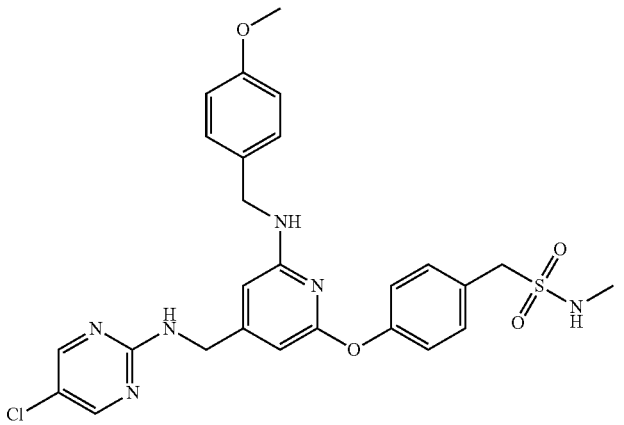 [SMILES: CNS(=O)(=O)Cc1ccc(Oc2cc(CNc3ncc(Cl)cn3)cc(NCc3ccc(OC)cc3)n2)cc1] 555 (M + 1) |
| 117 | tert-Butyl N-[2-[4-[[4-[[(5-ethylpyrimidin-2-yl)amino]methyl]-6-[(4-methoxyphenyl)methylamino]-2-pyridyl]oxy]phenyl]-1-methyl-ethyl]carbamate | 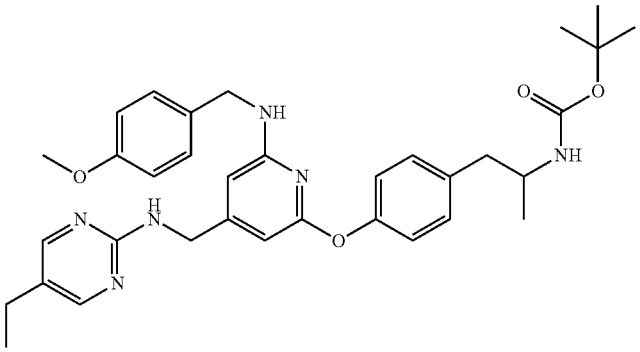 [SMILES: CCc1cnc(NCc2cc(NCc3ccc(OC)cc3)nc(Oc3ccc(CC(C)NC(=O)OC(C)(C)C)cc3)c2)nc1] 599 (M + 1) |

TABLE 7-continued

Prepare the following compounds essentially by the method of Preparation 101

| Prep. No. | Chemical name | Structure and Physical Data MS (m/z) |
|---|---|---|
| 117A | tert-Butyl 4-[4-[[(5-chloropyrimidin-2-yl)amino]methyl]-6-[4-(sulfamoylmethyl)phenoxy]pyrimidin-2-yl]piperazine-1-carboxylate | 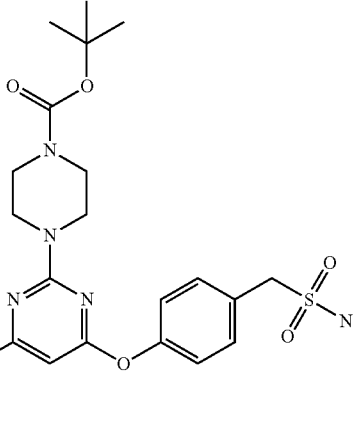 591 (M + 1) |

Preparation 118

N-[[2-[4-(2-Aminoethyl)phenoxy]-4-pyridyl]methyl]-5-ethyl-pyrimidin-2-amine

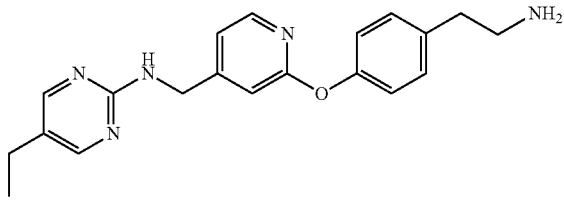 [SMILES: CCc1cnc(NCc2ccnc(Oc3ccc(CCN)cc3)c2)nc1]

Charge a tube with tert-butyl N-[2-[4-[[4-(aminomethyl)-2-pyridyl]oxy]phenyl]ethyl]carbamate (3.53 g, 7.71 mmol), 2-chloro-5-ethylpyridine (1.1 g mg, 7.71 mmol), sodium tert-butoxide (2.22 g, 23.1 mmol), Brettphos® (dicyclohexyl-[3,6-dimethoxy-2-(2,4,6-triisopropylphenyl)phenyl]phosphane, Aldrich #718742, 32.8 mg, 0.154 mmol), Brettphos® Precatalyst (Chloro[2-(dicyclohexylphosphino)-3,6-dimethoxy-2',4', 6'-triisopropyl-1,1'-biphenyl][2-(2-aminoethyl)phenyl]palladium(II), Aldrich #718750, 150 mg) and tetrahydrofuran (25.7 mL). Degas the tube with nitrogen; seal it; heat the mixture to 70° C.; and stir for 3 hours. Evaporate the solvent, add HCl (aq) (10 mL 5N) and stir for 2 days. Quench the reaction with NaOH to pH=12 and extract with dichloromethane. Combine the dichloromethane extracts, remove solvents under reduced pressure to provide the title compound as a yellow oil (700 mg, 26.0%, MS (m/z): 350 (M+1)) which can be used without further purification.

Preparation 119

1-[4-[(4-Formyl-2-pyridyl)oxy]phenyl]-N-methyl-methanesulfonamide

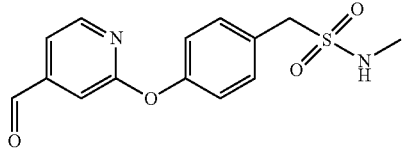 [SMILES: CNS(=O)(=O)Cc1ccc(Oc2cc(C=O)ccn2)cc1]

Dissolve N-methoxy-N-methyl-2-[4-(methylsulfamoylmethyl)phenoxy] pyridine-4-carboxamide (226 mg, 0.618 mmol) in dichloromethane (6.2 mL); cool the solution to −20° C. under a nitrogen atmosphere; and drop-wise add DIBAL-H® (1.0 M, 0.928 mL, 0.928 mmol). Stir the mixture while maintaining it at −20° C. Add additional DIBAL-H® (1.0 M, 0.928 mL, 0.928 mmol) after 2 hours. Stir for an additional 1 hour. Cool the mixture to −60° C., and pour it into a saturated aqueous solution of potassium sodium tartrate. Extract the resulting mixture with ethyl acetate. Combine the ethyl acetate extracts; dry over $MgSO_4$; filter; collect the filtrate; and concentrate the filtrate under reduced pressure to provide a residue. Subject the residue to silica gel chromatography eluting with a gradient of 50-100% ethyl acetate in hexanes. Combine the appropriate fractions and remove the solvents under reduced pressure to provide the title compound as a colorless oil (156 mg, 82.6%). MS (m/z): 307 (M+1).

Preparation 120

5-Chloro-N-[(1-oxidopyridin-1-ium-4-yl)methyl]pyrimidin-2-amine

Dissolve 5-chloro-N-(4-pyridylmethyl)pyrimidin-2-amine (360 g, 1.63 mol) in dichloromethane (3.6 L). Add methyltrioxorhenium (12.6 g, 50.6 mmol) and cool the mixture to −10° C. Add $H_2O_2$ (504 mL, 15%, 2.48 mol) drop-wise over 3.5 hours, then stir the mixture for 2.5 hours while maintaining the temperature between −10 and 5° C. Add petroleum ether (3600 mL) to the mixture; stir it for 20 min at 0° C.; and then filter to collect a solid material. Suspend the solid in dichloromethane (3 L); stir the suspension for 30 minutes at ambient temperature; filter to collect the solid. Suspend the solid in acetone (540 mL) and stir the suspension at ambient temperature for 1.5 hours. Filter to collect the title compound as an off-white solid. (225 g, 58.3%). $^1$H NMR (400.13 MHz, DMSO-d6): 8.35 (s, 2H), 8.13 (d, J=7 Hz, 2H), 8.09 (t, J=6.4 Hz, 1H), 7.29 (d, J=7 Hz, 2H), 4.4 (d, J=6.4 Hz, 2H).

TABLE 8

Prepare the following compounds essentially by the method of Preparation 120

| Prep. No. | Chemical name | Structure and Physical Data MS (m/z) |
|---|---|---|
| 121 | 5-(Difluoromethyl)-N-[(1-oxidopyridin-1-ium-4-yl)methyl]-pyrimidin-2-amine | 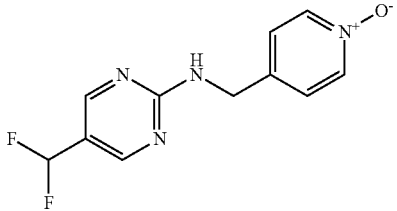 [SMILES: [O-][n+]1ccc(CNc2ncc(C(F)F)cn2)cc1]<br>253 (M + 1) |
| 122 | N-Methoxy-N-methyl-1-oxido-pyridin-1-ium-4-carboxamide | 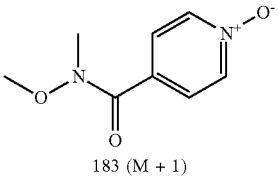<br>183 (M + 1) |
| 123 | 5-Chloro-N-[1-(1-oxidopyridin-1-ium-4-yl)ethyl]pyrimidin-2-amine | 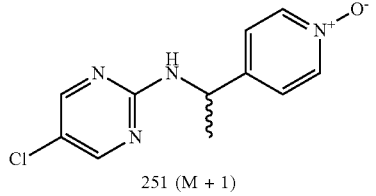<br>251 (M + 1) |

Preparation 124 tert-Butyl N-[2-[4-[[4-[[(5-chloropyrimidin-2-yl)amino]methyl]-2-pyridyl]oxy]phenyl]-1-methyl-ethyl]carbamate

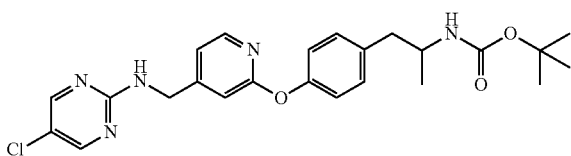 [SMILES: CC(Cc1ccc(Oc2cc(CNc3ncc(Cl)cn3)ccn2)cc1)NC(=O)OC(C)(C)C]

Dissolve 5-chloro-N-[(1-oxidopyridin-1-ium-4-yl)methyl]pyrimidin-2-amine (1.7 g, 7.18 mmol) and tert butyl N-[2-(4-hydroxyphenyl)-1-methyl-ethyl]carbamate (2.17 g, 8.62 mmol) in dichloromethane (21 mL). Add diisopropylethylamine (4.70 mL, 26.9 mmol) and bromo-tris-pyrrolidino-phosphonium hexafluorophosphate (4.35 g, 9.34 mmol), then stir the mixture at ambient temperature overnight. Evaporate the organic solvent under reduced pressure. Subject the residue to silica gel chromatography eluting with a gradient of 0-100% ethyl acetate in hexanes. Collect the desired fractions and evaporate the solvent to provide the title compound as a clear solid. (1.90 g, 56.3%). MS (m/z): 470 (M+1).

TABLE 9

Prepare the following compounds essentially by the method of Preparation 124

| Prep. No. | Chemical name | Structure and Physical data |
|---|---|---|
| 125 | tert-Butyl N-[2-[4-[[4-[[(5-chloropyrimidin-2-yl)amino]methyl]-2-pyridyl]oxy]phenyl]ethyl]carbamate | 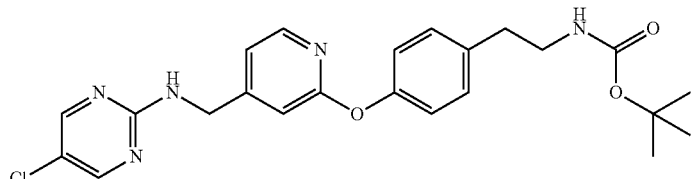<br>456 (M + 1). |

TABLE 9-continued

Prepare the following compounds essentially by the method of Preparation 124

| Prep. No. | Chemical name | Structure and Physical data |
|---|---|---|
| 126 | N-Methoxy-N-methyl-2-[4-(methylsulfamoylmethyl)phenoxy]-pyridine-4-carboxamide | 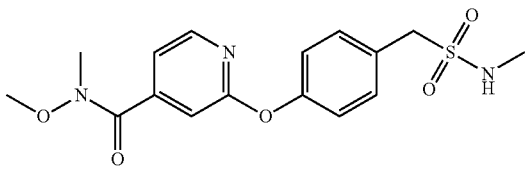 366 (M + 1). |

Preparation 127

N-[[2-[4-(2-Aminoethyl)phenoxy]-4-pyridyl]methyl]-5-chloro-pyrimidin-2-amine

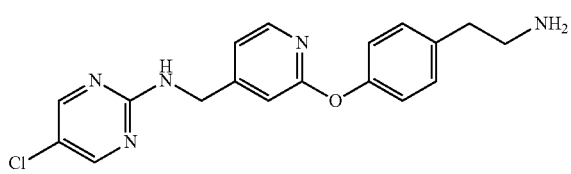 [SMILES: NCCc1ccc(Oc2cc(CNc3ncc(Cl)cn3)ccn2)cc1]

Dissolve tert-butyl N-[2-[4-[[4-[[(5-chloropyrimidin-2-yl)amino]methyl]-2-pyridyl]oxy]phenyl]ethyl]carbamate (3.57 g, 6.97 mmol) in 1,4-dioxane (17 mL); add HCl (4M in 1,4-dioxane, 17.4 mL, 69.69 mmol); and stir the mixture for 2 hr at ambient temperature. Remove solvent under reduced pressure. Subject the residue to strong cation exchange chromatography eluting with 2N ammonia in methanol. Combine desired fractions and remove solvents under reduced pressure to provide the title compound as a white solid (2.26 g, 91.1%). MS (m/z): 356 (M+1).

TABLE 10

Prepare the following compounds essentially by the method of Preparation 127.

| Prep. No. | Chemical name | Structure and Physical data |
|---|---|---|
| 127 A | N-[[2-[4-(2-Aminoethyl)phenoxy]-6-[(4-methoxyphenyl)methylamino]-4-pyridyl]methyl]-5-chloro-pyrimidin-2-amine | 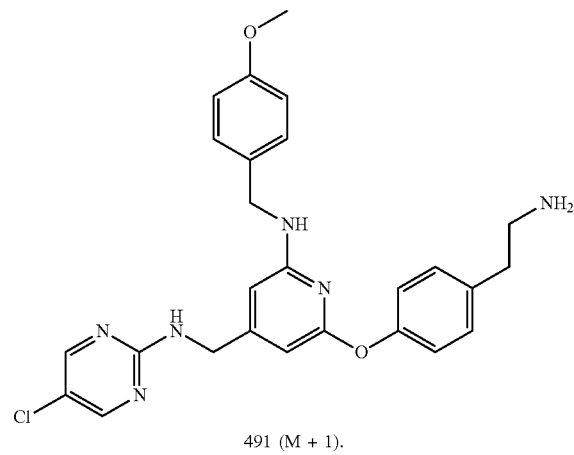 491 (M + 1). |
| 128 | N-[[2-[4-(Aminomethyl)phenoxy]-6-methyl-4-pyridyl]methyl]-5-chloro-pyrimidin-2-amine; hydrochloride | 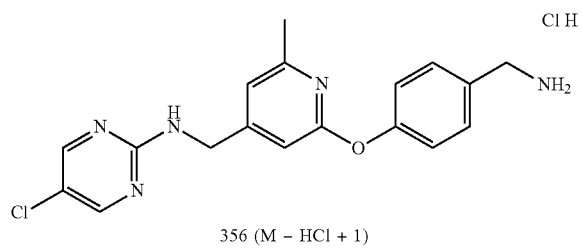 356 (M − HCl + 1) |

TABLE 10-continued

Prepare the following compounds essentially by the method of Preparation 127.

| Prep. No. | Chemical name | Structure and Physical data |
|---|---|---|
| 129 | N-[[2-[4-(2-Aminoethyl)phenoxy]-6-[(4-methoxyphenyl)methylamino]-4-pyridyl]methyl]-5-ethyl-pyrimidin-2-amine | 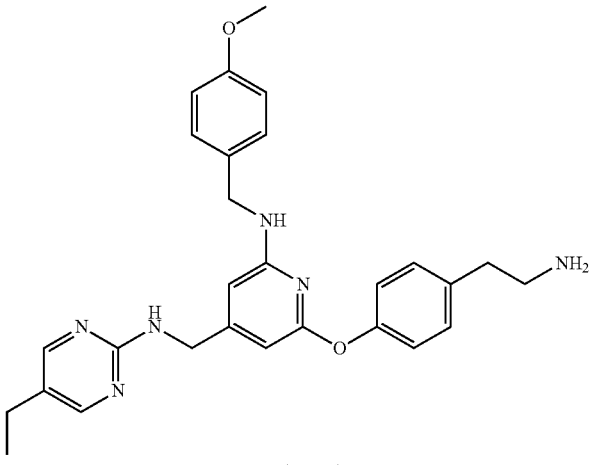 [SMILES: CCc1cnc(NCc2cc(NCc3ccc(OC)cc3)nc(Oc3ccc(CCN)cc3)c2)nc1] 485 (M + 1). |
| 130 | N-[[2-[4-(2-Aminopropyl)phenoxy]-4-pyridyl]methyl]-5-chloro-pyrimidin-2-amine; dihydrochloride | 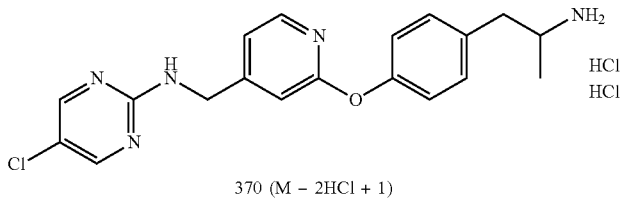 370 (M − 2HCl + 1) |
| 131 | N-[[2-[4-(2-Aminopropyl)phenoxy]-6-[(4-methoxyphenyl)methylamino]-4-pyridyl]methyl]-5-chloro-pyrimidin-2-amine | 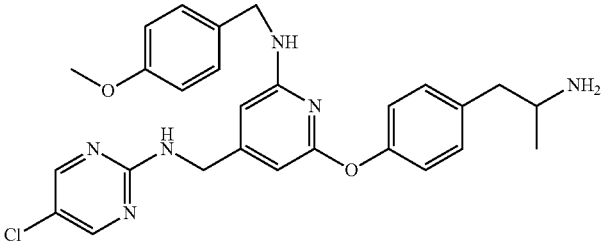 [SMILES: COc1ccc(CNc2cc(CNc3ncc(Cl)cn3)cc(Oc3ccc(CC(C)N)cc3)n2)cc1] 505 (M + 1). |
| 132 | N-[[2-[4-(2-Aminopropyl)phenoxy]-6-[(4-methoxyphenyl)methylamino]-4-pyridyl]methyl]-5-ethyl-pyrimidin-2-amine | 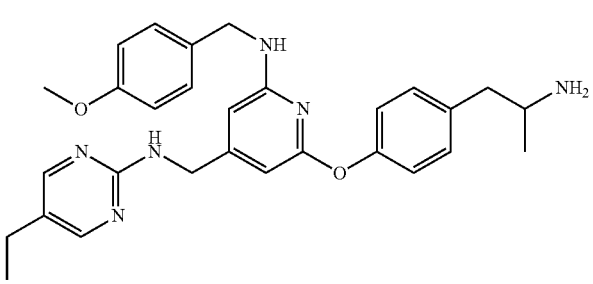 [SMILES: CCc1cnc(NCc2cc(NCc3ccc(OC)cc3)nc(Oc3ccc(CC(C)N)cc3)c2)nc1] 499 (M + 1). |
| 133 | N-[[6-[4-(2-Aminoethyl)phenoxy]pyrimidin-4-yl]methyl]-5-chloro-pyrimidin-2-amine | 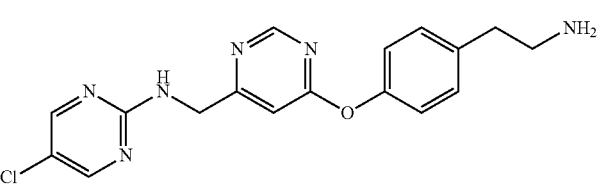 [SMILES: NCCc1ccc(Oc2cc(CNc3ncc(Cl)cn3)ncn2)cc1] 357 (M + 1). |

TABLE 10-continued

Prepare the following compounds essentially by the method of Preparation 127.

| Prep. No. | Chemical name | Structure and Physical data |
|---|---|---|
| 134 | 4-[4-(2-Aminoethyl)phenoxy]-6-[[(5-chloropyrimidin-2-yl)amino]methyl]pyrimidin-2-amine | 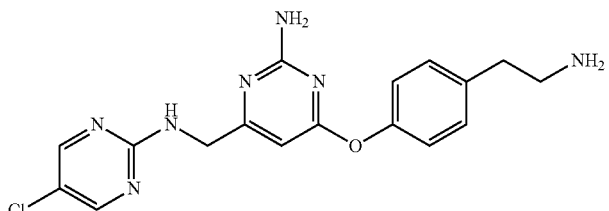<br>372 (M + 1) |
| 135 | N-[[6-[4-(2-Aminoethyl)phenoxy]-2-methyl-pyrimidin-4-yl]methyl]-5-ethyl-pyrimidin-2-amine | 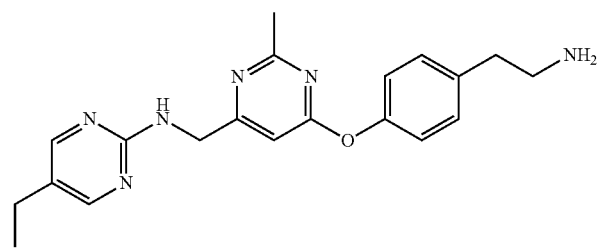 [SMILES: CCc1cnc(NCc2cc(Oc3ccc(CCN)cc3)nc(C)n2)nc1]<br>365 (M + 1) |
| 136 | N-[[6-[4-(2-Aminoethyl)phenoxy]-2-methyl-pyrimidin-4-yl]methyl]-5-chloro-pyrimidin-2-amine | 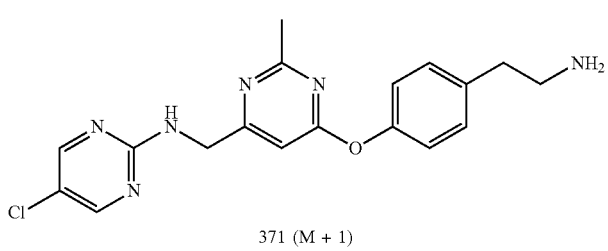<br>371 (M + 1) |
| 137 | 4-[4-(2-Aminoethyl)phenoxy]-6-[[(5-ethylpyrimidin-2-yl)amino]methyl]pyrimidin-2-amine | 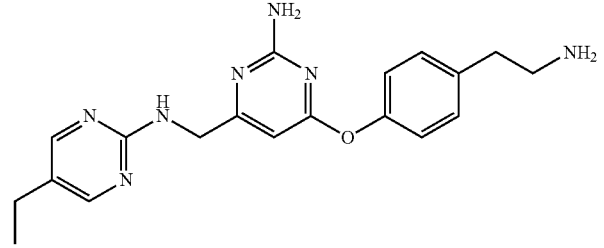 [SMILES: CCc1cnc(NCc2cc(Oc3ccc(CCN)cc3)nc(N)n2)nc1]<br>366 (M + 1) |

Preparation 138

1-[2-[4-[[4-[[(5-Chloropyrimidin-2-yl)amino]methyl]-6-[(4-methoxyphenyl)methylamino]-2-pyridyl]oxy]phenyl]ethyl]-3-methyl-urea

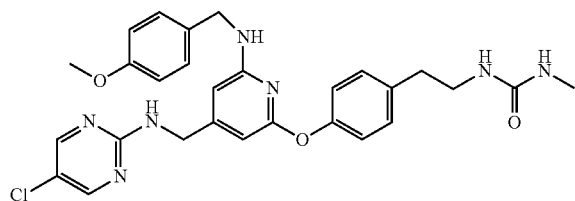 [SMILES: CNC(=O)NCCc1ccc(Oc2cc(CNc3ncc(Cl)cn3)cc(NCc3ccc(OC)cc3)n2)cc1]

Combine N-[[2-[4-(2-aminoethyl)phenoxy]-6-[(4-methoxyphenyl)methylamino]-4-pyridyl]methyl]-5-chloro-pyrimidin-2-amine (325 mg, 0.662 mmol), acetonitrile (5 mL), methylaminoformyl chloride (60 mg, 0.61 mmol), and triethylamine (0.15 mL, 1.1 mmol). Stir the solution at ambient temperature for 16 hours. Add $H_2O$ and filter to collect the solid. Subject the solid to flash column chromatography on $SiO_2$ eluting with a gradient of 25-100% (10% 2M $NH_3$/methanol in dichloromethane) in dichloromethane. Collect the appropriate fractions and remove the solvents under reduced pressure to provide the title compound (230 mg, 63.4%). MS (m/z): 548 (M+1).

Preparation 139

5-Ethyl-2-[[2-[(4-methoxyphenyl)methylamino]-6-[4-[2-(sulfamoylamino)ethyl]phenoxy]-4-pyridyl]methylamino]pyrimidine

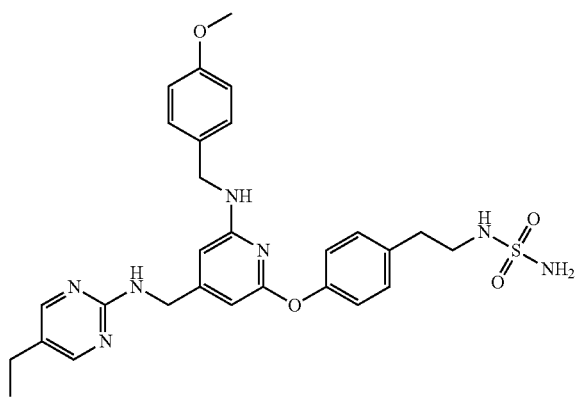 [SMILES: CCc1cnc(NCc2cc(NCc3ccc(OC)cc3)nc(Oc3ccc(CCNS(N)(=O)=O)cc3)c2)nc1]

Combine N-[[2-[4-(2-aminoethyl)phenoxy]-6-[(4-methoxyphenyl)methylamino]-4-pyridyl]methyl]-5-ethyl-pyrimidin-2-amine (0.845 g, 1.74 mmol); sulfuric diamide (864 mg, 8.72 mmol) and 1,4-dioxane (25.4 mL); reflux the mixture overnight. Remove solvents under reduced pressure and add ethyl acetate. Wash the ethyl acetate solution with brine; dry over $MgSO_4$; filter; collect the filtrate; and concentrate the filtrate under reduced pressure to give the provide compound (1.0 g, 35%). MS (m/z): 564 (M+1).

Preparation 140

Racemic 5-ethyl-2-[[2-[(4-methoxyphenyl)methylamino]-6-[4-[2-(sulfamoylamino)propyl]phenoxy]-4-pyridyl]methylamino]pyrimidine

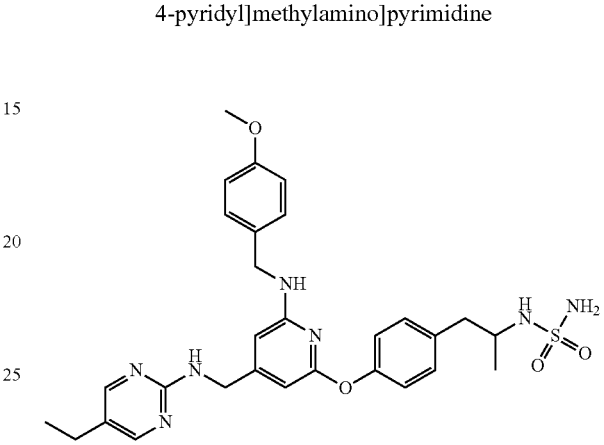

Prepare the title compound essentially according to procedure for Preparation 139. MS (m/z): 578 (M+1).

Example 1

[4-[[4-[[(5-Ethylpyrimidin-2-yl)amino]methyl]-2-pyridyl]oxy]phenyl]methanesulfonamide

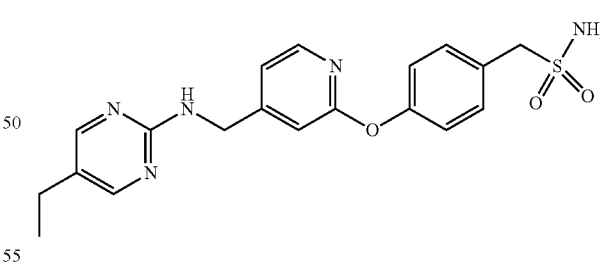

Add potassium fluoride (81.8 mg, 0.563 mmol) to a solution of [4-[[4-(aminomethyl)-2-pyridyl]oxy]phenyl]methanesulfonamide (167 mg, 0.512 mmol) and 2-chloro-5-ethylpyrimidine (79 mg, 0.53 mmol) in dimethyl sulfoxide (2.2 mL). Heat the mixture to 100° C. for 22 hours. Cool the mixture to ambient temperature and quench with water. Extract with dichloromethane (3×) and combine the organic extracts. Dry the organic extracts over $MgSO_4$, filter, and concentrate the filtrate under reduced pressure. Purify via low pH HPLC to provide the title compound (179 mg, 78.7% yield). MS (m/z): 400 (M+1).

TABLE 11

Prepare the following compounds essentially according to the procedure for Example 1.

| Ex No. | Chemical name | Structure and Physical Data MS (m/z) |
|---|---|---|
| 2 | [4-[[4-[[(5-Methylpyrimidin-2-yl)amino]methyl]-2-pyridyl]oxy]phenyl]methane-sulfonamide | 386 (M + 1) |
| 3 | N-Methyl-1-[4-[[4-[[[5-(trifluoromethyl)pyrimidin-2-yl]amino]methyl]-2-pyridyl]oxy]phenyl]methane-sulfonamide | 454 (M + 1) |
| 4 | 1-[4-[[4-[[(5-chloropyrimidin-2-yl)amino]methyl]-2-pyridyl]oxy]-3-fluoro-phenyl]-N-methyl-methanesulfonamide | 438 (M + 1) |
| 5 | 1-[4-[[4-[[(5-chloropyrimidin-2-yl)amino]methyl]-6-methoxy-2-pyridyl]oxy]phenyl]-N-methyl-methanesulfonamide | 450 (M + 1) |
| 6 | [4-[[2-[[(5-ethylpyrimidin-2-yl)amino]methyl]-4-pyridyl]oxy]phenyl]methane-sulfonamide | 400 (M + 1) |
| 7 | [4-[[4-[[(5-ethylpyrimidin-2-yl)amino]methyl]-2-pyridyl]oxy]-3-fluoro-phenyl]methanesulfonamide | 418 (M + 1) |

TABLE 11-continued

Prepare the following compounds essentially according to the procedure for Example 1.

| Ex No. | Chemical name | Structure and Physical Data MS (m/z) |
|---|---|---|
| 8 | 1-[4-[[4-[[(5-Chloropyrimidin-2-yl)amino]methyl]-6-morpholino-2-pyridyl]oxy]phenyl]-N-methyl-methanesulfonamide | 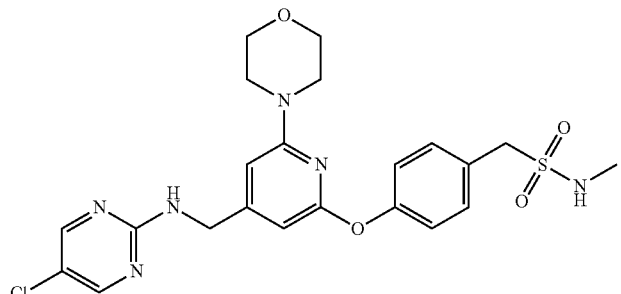<br>505 (M + 1) |
| 9 | 1-[4-[6-[[(5-Chloropyrimidin-2-yl)amino]methyl]-2-ethyl-pyrimidin-4-yl]oxyphenyl]-N-methyl-methanesulfonamide | 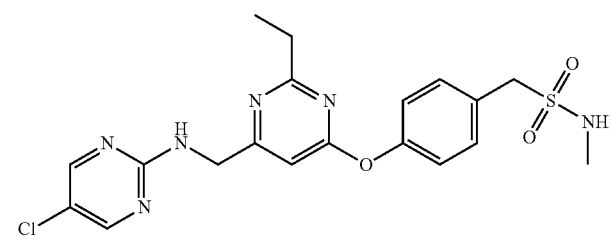 [SMILES: CCc1nc(CNc2ncc(Cl)cn2)cc(Oc2ccc(CS(=O)(=O)NC)cc2)n1]<br>449 (M + 1) |
| 10 | 1-[4-[6-[[(5-Chloropyrimidin-2-yl)amino]methyl]-2-(trifluoromethyl)pyrimidin-4-yl]oxyphenyl]-N-methyl-methanesulfonamide | 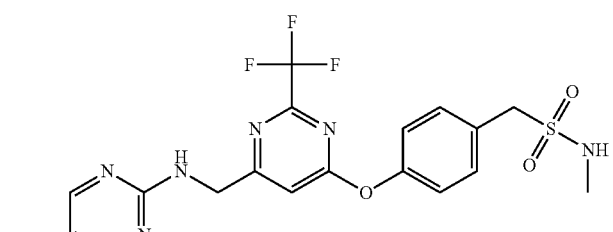<br>489 (M + 1) |
| 11 | 1-[4-[6-[[(5-Ethylpyrimidin-2-yl)amino]methyl]-2-(methoxymethyl)pyrimidin-4-yl]oxyphenyl]-N-methyl-methanesulfonamide | 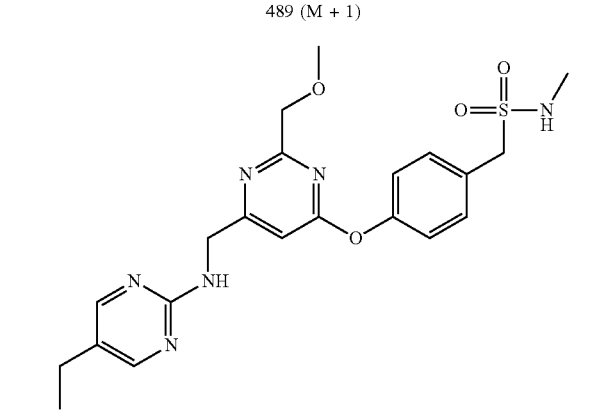<br>459 (M + 1) |
| 12 | [4-[2-Amino-6-[[(5-chloropyrimidin-2-yl)amino]methyl]pyrimidin-4-yl]oxyphenyl]methanesulfonamide | 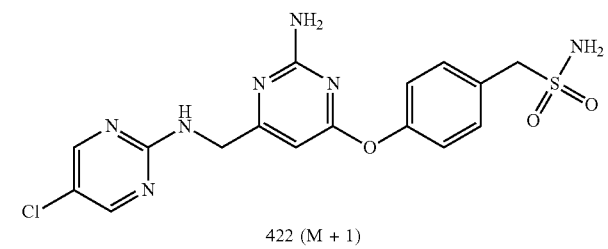<br>422 (M + 1) |

TABLE 11-continued

Prepare the following compounds essentially according to the procedure for Example 1.

| Ex No. | Chemical name | Structure and Physical Data MS (m/z) |
|---|---|---|
| 13 | [4-[6-[[(5-Ethylpyrimidin-2-yl)amino]methyl]-2-methyl-pyrimidin-4-yl]oxyphenyl]methane-sulfonamide | 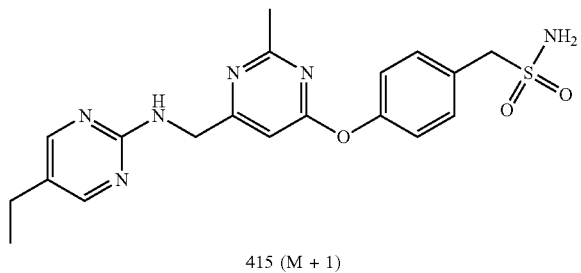<br>415 (M + 1) |
| 14 | [4-[2-Amino-6-[[(5-ethylpyrimidin-2-yl)amino]methyl]pyrimidin-4-yl]oxyphenyl]methane-sulfonamide | 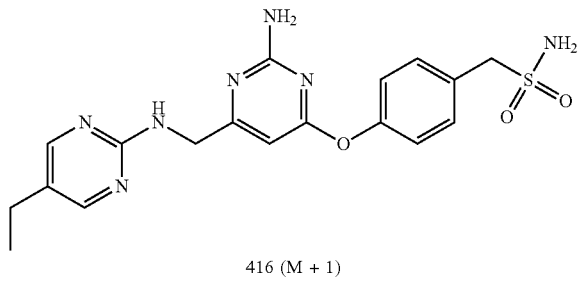<br>416 (M + 1) |
| 15 | 1-[4-[6-[[(5-Chloropyrimidin-2-yl)amino]methyl]-2-methoxy-pyrimidin-4-yl]oxyphenyl]-N-methyl-methanesulfonamide | 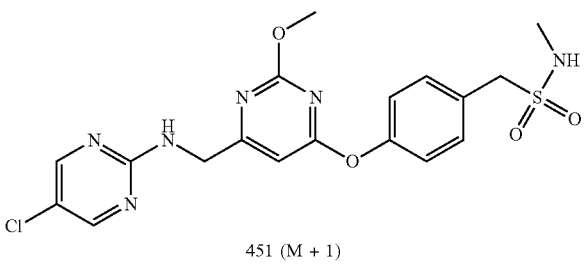<br>451 (M + 1) |
| 16 | 1-[4-[6-[[(5-Chloropyrimidin-2-yl)amino]methyl]-2-methylsulfanyl-pyrimidin-4-yl]oxyphenyl]-N-methyl-methanesulfonamide | 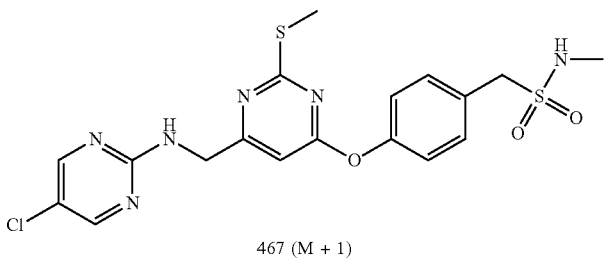<br>467 (M + 1) |
| 17 | 1-[4-[6-[[(5-Chloropyrimidin-2-yl)amino]methyl]-2-cyclopropyl-pyrimidin-4-yl]oxyphenyl]-N-methyl-methanesulfonamide | 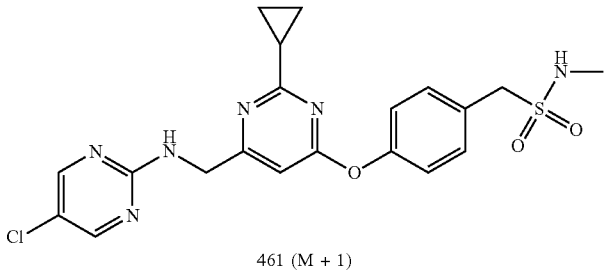<br>461 (M + 1) |

TABLE 11-continued

Prepare the following compounds essentially according to the procedure for Example 1.

| Ex No. | Chemical name | Structure and Physical Data MS (m/z) |
|---|---|---|
| 18 | 1-[4-[2-Cyclopropyl-6-[[(5-ethylpyrimidin-2-yl)amino]methyl]pyrimidin-4-yl]oxyphenyl]-N-methyl-methanesulfonamide | 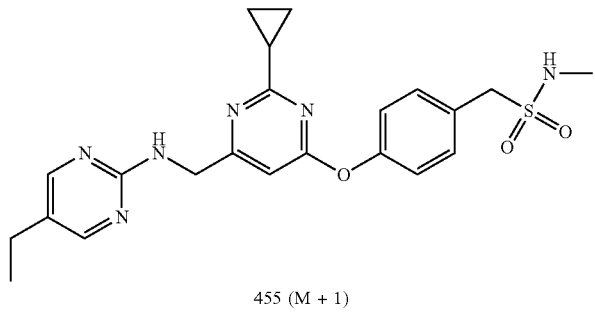<br>455 (M + 1) |
| 19 | 1-[4-[[2-[[(5-Ethylpyrimidin-2-yl)amino]methyl]-4-pyridyl]oxy]phenyl]-N-methyl-methanesulfonamide | 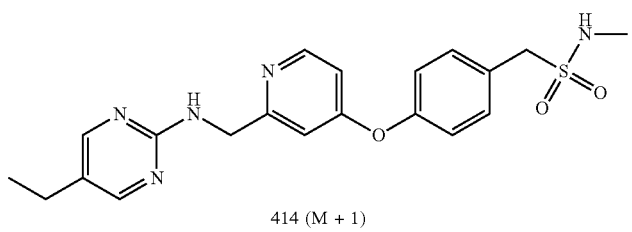<br>414 (M + 1) |
| 20 | 1-[4-[6-[[(5-Ethylpyrimidin-2-yl)amino]methyl]-2-(trifluoromethyl)pyrimidin-4-yl]oxyphenyl]-N-methyl-methanesulfonamide | 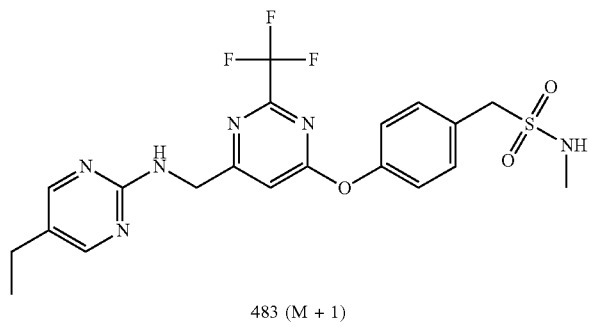<br>483 (M + 1) |
| 21 | [4-[6-[[(5-Chloropyrimidin-2-yl)amino]methyl]-2-(methylamino)pyrimidin-4-yl]oxyphenyl]methane-sulfonamide | 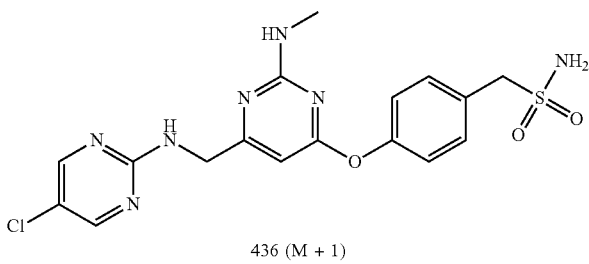<br>436 (M + 1) |
| 22 | [4-[6-[[(5-Chloropyrimidin-2-yl)amino]methyl]-2-(dimethylamino)pyrimidin-4-yl]oxyphenyl]methane-sulfonamide | 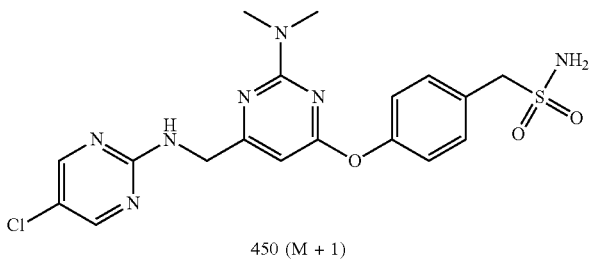<br>450 (M + 1) |

TABLE 11-continued

Prepare the following compounds essentially according to the procedure for Example 1.

| Ex No. | Chemical name | Structure and Physical Data MS (m/z) |
|---|---|---|
| 23 | [4-[6-[[(5-Chloropyrimidin-2-yl)amino]methyl]-2-morpholino-pyrimidin-4-yl]oxyphenyl]methanesulfonamide | 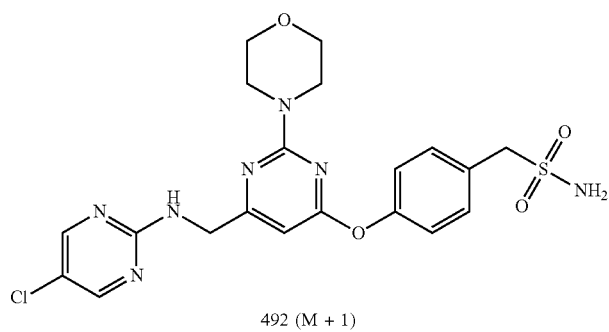<br>492 (M + 1) |
| 24 | [4-[6-[[(5-Chloropyrimidin-2-yl)amino]methyl]-2-(4-methylpiperazin-1-yl)pyrimidin-4-yl]oxyphenyl]methane-sulfonamide | 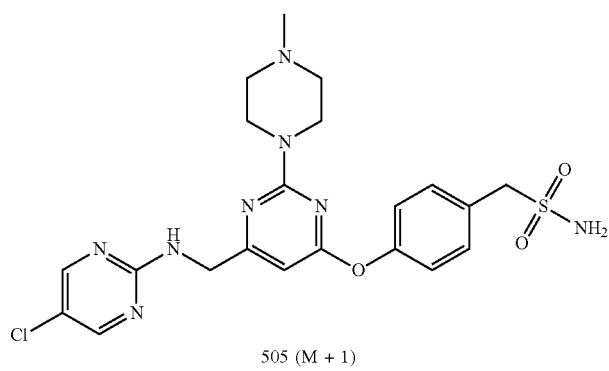<br>505 (M + 1) |
| 25 | Racemic [4-[6-[1-[(5-Ethylpyrimidin-2-yl)amino]ethyl]-2-methyl-pyrimidin-4-yl]oxyphenyl]methane-sulfonamide | 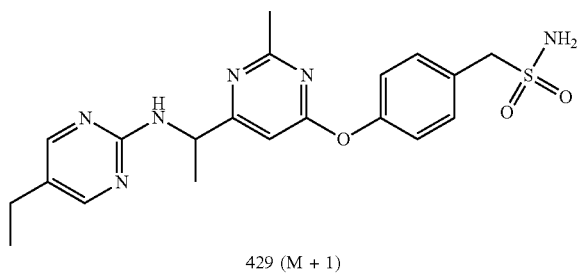<br>429 (M + 1) |
| 26 | Racemic [4-[6-[1-[(5-Ethylpyrimidin-2-yl)amino]ethyl]-2-methyl-pyrimidin-4-yl]oxyphenyl]methane-sulfonamide | 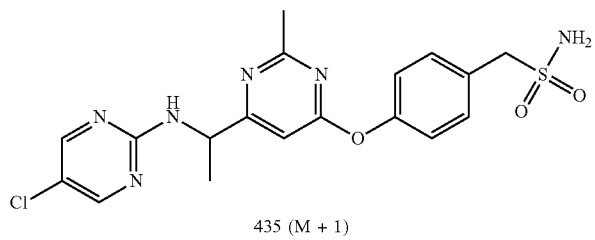<br>435 (M + 1) |

TABLE 11-continued

Prepare the following compounds essentially according to the procedure for Example 1.

| Ex No. | Chemical name | Structure and Physical Data MS (m/z) |
|---|---|---|
| 27 | 1-[4-[[4-[[(5-Ethylpyrimidin-2-yl)amino]methyl]-2-pyridyl]oxy]phenyl]-N-methyl-methanesulfonamide | 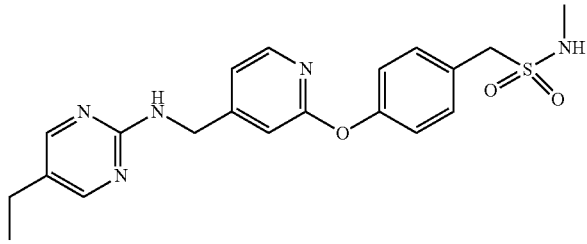 [SMILES: CCc1cnc(NCc2ccnc(Oc3ccc(CS(=O)(=O)NC)cc3)c2)nc1]<br>414 (M + 1) |
| 28 | 1-[4-[6-[[(5-Ethylpyrimidin-2-yl)amino]methyl]-2-methyl-pyrimidin-4-yl]oxyphenyl]-N-methyl-methanesulfonamide | 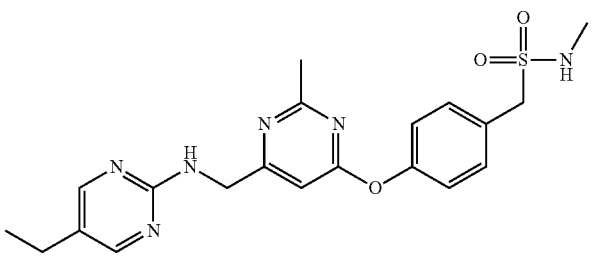 [SMILES: CCc1cnc(NCc2cc(Oc3ccc(CS(=O)(=O)NC)cc3)nc(C)n2)nc1]<br>429 (M + 1) |

Example 29

1-[4-[[4-[[(5-Methoxypyrimidin-2-yl)amino]methyl]-2-pyridyl]oxy]phenyl]-N-methyl-methanesulfonamide

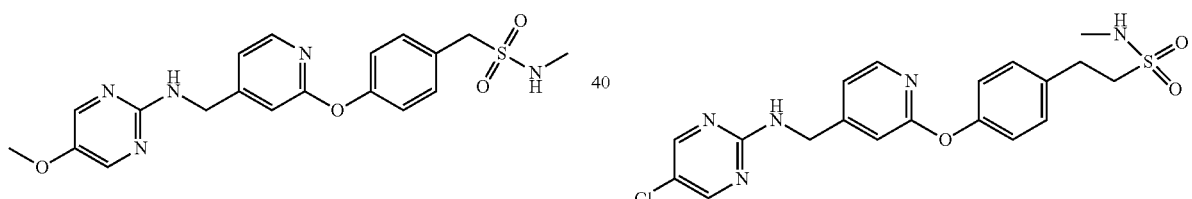

Combine 1-[4-[(4-formyl-2-pyridyl)oxy]phenyl]-N-methyl-methanesulfonamide (154 mg, 0.502 mmol), dichloromethane (5 mL), and methanol (3.35 mL), under a nitrogen atmosphere. Add 5-methoxypyrimidin-2-amine (69 mg, 0.55 mmol) and scandium (III) triflate (12 mg, 0.025 mmol). Stir the mixture at ambient temperature for 1.5 hours then pour it into a saturated aqueous solution of sodium bicarbonate. Extract with dichloromethane, collect the organic extracts; dry over MgSO$_4$, filter, collect the filtrate; and concentrate the filtrate under reduced pressure to provide a residue. Dissolve the residue in dichloromethane (5 mL); then add acetic acid (0.3 mL, 5 mmol) and sodium triacetoxyborohydride (168 mg, 0.754 mmol). Stir the resulting mixture at ambient temperature overnight. Pour the mixture into a saturated aqueous solution of sodium bicarbonate, extract with dichloromethane, collect the organic extracts; dry the over MgSO$_4$; filter; collect the filtrate; and concentrate the filtrate under reduced pressure to provide the crude product. Purify the product via reverse phase chromatography to afford the title compound (63.7 mg, 28.5%). MS (m/z): 416 (M+1).

Example 30

2-[4-[[4-[[(5-Chloropyrimidin-2-yl)amino]methyl]-2-pyridyl]oxy]phenyl]-N-methyl-ethanesulfonamide Combine 5-chloro-N-[(1-oxidopyridin-1-ium-4-yl)methyl]pyrimidin-2-amine (410 mg, 1.73 mmol), 2-(4-hydroxyphenyl)-N-methylethanesulfonamide (513 mg, 1.91 mmol), diisopropylethylamine (1.13 mL, 6.5 mmol), and bromo-tris-pyrrolidinophosphonium hexafluorophosphate (1.05 g, 2.25 mmol) in dry dichloromethane (5.2 mL). Stir the mixture for 3 hrs at ambient temperature. Remove the solvents under reduced pressure to provide a residue. Subject the residue to strong cation exchange chromatography eluting with 7N ammonia in methanol. Combine desired fractions and remove solvents under reduced pressure to provide the crude title compound. Purify the title compound using reverse phase HPLC eluting with a gradient of 23-57% of (10 mM NH$_4$HCO$_3$) in acetonitrile. Combine the appropriate fractions and remove the solvents under reduced pressure to provide the title compound as a solid. (369 mg, 46.6%). MS (m/z): 434 (M+1).

TABLE 12

Prepare the following compounds essentially according to the procedure for Example 30.

| Ex. No. | Chemical name | Structure and Physical Data MS (m/z) |
|---|---|---|
| 31 | 1-[4-[[4-[[[5-(Difluoromethyl)pyrimidin-2-yl]amino]methyl]-2-pyridyl]oxy]phenyl]-N-methyl-methanesulfonamide | 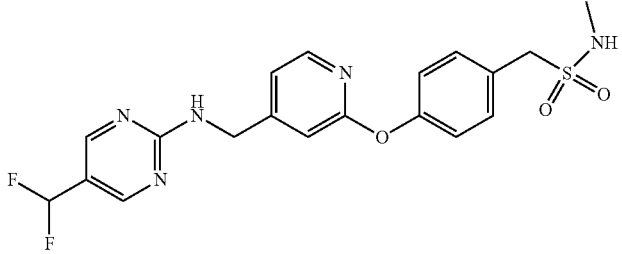 [SMILES: CNS(=O)(=O)Cc1ccc(Oc2cc(CNc3ncc(C(F)F)cn3)ccn2)cc1]<br>436 (M + 1) |
| 32 | [4-[[4-[1-[(5-Chloropyrimidin-2-yl)amino]ethyl]-2-pyridyl]oxy]phenyl]methane-sulfonamide Isomer 2* | 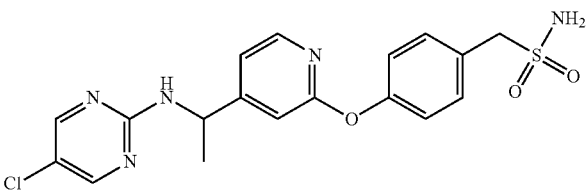 [SMILES: CC(Nc1ncc(Cl)cn1)c1ccnc(Oc2ccc(CS(N)(=O)=O)cc2)c1]<br>420 (M + 1) |

*Chiral Purification Conditions for Ex 32: Chiralpak AS (10 uM, 2 × 25 cm) column; Elution: isocratic in 0.2% dimethylethanolamine in methanol @ 15 mL/min.

Example 33

(2R)—N-[2-[4-[[4-[[(5-Ethylpyrimidin-2-yl)amino]methyl]-2-pyridyl]oxy]phenyl]ethyl]-2-hydroxy-propanamide

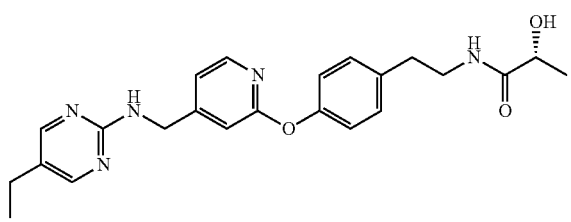 [SMILES: CCc1cnc(NCc2ccnc(Oc3ccc(CCNC(=O)[C@@H](C)O)cc3)c2)nc1]

Combine D-lactic acid (64.5 mg, 0.608 mmol), diisopropylethylamine (472 mg, 0.636 mmol) and N-[[2-[4-(2-aminoethyl)phenoxy]-4-pyridyl]methyl]-5-ethyl-pyrimidin-2-amine (250 mg, 0.608 mmol) in tetrahydrofuran (2.43 mL). Cool the mixture to −20° C. and add 1-[Bis(dimethylamino)methylene]-1H-1,2,3-triazolo[4,5-b]pyridinium 3-oxide hexafluorophosphate (277 mg, 0.730 mmol), remove the cooling bath and allow the reaction to warm to ambient temperature then stir overnight. Remove the solvents under reduced pressure. Purify the crude product via strong cation exchange chromatography using 7N ammonia in methanol to elute the product. Combine desired fractions and remove solvents under reduced pressure to provide a residue. Subject the residue to reverse phase prep HPLC eluting with a gradient of 10-100% of [10 mM $NH_4HCO_3$ (aq.) in acetonitrile. Collect and combine the appropriate fractions and remove solvents under reduced pressure to provide the title compound (63.5 mg, 23.8%). MS (m/z): 422 (M+1).

TABLE 13

Prepare the following compounds essentially according to the procedure for Example 33.

| Ex No. | Chemical name | Structure and Physical Data MS (m/z) |
|---|---|---|
| 34 | (2S)-N-[2-[4-[[4-[[(5-Ethylpyrimidin-2-yl)amino]methyl]-2-pyridyl]oxy]phenyl]ethyl]-2-hydroxy-propanamide | 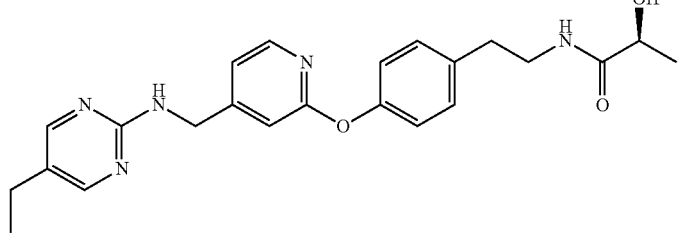<br>422 (M + 1) |

TABLE 13-continued

Prepare the following compounds essentially according to the procedure for Example 33.

| Ex No. | Chemical name | Structure and Physical Data MS (m/z) |
|---|---|---|
| 35 | N-[2-[4-[[4-[[(5-Chloropyrimidin-2-yl)amino]methyl]-2-pyridyl]oxy]phenyl]ethyl]-2-methoxy-acetamide | 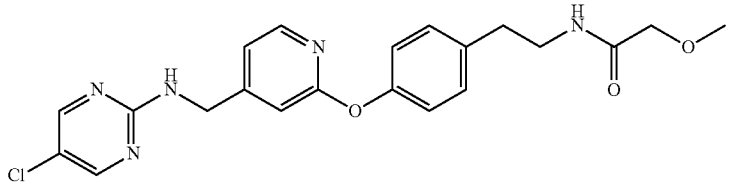 [SMILES: COCC(=O)NCCc1ccc(Oc2cc(CNc3ncc(Cl)cn3)ccn2)cc1]<br>428 (M + 1) |
| 36 | N-[[4-[[4-[[(5-Chloropyrimidin-2-yl)amino]methyl]-6-methyl-2-pyridyl]oxy]phenyl]methyl]-2-hydroxy-acetamide | 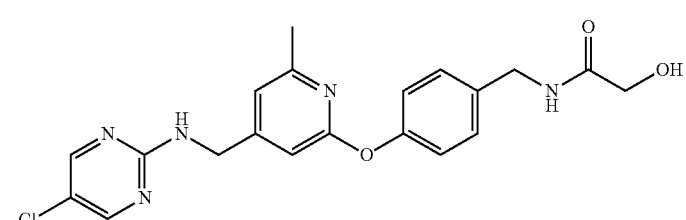<br>414 (M + 1) |

Example 37

1-[2-[4-[[4-[[(5-Chloropyrimidin-2-yl)amino]methyl]-6-[(4-methoxyphenyl)methylamino]-2-pyridyl]oxy]phenyl]ethyl]-3-methyl-urea

Example 38

2-amino-4-[[(5-chloropyrimidin-2-yl)amino]methyl]-6-[4-[2-(sulfamoylamino)ethyl]phenoxy]pyrimidine

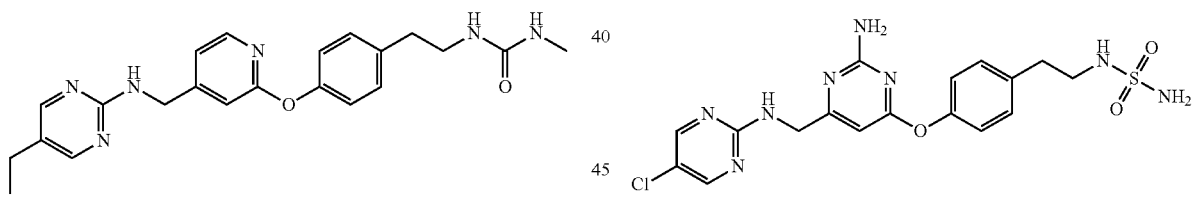

Combine N-[[2-[4-(2-aminoethyl)phenoxy]-4-pyridyl]methyl]-5-ethyl-pyrimidin-2-amine (200 mg, 0.459 mmol) and trimethylamine (0.077 mL) in dichloromethane (0.229 mL). Cool the mixture to 0° C. and add methylcarbamoyl chloride (64.2 mg, 0.687 mmol). Allow the mixture to warm to ambient temperature and stir for 2 hours. Quench the reaction with NaHCO₃ (aqueous, saturated) to pH=8. Extract with dichloromethane; combine the organic extracts; wash with water and brine; dry over Na₂SO₄, filter, collect the filtrate; and remove the solvents under reduced pressure to provide the crude product. Purify the crude product via reverse phase HPLC using a gradient of 10-100% of [10 mM NH₄HCO₃ (aq.) in acetonitrile] over 2 minutes. Collect and combine the appropriate fractions and remove solvents under reduced pressure to provide the title compound (80 mg, 44%). MS (m/z): 407 (M+1).

Charge a pressure tube with 4-[4-(2-aminoethyl)phenoxy]-6-[[(5-chloropyrimidin-2-yl)amino]methyl]pyrimidin-2-amine (185 mg, 0.498 mmol), sulfuric diamide (239 mg, 2.49 mmol) and 1,4-dioxane (5.5 mL). Seal and heat the tube to 100° C. for 7 hours and then cool to ambient temperature. Remove solvent under reduced pressure and partition the residue between ethyl acetate and water. Separate the layers, wash the organic fraction with brine; dry over MgSO₄; filter; collect the filtrate; and remove solvents under reduced pressure to provide a residue. Subject the residue to reverse phase HPLC eluting with a gradient of 10-100% of 10 mM NH₄HCO₃ (aq.) in acetonitrile over 2 minutes. Collect and combine the appropriate fractions and remove solvents under reduced pressure to provide the title compound (57 mg, 25%). MS (m/z): 451 (M+1).

TABLE 14

Prepare the following compounds essentially according to the procedure for Example 38.

| Ex No. | Chemical name | Structure and Physical Data MS (m/z) |
|---|---|---|
| 39 | 4-[[(5-Chloropyrimidin-2-yl)amino]methyl]-6-[4-[2-(sulfamoylamino)ethyl]phenoxy]-pyrimidine | 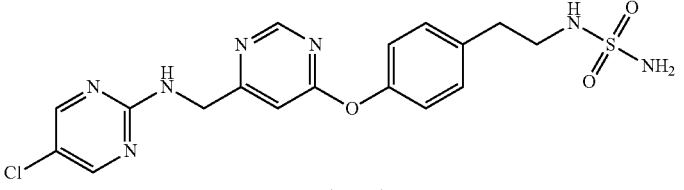 [SMILES: NS(=O)(=O)NCCc1ccc(Oc2cc(CNc3ncc(Cl)cn3)ncn2)cc1] 436 (M + 1) |
| 40 | 4-[[(5-Chloropyrimidin-2-yl)amino]methyl]-2-methyl-6-[4-[2-(sulfamoylamino)ethyl]phenoxy]-pyrimidine | 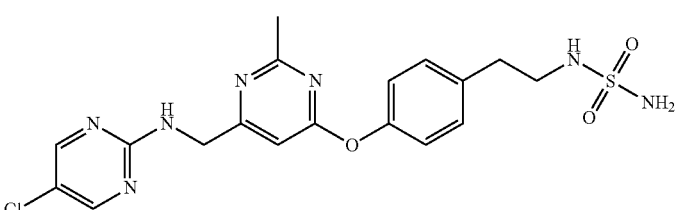 450 (M + 1) |
| 41 | 2-Amino-4-[[(5-ethylpyrimidin-2-yl)amino]methyl]-6-[4-[2-(sulfamoylamino)ethyl]phenoxy]-pyrimidine | 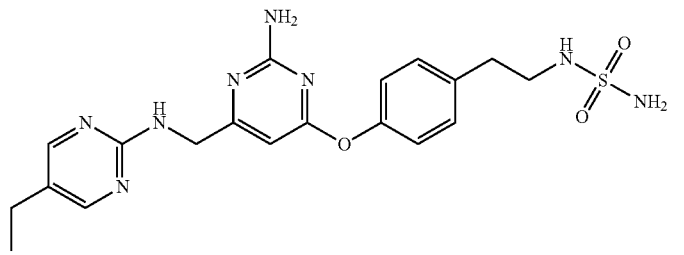 [SMILES: CCc1cnc(NCc2cc(Oc3ccc(CCNS(N)(=O)=O)cc3)nc(N)n2)nc1] 445 (M + 1) |
| 42 | 5-Chloro-N-[[2-methyl-6-[4-[2-(methylsulfamoylamino)ethyl]phenoxy]-pyrimidin-4-yl]methyl]pyrimidin-2-amine | 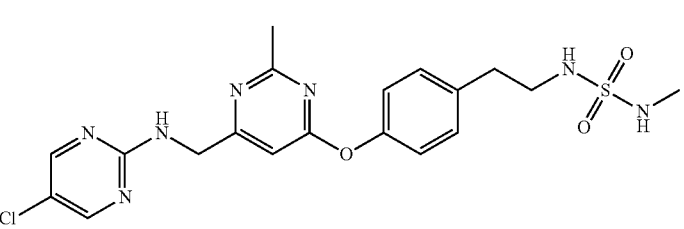 [SMILES: CNS(=O)(=O)NCCc1ccc(Oc2cc(CNc3ncc(Cl)cn3)nc(C)n2)cc1] 464 (M + 1) |

Example 43

N-[2-[4-[2-Amino-6-[[(5-chloropyrimidin-2-yl)amino]methyl]pyrimidin-4-yl]oxyphenyl]ethyl]methanesulfonamide

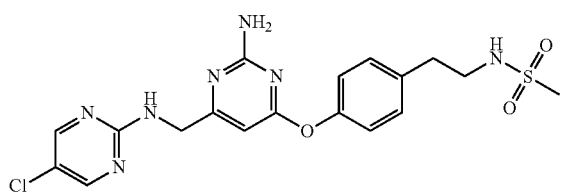 [SMILES: CS(=O)(=O)NCCc1ccc(Oc2cc(CNc3ncc(Cl)cn3)nc(N)n2)cc1]

Combine 4-[4-(2-aminoethyl)phenoxy]-6-[[(5-chloropyrimidin-2-yl)amino]methyl]pyrimidin-2-amine (260 mg, 0.601 mmol) and triethylamine (121 mg, 1.20 mmol) in dichloromethane (3.6 mL). Cool the mixture to 0° C. and stir for 5 min, then add methanesulfonyl chloride (82.6 mg, 0.721 mmol) and stir for 10 min while maintaining the mixture at 0° C. Quench the reaction with water and extract with dichloromethane. Combine organic extracts; wash with water then brine; dry over Na₂SO₄, filter; collect the filtrate; and concentrate the filtrate under reduced pressure to provide a residue. Subject the residue to reverse phase prep HPLC eluting with a gradient of 10-100% of 10 mM NH₄HCO₃ (aq.) in acetonitrile over 6 minutes. Collect and combine the appropriate fractions. Remove solvents under reduced pressure to provide the title compound (27 mg, 10%). MS (m/z) 450 (M+1).

TABLE 15

Prepare the following compounds essentially according to the procedure for Example 43.

| Ex No. | Chemical name | Structure and Physical Data MS (m/z) |
|---|---|---|
| 44 | N-[2-[4-[6-[[(5-Ethylpyrimidin-2-yl)amino]methyl]-2-methyl-pyrimidin-4-yl]oxyphenyl]ethyl]methanesulfonamide | 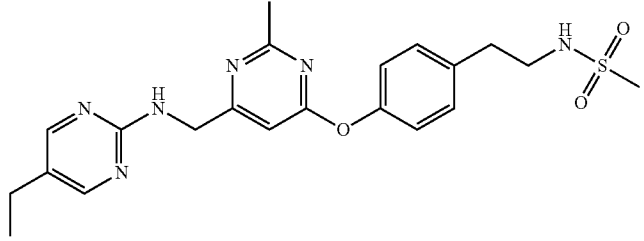 [SMILES: CCc1cnc(NCc2cc(Oc3ccc(CCNS(C)(=O)=O)cc3)nc(C)n2)nc1]<br>443 (M + 1) |
| 45 | N-[2-[4-[[4-[[(5-Chloropyrimidin-2-yl)amino]methyl]-2-pyridyl]oxy]phenyl]ethyl]methanesulfonamide | 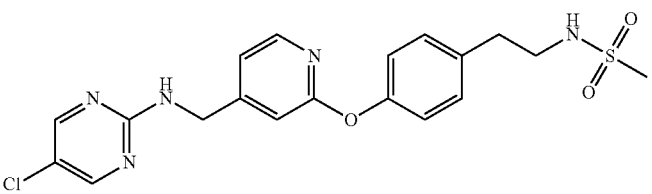 [SMILES: CS(=O)(=O)NCCc1ccc(Oc2cc(CNc3ncc(Cl)cn3)ccn2)cc1]<br>434 (M + 1) |

Example 46

Methyl N-[2-[4-[6-[[(5-chloropyrimidin-2-yl)amino]methyl]-2-methyl-pyrimidin-4-yl]oxyphenyl]ethyl]acetamide

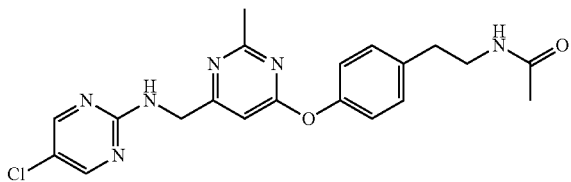 [SMILES: CC(=O)NCCc1ccc(Oc2cc(CNc3ncc(Cl)cn3)nc(C)n2)cc1]

Combine N-[[6-[4-(2-aminoethyl)phenoxy]-2-methyl-pyrimidin-4-yl]methyl]-5-chloro-pyrimidin-2-amine (350 mg, 0.708 mmol) and triethylamine (143 mg, 1.4 mmol) in dichloromethane (2.4 mL). Cool the mixture to 0° C. and stir for 5 min. Add acetyl chloride (0.0605 mL, 0.849 mmol) and stir for 30 min while maintaining the mixture at 0° C. Allow the mixture to warm to ambient temperature and stir for an additional 2 hours. Quench the reaction with aqueous NaHCO₃ and extract with dichloromethane. Combine the organic extracts; wash with water; and dry over Na₂SO₄; filter; collect the filtrate; and concentrate the filtrate to provide a residue. Subject the residue to reverse phase HPLC eluting with a gradient of 10-100% of 10 mM NH₄HCO₃ in acetonitrile. Combine the appropriate fractions and remove the solvents under reduced pressure to provide the title compound as a white solid (182 mg, 62.3%). MS (m/z): 413 (M+1).

TABLE 16

Prepare the following compounds essentially according to the procedure for Example 46.

| Ex No. | Chemical name | Structure and Physical Data MS (m/z) |
|---|---|---|
| 47 | N-[2-[4-[2-Amino-6-[[(5-chloropyrimidin-2-yl)amino]methyl]pyrimidin-4-yl]oxyphenyl]ethyl]acetamide | 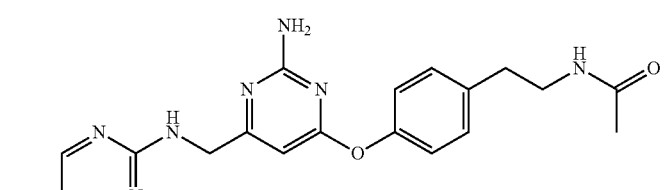<br>414 (M + 1) |

TABLE 16-continued

Prepare the following compounds essentially according to the procedure for Example 46.

| Ex No. | Chemical name | Structure and Physical Data MS (m/z) |
|---|---|---|
| 48 | N-[2-[4-[6-[[(5-Ethylpyrimidin-2-yl)amino]methyl]-2-methyl-pyrimidin-4-yl]oxyphenyl]ethyl]acetamide | 407 (M + 1) |
| 49 | N-[2-[4-[[4-[[(5-Chloropyrimidin-2-yl)amino]methyl]-2-pyridyl]oxy]phenyl]-1-methyl-ethyl]acetamide Isomer 2* | 412 (M + 1) |

*Chiral Purification Conditions for Example 49: Chiralpak AS-H column; Elution: 40% (0.2% dimethylethanolamine in methanol) in $CO_2$ @ 130 mL/min.

Example 50

1-[4-[[6-Amino-4-[[(5-chloropyrimidin-2-yl)amino]methyl]-2-pyridyl]oxy]phenyl]-N-methyl-methane-sulfonamide

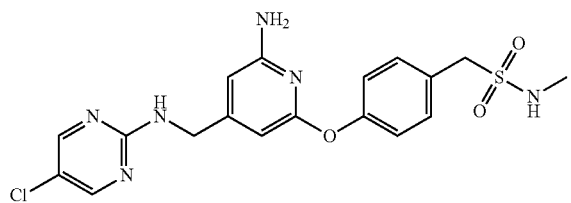 [SMILES: CNS(=O)(=O)Cc1ccc(Oc2cc(CNc3ncc(Cl)cn3)cc(N)n2)cc1]

Dissolve 1-[4-[[4-[[(5-chloropyrimidin-2-yl)amino]methyl]-6-[(4-methoxyphenyl)methylamino]-2-pyridyl]oxy]phenyl]-N-methyl-methanesulfonamide (238 mg, 0.43 mmol) in 10 mL trifluoroacetic acid and stir at 80° C. After 1 hour, cool to ambient temperature and remove solvents under reduced pressure. Add ethyl acetate and wash the solution with $NaHCO_3$ (aq.). Wash with brine, dry over $Na_2SO_4$, filter, collect the filtrate, and concentrate under reduced pressure. Subject the residue to silica gel chromatography eluting with gradient of 5-50% (10% 2M $NH_3$/methanol in dichloromethane) in dichloromethane. Combine the desired fractions and remove the solvents under reduced pressure to provide the title compound as a white solid (157 mg, 84.2%). MS (m/z): 435 (M+1).

TABLE 17

Prepare the following compounds essentially according the process for Example 50.

| Ex No | Chemical name | Structure and Physical Data MS (m/z) |
|---|---|---|
| 51 | [4-[[6-Amino-4-[[(5-chloropyrimidin-2-yl)amino]methyl]-2-pyridyl]oxy]phenyl]methanesulfonamide | 421 (M + 1) |

TABLE 17-continued

Prepare the following compounds essentially according the process for Example 50.

| Ex No | Chemical name | Structure and Physical Data MS (m/z) |
|---|---|---|
| 52 | [4-[[6-Amino-4-[[(5-ethylpyrimidin-2-yl)amino]methyl]-2-pyridyl]oxy]phenyl]methanesulfonamide | 415 (M + 1) |
| 53 | 1-[2-[4-[[6-Amino-4-[[(5-chloropyrimidin-2-yl)amino]methyl]-2-pyridyl]oxy]phenyl]ethyl]-3-methyl-urea | 428 (M + 1) |
| 54 | 2-[[2-Amino-6-[4-[2-(sulfamoylamino)ethyl]phenoxy]-4-pyridyl]methylamino]-5-ethyl-pyrimidine | 444 (M + 1) |
| 55 | N-[2-[4-[2-Amino-6-[[(5-ethylpyrimidin-2-yl)amino]methyl]pyrimidin-4-yl]oxyphenyl]ethyl]acetamide | 408 (M + 1) |
| 56 | 2-[[2-Amino-6-[4-[2-(sulfamoylamino)propyl]phenoxy]-4-pyridyl]methylamino]-5-ethyl-pyrimidine Isomer 2* | 458 (M + 1) |

TABLE 17-continued

Prepare the following compounds essentially according the process for Example 50.

| Ex No | Chemical name | Structure and Physical Data MS (m/z) |
|---|---|---|
| 57 | N-[2-[4-[2-Amino-6-[[(5-ethylpyrimidin-2-yl)amino]methyl]pyrimidin-4-yl]oxyphenyl]ethyl]methanesulfonamide | 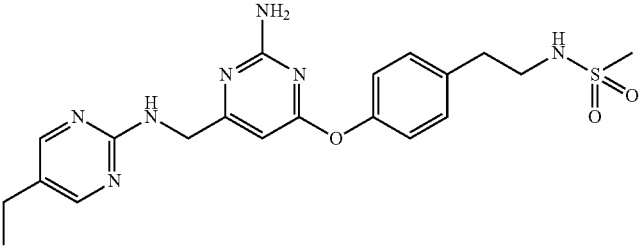 [SMILES: CCc1cnc(NCc2cc(Oc3ccc(CCNS(C)(=O)=O)cc3)nc(N)n2)nc1]<br>444 (M + 1) |

*Chiral [purification conditions for Example 56: Chiralpak AS (5 uM, 2 * 25 cm) column; Elution: 30% (0.2% dimethylethanolamine in Methanol) in CO2 @ 65 mL/min.

Example 58

1-[4-[6-[[(5-Chloropyrimidin-2-yl)amino]methyl]-2-cyano-pyrimidin-4-yl]oxyphenyl]-N-methyl-methanesulfonamide

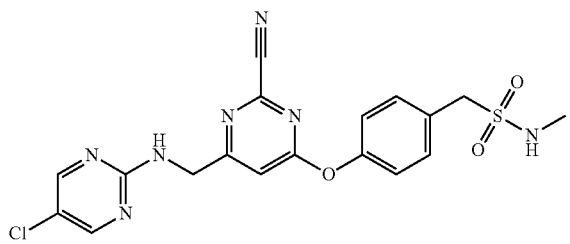 [SMILES: CNS(=O)(=O)Cc1ccc(Oc2cc(CNc3ncc(Cl)cn3)nc(C#N)n2)cc1]

Combine 1-[4-[6-[[(5-chloropyrimidin-2-yl)amino]methyl]-2-methylsulfonyl-pyrimidin-4-yl]oxyphenyl]-N-methyl-methanesulfonamide (250 mg, 0.501 mmol) and potassium cyanide (65.2 mg, 1.00 mmol) in DMSO (20 mL). Stir the resulting mixture at ambient temperature for 30 min. Quench with water and extract with ethyl acetate. Collect the ethyl acetate extracts, remove the solvents under reduced pressure to provide a residue. Subject the residue to reverse phase flash column chromatography (100 g C18 gold column) eluting with a gradient of 20-90% acetonitrile in aqueous $NH_4HCO_3$. Combine the appropriate fractions and remove the solvents under reduced pressure to give the title compound (0.116 g, 51.9%). MS (m/z): 446 (M+1).

Example 59

1-[4-[2-Amino-6-[[(5-chloropyrimidin-2-yl)amino]methyl]pyrimidin-4-yl]oxyphenyl]-N-methyl-methanesulfonamide

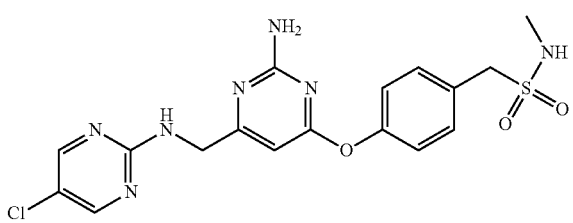 [SMILES: CNS(=O)(=O)Cc1ccc(Oc2cc(CNc3ncc(Cl)cn3)nc(N)n2)cc1]

Dissolve 1-[4-[6-[[(5-chloropyrimidin-2-yl)amino]methyl]-2-methylsulfonyl-pyrimidin-4-yl]oxyphenyl]-N-methyl-methanesulfonamide (200 mg, 0.401 mmol) in 0.5M ammonia in dioxanes (8.02 mL, 4.01 mmol) and stir at ambient temperature overnight. Add additional ammonia in dioxanes (0.5 M, 10 mL) stir for one hour at ambient temperature, then heat via microwave 120° C. for 30 minutes, followed by heating for one hour at 90° C. and then 1 hour at 100° C. Purify via silica gel chromatography using a gradient of 0-10% methanol in dichloromethane to elute the product. Combine the appropriate fractions and remove solvents under reduced pressure to give the title product (196 mg, 72%). MS (m/z): 436 (M+1).

Example 60

[4-[[6-Amino-4-[[(5-ethylpyrimidin-2-yl)amino]methyl]-2-pyridyl]oxy]phenyl]methanesulfonamide; hydrochloride

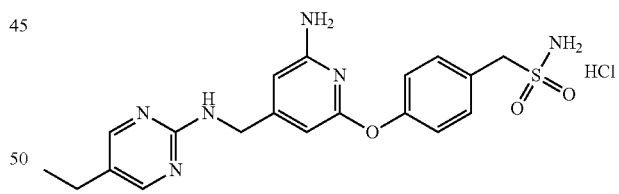

Dissolve [4-[[6-amino-4-[[(5-ethylpyrimidin-2-yl)amino]methyl]-2-pyridyl]oxy]phenyl]methanesulfonamide (1.3 g, 3.14 mmol) in ethyl acetate (50 mL). Add HCl (4M in dioxanes, 2.0 mL, 8.0 mmol) and stir the resulting suspension for one hour. Filter and rinse solids with additional ethyl acetate, then dry under reduced pressure at 50° C. Add the solid to ethanol (50 mL) and heat to 80° C. with sonication for 10 minutes. Filter and rinse the filter paper with 25 mL hot ethanol. Collect the filtrate and allow it to sit at room temperature until crystals form. Collect the solid material to provide the title product as a white solid (140 mg, 31%). MS (m/z): 415 (M-HCl+1).

Example 61

[4-[6-[[(5-Chloropyrimidin-2-yl)amino]methyl]-2-piperazin-1-yl-pyrimidin-4-yl]oxyphenyl]methanesulfonamide

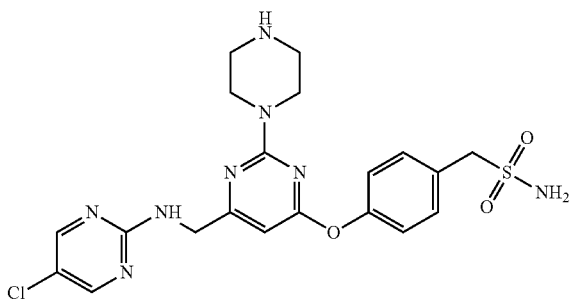 [SMILES: NS(=O)(=O)Cc1ccc(Oc2cc(CNc3ncc(Cl)cn3)nc(N3CCNCC3)n2)cc1]

Dissolve tert-butyl 4-[4-[[(5-chloropyrimidin-2-yl)amino]methyl]-6-[4-(sulfamoylmethyl)phenoxy]pyrimidin-2-yl]piperazine-1-carboxylate (1.44 g, 2.44 mmol) in 20 mL methanol and add HCl (4M in 1,4-dioxane, 6.09 mL, 24.4 mmol). Stir the mixture for 2 hr at ambient temperature. Remove solvent under reduced pressure. Dissolve the residue in dichloromethane. Add NaHCO$_3$ (aq., sat'd) until product precipitates from mixture. Remove organic solvents under reduced pressure. Filter on a sintered glass funnel to collect the solid. Dry the solid overnight at 60° C. under reduced pressure to give the title product as a white powder (0.990 g, 82.8%). MS (m/z): 491 (M+1).

GENERAL BIOLOGY

Atherosclerotic vascular disease remains one of the leading causes of mortality and morbidity in industrial societies. One of the well-understood risk factors for that disease is a high concentration of Low Density Lipoprotein (LDL) cholesterol in circulation. Despite the availability of multiple classes of therapeutic agents that lower LDL cholesterol, including the leading therapeutic class, statins, the incidence of major cardiovascular events remains high in the patients with Coronary Heart Disease (CHD). In addition, there is a subset of patients that are intolerant to the most effective therapy, statins (Gotto, A. M., and Moon, J. E., Nature Rev. Cardiol., (2013) 10:560-570). Compounds from that class lower LDL cholesterol, chiefly by up regulation of the LDL receptor and subsequent re-uptake of LDL into the liver. An alternative, and potentially equally effective method, would be lowering of the secretion of Very Low Density Lipoproteins (VLDL), which eventually are converted into LDL in circulation. Two new classes of therapeutic agents, inhibitor of Microsomal Triglyceride Transfer Protein (MTP), lomitapide, and inhibitor of synthesis of ApoB, mipomersen, both of which reduce secretion of VLDL, were shown to reduce LDL cholesterol. However, each of those agents is associated with adverse events, which limits their utility. In particular, therapy with lomitapide is associated with 8-fold increase in the liver fat content. In contrast, inhibition of DGAT2 will reduce production of triglycerides in the liver, which in turn will lead to reduction of VLDL secretion and subsequent lowering of LDL cholesterol. Moreover, scientific statement from the American Heart Association supports therapeutic targeting of elevated triglycerides as means to reduce residual cardiovascular risk (Miller, M. et al, Circulation (2011) 123:2292-2333. Inhibition of DGAT2 will lower circulating triglycerides and thus provide additional protection from cardiovascular events.

Diacylglycerol Acyltransferase 2 (DGAT2) Biochemical Assay

The in vitro inhibitory activity of compounds against human DGAT2 is evaluated in this assay. The assay uses recombinant human DGAT2 with a FLAG tag at the amino terminus, expressed in genetically engineered insect SF9 cells, and purified through affinity chromatography.

DGAT2 catalyzes transfer of an acyl moiety from acyl-Coenzyme A onto diacylglycerol, to form triacylglycerol. In this particular embodiment of the assay oleate is used as the acyl moiety that is transferred. To facilitate miscibility of all lipid components, all lipids used in the assay contain oleyl moiety as the only acyl group.

Prior to starting the assay prepare a mixture of dioleoyl glycerol (DOG) and dioleoyl phosphatidylcholine (DOPC) at 3:7 molar ratio. Mix appropriate amount of DOPC and DOG dissolved in chloroform in a borosilicate glass test tube. Evaporate the solvent under stream of argon to form a film of lipid. Subsequently, place the test-tube under vacuum (<1 Torr) for 2 hrs to remove residual solvent. Add appropriate amount of buffer containing TrisHCl (pH 7.5, 150 mM), and sucrose (250 mM) to achieve 20 mM concentration of total lipid. Assure complete suspension of the lipid film by vigorous vortexing. Sonicate the contents of the tube in a water bath sonicator under standing wave conditions until the suspension turns from turbid to translucent, to assure conversion of liposomes into small unilamellar vesicles (SUVs)

Prepare the test compound by dissolving it and serially diluting in half-log increments in DMSO. For each concentration, perform 10-fold step dilution of compound solution in DMSO into buffer containing TrisHCl (pH 7.5, 150 mM), and sucrose (250 mM).

Mix SUV suspensions and compound solution with other components of the assay to achieve the following concentration of individual ingredients: TrisHCl (pH 7.5, 150 mM), sucrose (250 mM), MgCl$_2$ (5 mM,), dithiothreitol (DTT) (0.5 mM), oleoyl coenzyme A (oleoyl-CoA) (12 µM), 1-$^{14}$C oleoyl coenzyme A (oleyl-CoA-$^{14}$C) (8 µM), dioleoyl glycerol (DOG) (0.6 mM), and dioleoyl phosphatidylcholine (DOPC) (1.4 mM), DGAT2 protein (0.5 nM), DMSO (1%, v/v), with test compound concentration within a 1 nM to 100 µM range, in 30 µl total volume. Incubate the reaction for 1 hr at RT (approximately 21° C.) in individual wells of a 384-well plate. After 1 hr, stop the reaction by adding 23 µl stop solution containing a mixture of isopropanol:EtOH:heptane:DI water:1 N NaOH (59:12.5:15:11:2.5, by volume). Add 42 µL Microscint E and then incubate mixture overnight to extract the triglyceride into the organic solvent layer containing scintillant. Measure the radioactivity using a Perkin-Elmer TopCount instrument. Establish a background measurement for the reaction by repeating the above procedure, but without including enzyme or the test compound in the reaction mixture. Calculate the degree of inhibition of DGAT2 by measuring the radioactivity at 10 different concentrations for each compound. Determine the IC$_{50}$ for each compound using 4 parameter logistic curve fit. All the compounds of the Examples listed herein exhibit an IC$_{50}$ less than 1500 nM. The geometric mean for the calculated IC$_{50}$ values for the compounds of Examples 7, 10, 24, and 57 and are listed in Table 18. The data listed in Table 18 demonstrate that the compounds of Examples 7, 10, 24, and 57 inhibit human DGAT2 in an in vitro buffer assay.

TABLE 18

| Example | IC$_{50}$ (nM), ±SD, (n) = number of experiments |
|---|---|
| 7 | 27 ± 15 (3) |
| 10 | 52 ± 27 (3) |
| 24 | 579 ± 169 (7) |
| 57 | 103 ± 51 (4) |

Diacylglycerol Acyltransferase 2 (DGAT2) Cell-Based Assay

The inhibitory activity of compounds against human DGAT2 in a cell environment is evaluated in this assay. This assay uses human hepatoma cell-line, HepG2, as a source of acyltransferase activity.

HepG2 cell line is a commonly used model for metabolic reactions that occur in human hepatocytes in vivo. Synthesis of triglyceride in this cell line is followed by measuring incorporation of isotopically labeled oleate into triolein (a triglyceride with 3 oleoyl moieties).

Dispense the HepG2 cells into a 96-well microplate, which has been previously coated with Poly-D-lysine, in an amount of 50,000 cells/well in 100 µL Minimal Essential Media (MEM) with 10% Fetal Bovine Serum (FBS). Incubate the cells for 16 hr at 37° C. Replace the cell culture medium with MEM containing 2% Bovine Serum Albumin. Dissolve the test compound in 0.5% DMSO and prepare serial dilutions in half-log increments. Add the serially diluted test compound into separate wells. Incubate for 0.5 hr at 37° C. Thereafter replace the cell culture medium with a medium of the same composition, but which includes 50 µM $^{13}C_{18}$-oleate and 300 µM hydropropyl-β-cyclodextrine. Incubate for an additional 4 hr at 37° C. Discard the cell culture medium by flipping the microplate over thereby draining the wells and then soaking up any residual media from the wells with a paper towel. Dry the microplate at ambient temperature (~21° C.) for 10 min. Add aliquots of 125 µL of solvent (isopropyl alcohol:tetrahydrofuran:methanol:chloroform, in a ratio of 90:10:2.5:2.5 v/v), an internal standard for phosphatidylcholine (PC), and an internal standard for triacylglycerol (TG) to each well. Seal and shake the plate for 30 min at ambient temperature. Transfer 100 µL aliquots of the upper phase of each well into a wells of a deep-well plate (2 mL per well). Analyze the contents of the wells using mass-spectrometry analysis. Measure both triolein with a single $^{13}C_{18}$-oleate moiety and POPC using liquid chromatography/mass spectroscopy method (LC/MS). The degree of incorporation of a single $^{13}C_{18}$-oleate moiety into triolein, normalized to the concentration of 1-palmitoyl-2-oleoyl-phosphatidylcholine (POPC) is used as a measure of DGAT2 activity.

Determine the IC$_{50}$ for each compound, using a 4 parameter logistic curve fit. The geometric mean for the calculated IC$_{50}$ values for the compounds of Examples 7, 10, 24, and 66 are listed in Table 19 below. The data listed in Table 19 demonstrate that compounds of Examples 7, 10, 24, and 57 inhibit human DGAT2 in a cell based assay.

TABLE 19

| Example | IC$_{50}$ (nM) mean ± SD, (n) = number of experiments |
|---|---|
| 7 | 36 ± 1 (2) |
| 10 | 17 ± 1 (2) |
| 24 | 9 ± 6 (3) |
| 57 | 53 (1) |

In Vivo Pharmacodynamic Assay

This assay measures the potency of compounds by measuring the reduction in plasma triglycerides in mice treated with the test compounds compared to control animals that are treated only with the vehicle solution. Male, C57BL6 mice (10-11 weeks old, each approximately 22 g in weight) are used in this assay.

Triglycerides synthesized in the liver are secreted into circulation as a component of the Very Low Density Lipoprotein (VLDL). To prevent degradation of triglycerides in circulation by the Lipoprotein Lipase (LPL), this assay uses IV injection of a detergent, tyloxapol, which inhibits activity of LPL. Since another enzyme, DGAT1, participates in the synthesis of liver triglyceride, a saturating dose of a DGAT1 inhibitor (sodium {trans-4-[4-(4-amino-7,7-dimethyl-7H-pyrimido[4,5-b][1,4]oxazin-6-yl)phenyl]cyclohexyl}acetate, IUPAC ACDLABS naming convention, see Dow et al. *Bioorg. & Med. Chem.*, (2011) 21(20), 6122-6128) is also used in this assay.

Prepare a suspension of the test compound (DGAT2 inhibitor) mixed with the DGAT1 inhibitor in a suitable vehicle, to assure dosing of 10 mL/kg compound suspension and 3 mg/kg dose of the DGAT1 inhibitor. In this set of experiments the vehicle is 1% Hydroxyethylcellulose, 0.25% Polysorbate 80, and 0.05% Antifoam in purified water. Fast the mice for 4 hours prior to treatment. Administer to the test mice, by gavage, the suspension of the test compound (DGAT2 inhibitor) at 5 doses ranging from 0.1 to 10 mg/kg, together with the 3 mg/kg dose of the DGAT1 inhibitor. Similarly administer to a set of control mice the vehicle alone (10 mL/g). Thirty minutes later, administer to each mouse, by retro-orbital injection, a 400 mg/kg dose of tyloxapol. After an additional 30 minutes, euthanize the mice with $CO_2$.

Collect the blood via cardiac puncture into tube containing the anti-coagulant EDTA. Collect the plasma following centrifugation of blood at 3,000 g for 10 min. Freeze the plasma samples on dry ice until they are to be analyzed. Thaw the samples using wet ice. Determine the concentration of triglycerides in the plasma using an automated clinical chemistry analyzer. Reduction in total triglycerides in the test mice is calculated relative to the concentration of triglycerides in the control mice. The results for compounds of Examples 24 and 57 are listed below in Table 20. The data in Table 20 demonstrates that the compounds of Examples 24 and 57 reduce the concentration of plasma triglycerides.

TABLE 20

| Example | ED$_{50}$ (mg/kg) SD |
|---|---|
| 24 | 0.8 ± 0.09 |
| 57 | 0.23 ± 0.03 |

In Vivo Efficacy Model

The compounds described herein can be evaluated in an in vivo efficacy model.

This assay measures the potency of compounds by measuring the reduction in low density lipoprotein cholesterol (LDL-c), very low density lipoprotein cholesterol (VLDL-c), and triglycerides (TG). Male, LDL receptor-deficient mice (29 weeks old, each approximately 30 g in weight) are used in this assay.

LDL receptor deficient mice are selected for that assay to demonstrate that any measured reduction of LDL cholesterol is achieved independently of the LDL-receptor mediated uptake of LDL into the liver.

Feed the mice a standard mouse chow diet for two weeks prior to dosing. Prepare a test solution for oral gavage by suspend the compounds in acacia at 0.3, 1, and 3 mg/mL. Separate the mice into a test group and a control group. Thereafter at the first day of the third week dose the mice in the test group with the test solution for fourteen days, BID. Similarly dose the mice in the control group with just the vehicle without any of the test compound. Four hours after the last dose euthanize the mice with $CO_2$. Immediately collect the blood via cardiac puncture. Isolate the serum to measure serum triglycerides as well as cholesterol in individual lipoprotein fractions. Separate the lipoprotein fractions by known HPLC methods. Determine the cholesterol concentration associated with each lipoprotein fraction by a colorimetric method (Roche Cholesterol/HP Reagent 11875540), using isolated lipoprotein fractions with known cholesterol concentration as standards. Results obtained at the highest dose, can be expressed as the percentage of change in comparison of the LDL-c, VLDL-c and TG serum concentrations of mice in the test group to those of mice n the control group.

The results for the compound of Example 24 at 30 mg/kg bid are listed below in Table 21. The data in Table 21 demonstrate that Example 24 significantly reduces LDL-c, VLDL-c and TG serum concentrations.

TABLE 21

| Parameter | % change |
|---|---|
| LDL-c | −61% |
| VLDL-c | −74% |
| Triglycerides | −56% |

What is claimed is:

1. A compound of Formula 1 below:

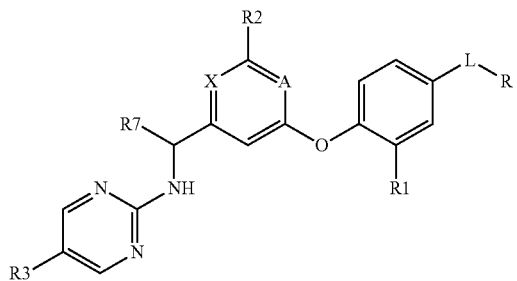

wherein:
X is CH or N;
A is CH or N, provided that at least one of X and A is N;
L is a —$C_{1-3}$alkyl;
R is selected from: —S(O)$_2$NHR4, —NHS(O)$_2$R5, and —NHC(O)—R6;
R1 is H or halo;
R2 is selected from: H, —$C_{1-2}$ alkyl, —CN, —$CF_3$, —$NH_2$, —N(H)$CH_3$, —N($CH_3$)$_2$, —$OCH_3$, —$CH_2$—O—$CH_3$, —$SCH_3$, -cyclopropyl, piperazinyl, 4-methyl piperazinyl, and morpholinyl;
R3 is selected from $C_{1-2}$ alkyl, halo, —$CHF_2$, —$CF_3$, and —$OCH_3$;
R4 is H or —$CH_3$;
R5 is selected from: —$CH_3$, —$NH_2$, and —$NHCH_3$;
R6 is selected from: —$CH_3$, —$CH_2OH$, —$CH_2OCH_3$, —CH(OH)$CH_3$, —$NH_2$, and —$NHCH_3$;
R7 is H or —$CH_3$;
provided that when R1 is H, R2 is Me, R3 is Cl, R7 is H, and X and A are both N, L-R is not —($CH_2$)S(O)$_2$—$NH_2$, or —($CH_2$)S(O)$_2$—$NHCH_3$, or
a pharmaceutically acceptable salt thereof.

2. A compound according to claim 1 wherein A is N, or a pharmaceutically acceptable salt thereof.

3. A compound according to claim 1 wherein X is N or a pharmaceutically acceptable salt thereof.

4. A compound according to claim 1 wherein X is CH or a pharmaceutically acceptable salt thereof.

5. A compound according to claim 1 wherein L is —$CH_2$— or —$CH_2CH_2$— or a pharmaceutically acceptable salt thereof.

6. A compound according to claim 1 wherein R is selected from —S(O)$_2$NHR4 and —NH(SO)$_2$R5 or a pharmaceutically acceptable salt thereof.

7. A compound according to claim 1 wherein R is —S(O)$_2$NHR4 or a pharmaceutically acceptable salt thereof.

8. A compound according to claim 1 wherein R1 is H or a pharmaceutically acceptable salt thereof.

9. A compound according to claim 1 wherein R2 is selected from: H, —$C_{1-2}$ alkyl, —CN, —$CF_3$, —$NH_2$, —N(H)$CH_3$, —N($CH_3$)$_2$, 4-methyl piperazinyl, and morpholinyl or a pharmaceutically acceptable salt thereof.

10. A compound according to claim 9 wherein R2 is selected from: H, —$CH_3$, —$NH_2$, —N(H)$CH_3$, —N($CH_3$)$_2$, 4-methyl piperazinyl, and morpholinyl or a pharmaceutically acceptable salt thereof.

11. A compound according to claim 10 wherein R2 is selected from: H, —$CH_3$, —$NH_2$, and 4-methyl piperazinyl or a pharmaceutically acceptable salt thereof.

12. A compound according to claim 1 wherein R3 is selected from: $C_{1-2}$ alkyl, and Cl or a pharmaceutically acceptable salt thereof.

13. A compound according to claim 7 wherein R4 is —$CH_3$, or a pharmaceutically acceptable salt thereof.

14. A compound according to claim 7 wherein R4 is H, or a pharmaceutically acceptable salt thereof.

15. A compound according to claim 6 wherein R5 is selected from: —$CH_3$, and —$NH_2$ or a pharmaceutically acceptable salt thereof.

16. A compound according to claim 15 wherein R5 is —$CH_3$ or a pharmaceutically acceptable salt thereof.

17. A compound according to claim 1 wherein R6 is selected from: —$CH_3$, —$CH_2OH$, —$CH_2OCH_3$, —CH(OH)Me or a pharmaceutically acceptable salt thereof.

18. A compound according to claim 1 wherein R7 is H or a pharmaceutically acceptable salt thereof.

19. A compound which is:

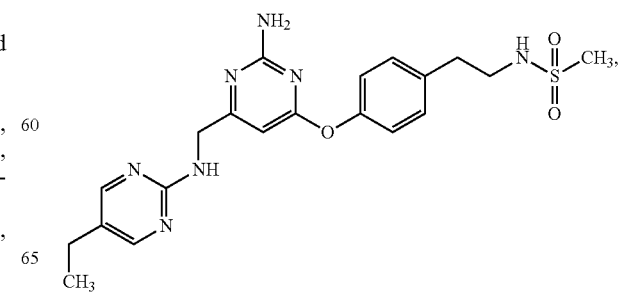

-continued or

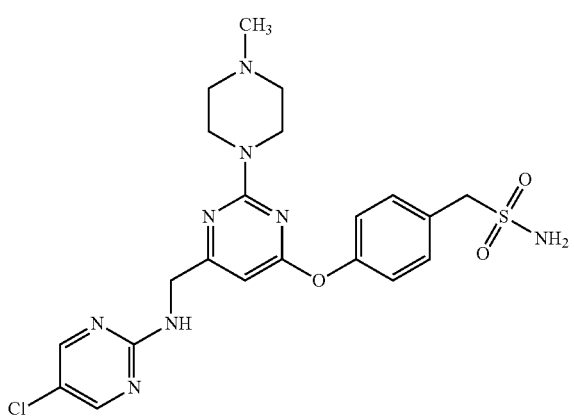

or a pharmaceutically acceptable salt thereof.

20. A pharmaceutical composition comprising a compound according to claim 1, and at least one of a pharmaceutically acceptable carrier, diluent, or excipient.

21. A pharmaceutical composition comprising a compound according to claim 19 and at least one of a pharmaceutically acceptable carrier, diluent, or excipient.

22. A method of treating a patient in need of treatment for cardiovascular disease, dyslipidemia, atherosclerosis, or hypertriglyceridemia, the method comprises administering to the patient an effective amount of a compound according to claim 1.

23. A method of treating a patient in need of treatment for cardiovascular disease, dyslipidemia, atherosclerosis, or hypertriglyceridemia, the method comprises administering to the patient an effective amount of a composition according to claim 20.

24. A method of treating a patient in need of treatment for cardiovascular disease, dyslipidemia, atherosclerosis, or hypertriglyceridemia, the method comprises administering to the patient an effective amount of a compound according to claim 19.

25. A method of treating a patient in need of treatment for cardiovascular disease, dyslipidemia, atherosclerosis, or hypertriglyceridemia, the method comprises administering to the patient an effective amount of a composition according to claim 21.

* * * * *